US008357377B2

(12) United States Patent
Pun et al.

(10) Patent No.: US 8,357,377 B2
(45) Date of Patent: Jan. 22, 2013

(54) CYCLODEXTRIN-BASED MATERIALS, COMPOSITIONS AND USES RELATED THERETO

(76) Inventors: Suzie Hwang Pun, Torrance, CA (US); Nathalie C. Bellocq, Altadena, CA (US); Mark E. Davis, Pasadena, CA (US)

( * ) Notice: Subject to any disclaimer, the term of this patent is extended or adjusted under 35 U.S.C. 154(b) by 1580 days.

(21) Appl. No.: 10/681,745

(22) Filed: Oct. 8, 2003

(65) Prior Publication Data
US 2004/0109888 A1 Jun. 10, 2004

Related U.S. Application Data

(60) Provisional application No. 60/417,373, filed on Oct. 9, 2002.

(51) Int. Cl.
A61K 9/00 (2006.01)
A61K 39/395 (2006.01)
A61K 45/00 (2006.01)
A01N 59/00 (2006.01)

(52) U.S. Cl. ............... 424/400; 424/600; 424/172.1; 424/278.1

(58) Field of Classification Search ............... 424/400
See application file for complete search history.

(56) References Cited

U.S. PATENT DOCUMENTS

| 4,367,072 | A | | 1/1983 | Vogtle et al. |
| 4,776,984 | A | * | 10/1988 | Traitler et al. ............... 554/157 |
| 4,841,081 | A | | 6/1989 | Toda et al. |
| 4,877,778 | A | | 10/1989 | Carpenter et al. |
| 4,887,778 | A | | 12/1989 | Soth et al. |
| 4,898,654 | A | | 2/1990 | Toda et al. |
| 5,098,793 | A | * | 3/1992 | Rohrbach et al. ............ 428/532 |
| 5,276,088 | A | | 1/1994 | Yoshinaga |
| 5,376,509 | A | * | 12/1994 | Yoshimoto et al. ........... 430/449 |
| 5,608,015 | A | * | 3/1997 | Yoshinaga ...................... 526/75 |
| 5,691,316 | A | * | 11/1997 | Agrawal et al. ................ 514/44 |
| 5,698,535 | A | | 12/1997 | Geczy et al. |
| 5,728,804 | A | | 3/1998 | Sharma et al. |
| 5,855,900 | A | * | 1/1999 | Nobuhiko ..................... 424/425 |
| 5,880,154 | A | | 3/1999 | Boukrinskaia et al. |
| 6,033,486 | A | | 3/2000 | Andros |
| 6,048,736 | A | * | 4/2000 | Kosak ............................ 436/536 |
| 6,060,597 | A | | 5/2000 | Tobe et al. |
| 6,068,831 | A | * | 5/2000 | Platzek et al. ................ 424/9.36 |
| 6,132,734 | A | | 10/2000 | Thomas et al. |
| 6,420,176 | B1 | | 7/2002 | Lisziewicz et al. |
| 6,509,323 | B1 | | 1/2003 | Davis et al. |
| 6,602,707 | B2 | | 8/2003 | Hefeneider et al. |
| 6,667,293 | B1 | | 12/2003 | Zhao et al. |
| 6,740,643 | B2 | | 5/2004 | Wolf et al. |
| 6,884,789 | B2 | | 4/2005 | Davis et al. |
| 7,018,609 | B2 | | 3/2006 | Pun et al. |
| 7,091,192 | B1 | | 8/2006 | Davis et al. |
| 7,132,399 | B2 | | 11/2006 | Hefeneider et al. |
| 7,166,302 | B2 | | 1/2007 | Pun et al. |
| 7,270,808 | B2 | | 9/2007 | Cheng et al. |
| 7,375,096 | B1 | | 5/2008 | Davis et al. |
| 7,807,198 | B2 | | 10/2010 | Pun et al. |
| 2001/0034333 | A1 | * | 10/2001 | Kosak ............................. 514/44 |
| 2004/0109888 | A1 | | 6/2004 | Pun et al. |
| 2007/0025952 | A1 | | 2/2007 | Davis et al. |
| 2007/0128167 | A1 | | 6/2007 | Pun et al. |
| 2008/0058427 | A1 | | 3/2008 | Cheng et al. |
| 2008/0176958 | A1 | | 7/2008 | Davis et al. |
| 2008/0279954 | A1 | | 11/2008 | Davis et al. |

FOREIGN PATENT DOCUMENTS

| GB | 1390479 | 4/1975 |
| GB | 2197720 | 5/1988 |
| HU | 200913 B | 9/1990 |
| WO | 9117300 | 11/1991 |
| WO | 9428031 | 12/1994 |
| WO | 9532739 | 12/1995 |
| WO | 9609073 | 3/1996 |
| WO | 9847536 | 10/1998 |
| WO | 9947172 | 9/1999 |
| WO | WO 00/01734 | 1/2000 |
| WO | 0006117 | 2/2000 |
| WO | WO-00/09073 | 2/2000 |
| WO | 0033885 | 6/2000 |
| WO | 0040962 | 7/2000 |
| WO | 0075162 | 12/2000 |
| WO | 0075164 | 12/2000 |
| WO | 0137665 | 5/2001 |
| WO | 0166601 | 9/2001 |
| WO | 02049676 | 6/2002 |

OTHER PUBLICATIONS

Middleton et al., Synthetic biodegradable polymers as orthpedic devices, Elsevier, Biomaterials 21 (2000) 2335-2346.*
Amiel et al. (New Associating Polymer Systems Involving Water Soluble β-Cyclodextrin Polymers (Journal of Inclusion Phenomena and Molecular Recognition in Chemistry 25: 61-67, 1996.*
Albers, E. et al., "Cyclodextrin Derivatives in Pharmaceutics", Crit. Rev. Ther. Drug Carrier Syst., 1995, 12, 311-337.
Cram, D.J., "Cavitands: Organic Hosts with Enforced Cavities", Science, 1983, 219, 1177-1183.
Cram, D.J., "The Design of Molecular Hosts, Guests, and Their Complexes", Science, 1988, 240, 760-767.
Lee, J.W. et al., "Cucurbituril Homologues and Derivatives: New Opportunities in Supramolecular Chemistry", Acc. Chem. Res., 2003, 36, 621-630.
Tenjarla, S. et al., "Preparation, Characterization, and Evaluation of Miconazole-Cyclodextrin Complexes for Improved Oral and Topical Delivery", Journal of Pharmaceutical Sciences, 1998, 87, 425-429.
Warmuth, R. et al., "Recent Highlights in Hemicarcerand Chemistry", Acc. Chem. Res., 2001, 34, 95-105.
Zughul, M.B. et al., "Thermodynamics of Propylparaben/β-Cyclodextrin Inclusion Complexes", Pharm. Dev. Technol., 1998, 3, 43-53.

(Continued)

Primary Examiner — Sreeni Padmanabhan
Assistant Examiner — Timothy E Betton
(74) Attorney, Agent, or Firm — Lando & Anastasi LLP

(57) ABSTRACT

This application discloses cyclodextrin-modified materials for carrying drugs and other active agents, such as nucleic acids. Compositions are also disclosed of cyclodextrin-modified materials that release such active agents under controlled conditions. The invention also discloses compositions of cyclodextrin-modified polymer carriers that are coupled to biorecognition molecules for assisting the delivery of drugs to their site of action.

14 Claims, 15 Drawing Sheets

OTHER PUBLICATIONS

Kang Moo Huh et al., Synthesis of a-Cyclodextrin-Conjugated Poly (e-lysine)s and Their Inclusion Complexation Behavior, Macromol. Rapid Commun., 2002, vol. 23, pp. 179-182.

International Search Report for related application No. PCT/US03/31991 dated May 17, 2004.

"Adamantane," in the Merck Index, 11th ed., Merck Research Laboratories, p. 24: No. 140 (1989).

"Amantadine," in the Merck Index, 11th ed., Merck Research Laboratories, p. 60: No. 380 (1989).

Amiel et al., "Association Between Amphiphilic Poly(ethylene oxide) and β-Cyclodextrin Polymers: Aggregation and Phase Separation," Advances in Colloid and Interface Science 79:105-122 (1999).

Amiel et al., "New Associating Polymer Systems Involving Water Soluble β-Cyclodextrin Polymers," Journal of Inclusion Phemomena and Molecular Recognition in Chemistry 25:61-67 (1996).

Boussif et al., "A Versatile Vector for Gene and Oligonucleotide Transfer into Cells in Culture and in vivo: Polyethyleninmine," Proceedings of the National Academy of Sciences 92(16):7297-7301 (1995).

Breslow et al., "Cholesterol Recognition and Binding by Cyclodextrin Dimers," J. Am. Chem. Soc. 118:8495-8496 (1996).

Cserhati, "Charge-Transfer Chromatographic Study of the Complex Formation of Some Anticancer Drugs with γ-Cyclodextrin," Analytical Biochemistry 225:328-332 (1995).

Danysz et al., "Aminoadamantanes as NMDA receptor agonists and antiparkinsonian agents-preclinical studies," Neurosci. Biobehav. Rev., vol. 21(4), pp. 455-468 (1997).

David et ai, Synthesis of hydrophobically end-capped poly(ethyleneglycol)s with UVabsorbing properties. Macromol. Rapid Commun. vol. 21(14), pp. 990-993 (2000).

Du et al., "Steric Considerations in Supramoleular Incision of Modified β-Cyclodextrins with Triton X-1 00 and α-Bromonaphthalene," Suprarnolecular Chern., vol. 7, pp. 209-214 (2005).

Epa et al., "Downregulation of the p75 Neurotrophin Receptor in Tissue Culture and in Vivo, Using β-Cyclodextrin-Adamantane-Oligonucleotide Conjugates," Antisense & Nucleic Acid Drug Development, vol. 10, pp. 469-478 (2000).

Finsinger et al., "Protective Copolymers for Nonviral Gene Vectors: Synthesis, Vector Characterization and Application in Gene Delivery," Gene Delivery 7:1183-1192 (2000).

Fisher, "A Versatile System for Receptor-Mediated Gene Delivery Permits Increased Entry of DNA into Target Cells, Enhanced Delivery to the Nucleus and Elevated Rates of Transgene Expression," Gene Therapy 7: 1337-1343 (2000).

Gonzalez et al., "New Class of Polymers for the Delivery of Macromolecular Therapeutics. Bioconjugate," Chem., vol. 10, No. 6. pp. 1068-1074 (1999).

Gosselet et al., "Association of hydrophobically modified poly (N,N-dimethylacrylamide hydroxyethylmethacrylate) with water soluble β-cyclodextrin polymers," Colloids and Surfaces: A: Physicochemical and Engineering Aspects, vol. 155, pp. 177-188 (1999).

Husain et al., "Complexation of Doxorubicin with β- and γ-Cyclodextrins," Applied Spectroscopy 46(4 ):652-658 (1992).

Hwang et al., "Effects of Structure of β-Cyclodextrin-Containing Polymers on Gene Delivery," Bioconjugate Chem 12 (2):280-290 (2001).

Iser et al., "Chenodeoxycholic acid treatment of gallstones a follow-up report and analysis of factors influencing response to therapy," N. Engl. J. Med. vol. 293(8), pp. 378-383 (1975) (abstract only).

Ooya et al., "Synthesis and Characterization of an Oligopeptide-terminated Polyrotaxane as a Drug Carrier," Polym. Adv. Technol. 11 :642-651 (2000).

Smith et al., "Spectral Characterization of β-Cyclodextrin: Triton X-1 00 Complexes," J. Include. Phen. and Mol. Rec. Chern., vol. 10, pp. 471-484 (1991).

Szente et al., "Highly soluble cyclodextrin derivatives: chemistry, properties, and trends in development," Adv. Drug. Deliv. Rev., pp. 3617-3628 (1999).

Tabushi et al., "Artificial Receptor Recognizing Hydrophobic Carbonyl Compounds," Journal of Organic Chemistry 51 (1 0):1918-1921 (1986).

Tojima et al., "Preparation of an α-Cyclodextrin-Linked Chitosan Derivative via Reductive Amination Strategy," J. Polym. Sci., Part A: Polym. Chem. 36:1965-1968 (1998).

Torchilin et al., "TAT Peptide on the Surface of Liposomes Affords Their Efficient Intracellular Delivery Even at Low Temperature and in the Presence of ametabolic Inhibitors," PNAS 98(15)8786-8791 (2001).

Uekama et al., "Cyclodextrin Drug Carrier Systems," Chem. Rev. 98:2045-2076 (1998).

Weickenmeier and Wenz, "Cyclodextrin sidechain polyesters—synthesis and inclusion of adamantan derivatives," Macromol. Rapid Commun., vol. 17, pp. 731-736 (1996).

Zanta et al., "In Vitro Gene Delivery to Hepatocytes with Galactosylated Polyethylenimine," Bioconjugate Chem. 8:839-844 (1997).

Zhang et al., "Enthalpic Domination of the Chelate Effect in Cyclodextrin Dimers," J. Am. Chem. Soc. 115:9353-9354 (1993).

European Search Report from EP application No. 03786526.8 dated Sep. 3, 2010.

Amiel et al., New Associateing Polymer Systems Involving Water Soluble β-Cyclodextrin Polymers. Journal of Inclusion Phenomena and Molecular Recognition in Chemistry. vol. 25, pp. 61-67 (1996).

Sandier et al., Interaction Between an Adamantane End-Capped Poly(ethylene oxide) and a β-Cyclodextrin Polymer. American Cancer Society. vol. 16, pp. 1634-1642 (2000).

* cited by examiner

Figure 1
A 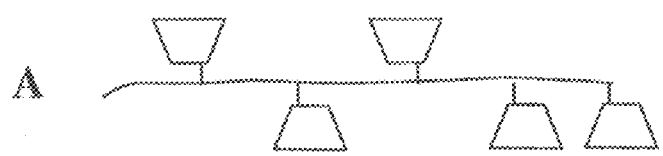
B 
P 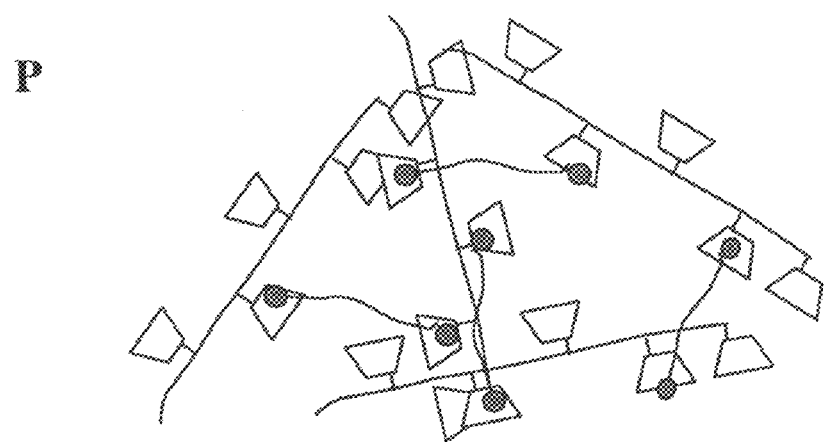

Figure 5
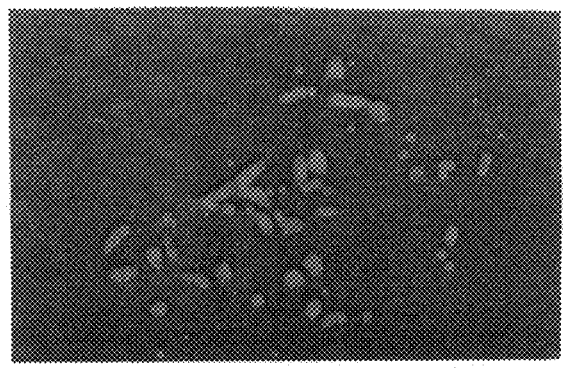
No Matrix
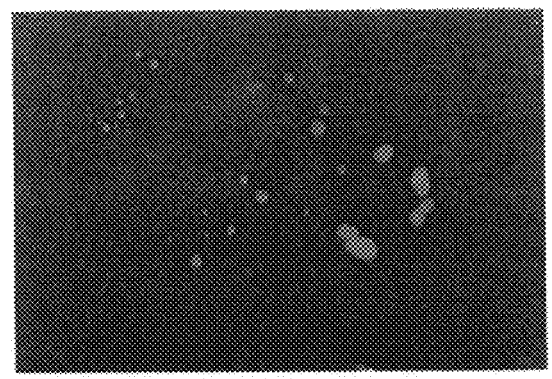
Matrix + PDGF
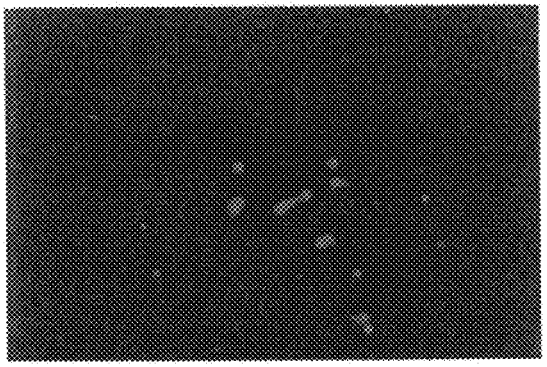
Matrix

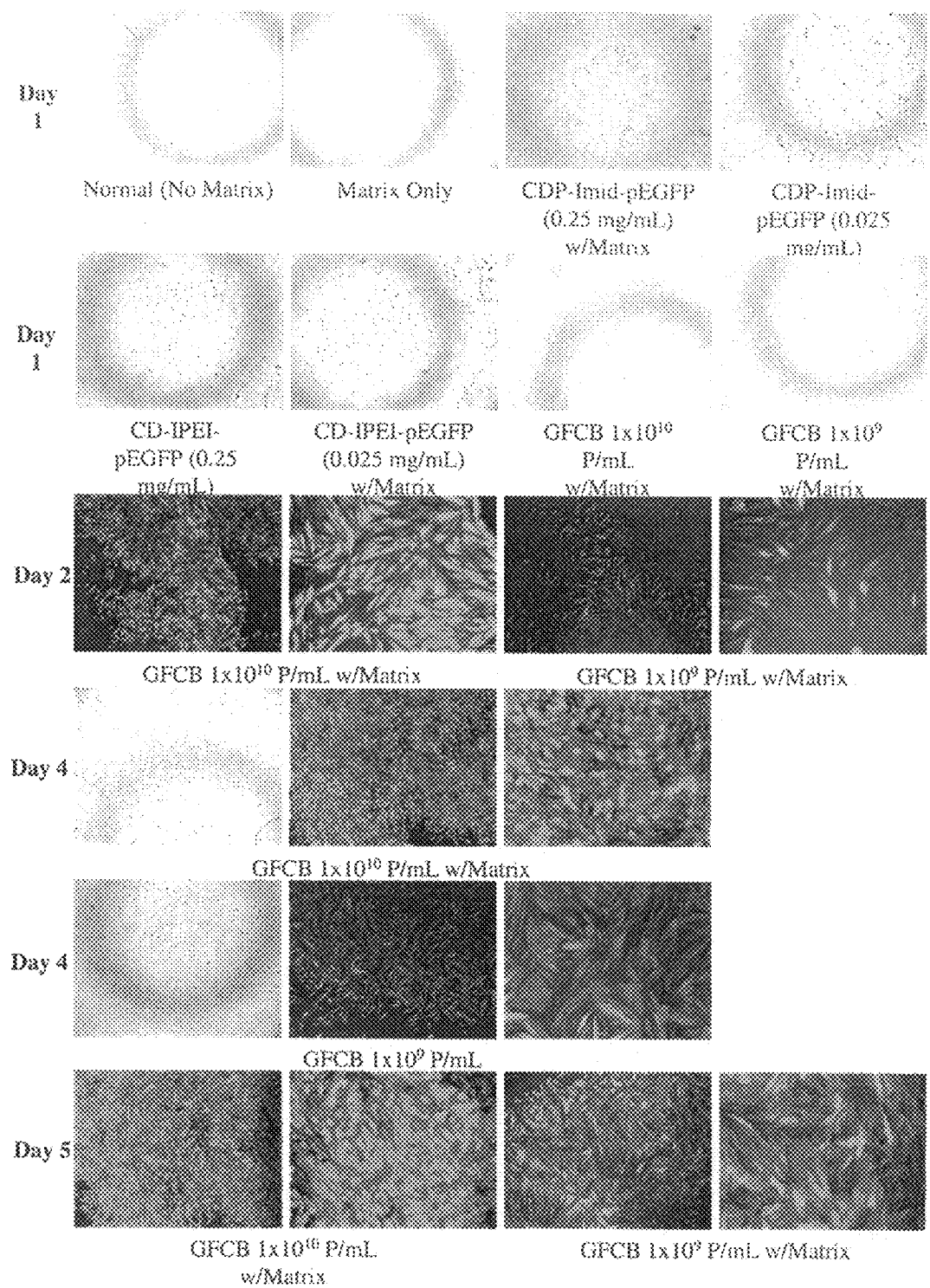
Figure 11 (Page 1 of 2)

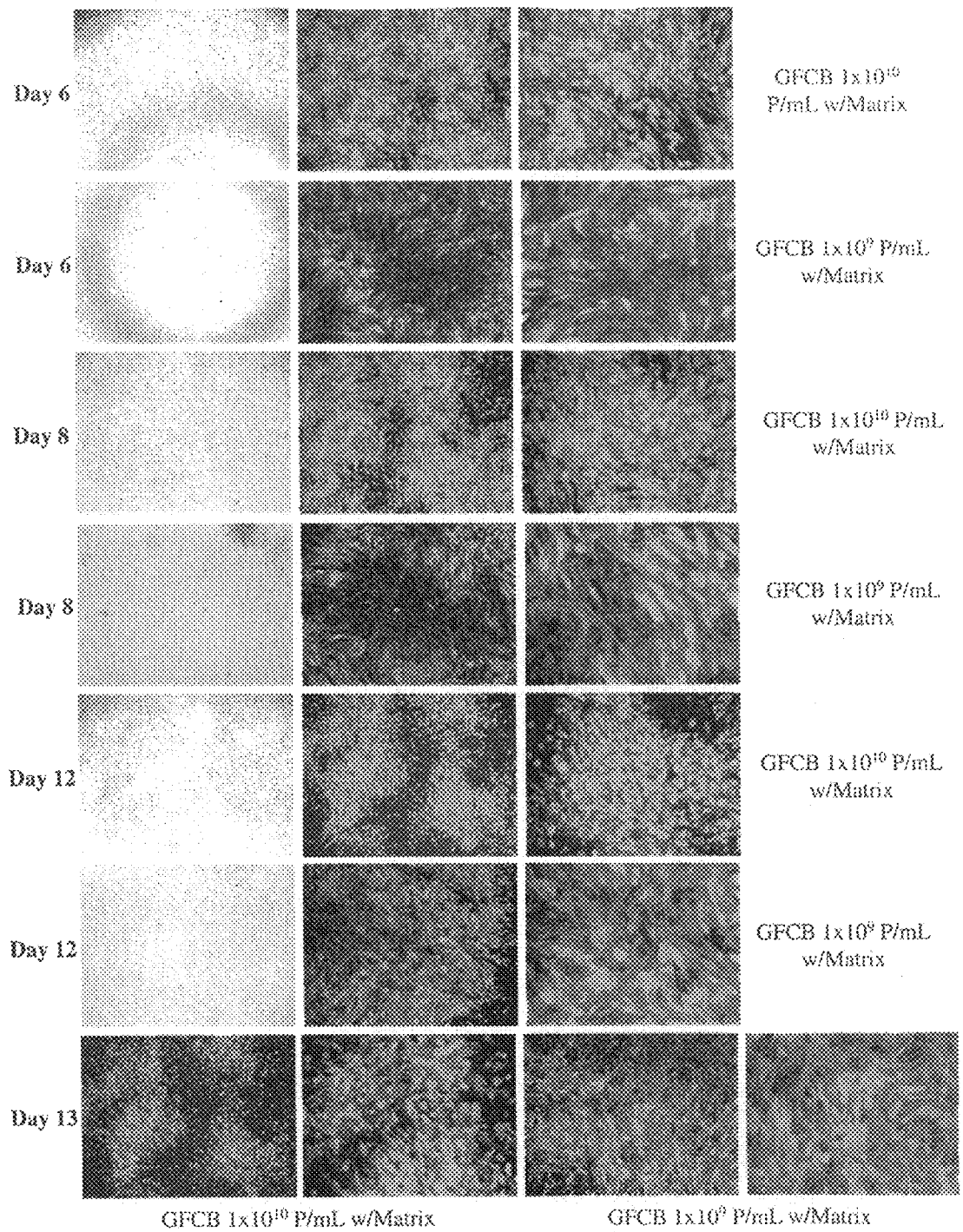
Figure 11 (Page 2 of 2)

CYCLODEXTRIN-BASED MATERIALS, COMPOSITIONS AND USES RELATED THERETO

RELATED APPLICATIONS

This application is based on U.S. Provisional Application No. 60/417,373, filed Oct. 9, 2002, the specification of which is hereby incorporated by reference in its entirety herein.

BACKGROUND OF THE INVENTION

Polymers having pendant sugar moieties known as "glycopolymers" (Bioconj. Chem., 3:256 (1992)) have attracted much interest in recent years, largely as scaffolds for the multi-valent display of biologically important carbohydrate molecules. These glycopolymers have been used as potent inhibitors of viral-host cell attachment and leukocyte-endothelial cell adhesion (FEBS, 272:209 (1990); Can. J. Microbiol., 37:233 (1991); J. Am. Chem. Soc., 119:3161 (1997)). Glycopolymers have also been explored as vehicles for targeted drug and gene delivery (J. Hepatology, 21:806 (1994)), and as artificial substrates for cell adhesion (J. Cell Biol., 115:485 (1991)). The suitability of glycopolymers as biocompatible implant materials has been relatively unexplored and is limited to a few examples described, for example, in Microbiol. Chem. Phys., 195:3597 (1994).

For polymers used as biocompatible implant materials, their properties, particularly the surface composition, are of great importance. Efforts include introducing biocompatible components into the bulk system and on their surface. Studies described, for example, in J. Colloid Interface Sci., 149:84 (1992) have shown that copolymers with a pendant glucose unit in the bulk or surfaces with covalently bound neutral polysaccharides demonstrate the reduction of platelet adhesion and protein adsorption.

Accordingly, biocompatible polymeric materials that are easily prepared would be useful for drug delivery and other biomedical uses.

SUMMARY OF THE INVENTION

This invention provides a material formed by crosslinking a polymer bearing inclusion hosts (such as cyclodextrin) with a linking molecule bearing at least two functional groups that,

SUMMARY OF THE INVENTION

This invention provides a material formed by crosslinking a polymer bearing inclusion hosts (such as cyclodextrin) with a linking molecule bearing at least two functional groups that, as inclusion guests, form inclusion complexes with the inclusion host. For polymers in which cyclodextrin is the inclusion host, exemplary inclusion guests include naphthol, adamantane, cholesterol, and derivatives thereof. In certain embodiments, the polymer bears inclusion guests, and linking molecules bearing inclusion hosts such as cyclodextrin are used to crosslink the polymer. Materials according to the above description can be used to deliver therapeutic agents, such as proteins, nucleic acids, and pharmaceuticals.

BRIEF DESCRIPTION OF THE DRAWINGS

FIG. 1 schematically depicts a crosslinked polymer matrix of the present invention.

FIG. 5 shows cell migration through a matrix as described herein.

FIG. 11 illustrates results of in vitro assays using a matrix as described herein.

DETAILED DESCRIPTION OF THE INVENTION

I. Overview

Figure 2:
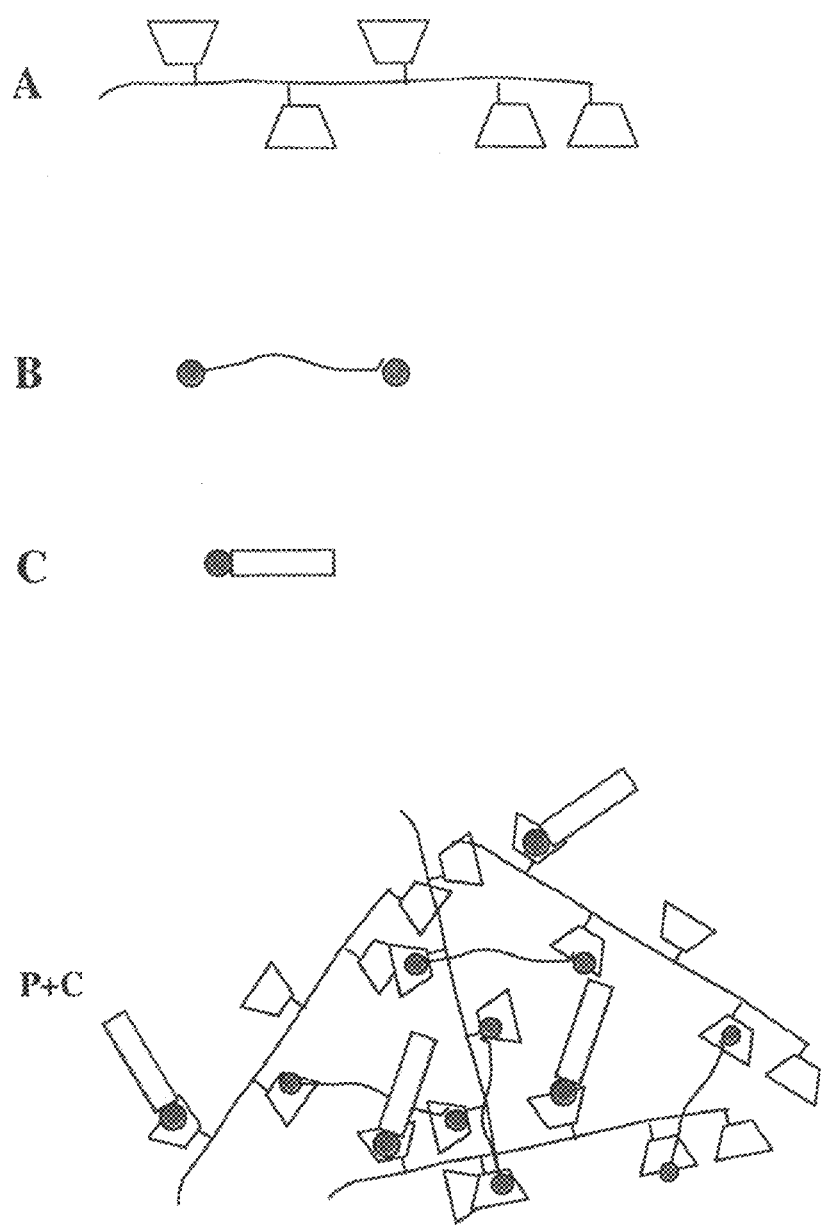
FIG. 2 illustrates a matrix of the invention including therapeutic moieties.

Cyclodextrins have a ring structure which has a basket-like shape. This shape allows cyclodextrins to include many kinds of molecules into their internal cavity. See, for example, Szejtli, *Cyclodextrins and Their Inclusion Complexes*; Akademiai Klado, Budapest, 1982; and Bender et al., *Cyclodextrin Chemistry*, Springer-Verlag, Berlin, 1978. Cyclodextrins are able to form inclusion complexes with an array of organic molecules including, for example, drugs, pesticides, herbicides, and agents of war. See, Tenjarla et al., *J. Pharm. Sci.*, 87: 425-429 (1998); Zughul et al., *Pharm. Dev. Technol.*, 3: 43-53 (1998); and Albers et al., *Crit. Rev. Ther. Drug Carrier Syst.*, 12: 311-337 (1995).

Linear cyclodextrin-based polymers (CDPs) have previously been shown to have low toxicity both in vitro (in many different cell lines) and in vivo (Gonzalez et al. 1999 *Bioconjugate Chem* 10:1068-1074; and Hwang et al. 2001 *Bioconjugate Chem* 12(2):280-290). The present invention relates, at least in part, to biocompatible materials based on polymers that bear or include cyclodextrin moieties, by crosslinking the linear strands with linking molecules bearing two or more moieties that form inclusion complexes with cyclodextrin, as shown in FIG. 1. Additionally, those of skill in the art will recognize that this concept can naturally be extended to polymers bearing or including inclusion hosts other than cyclodextrin, in conjunction with linking molecules that bear inclusion guests that form inclusion complexes with those inclusion hosts, or, alternatively, polymers that bear inclusion guests in conjunction with linking molecules that bear or include inclusion hosts that form inclusion complexes with those inclusion guests. Examples of inclusion hosts other than cyclodextrins and related cycloamyloses include perhydrotriphenylene (which forms inclusion complexes with polyethylene), urea/thiourea (which form inclusion complexes with fatty acids and related molecules as described in U.S. Pat. Nos. 4,776,984, 5,106,542, and 4,170,601), cyclophanes (such as those described in U.S. Pat. No. 4,116,955), and those described in U.S. Pat. Nos. 4,841,081, 4,367,072, and 4,898,654, all of which are hereby incorporated by reference in their entireties.

In certain embodiments of the present invention, such as is described below in Example 19, a polymer bears both inclusion hosts and inclusion guests, and thus crosslinks with itself by forming inclusion complexes between hosts and guests on the same polymer chain and/or between hosts and guests on adjacent polymer chains. Conditions under which the crosslinking is performed will influence the balance between these two types of inclusion complexes. For example, performing the complexation at high dilution will favor the formation of intramolecular complexes, while performing the complexation at high concentrations will favor the formation of intermolecular complexes, including, in some cases, catenane- and rotaxane-type structures. In certain such embodiments, a high degree of intermolecular interaction increases the rigidity, melting point, and strength of the material.

For purposes of the present application, polymers 'incorporate' inclusion hosts, such as cyclodextrin moieties, by having inclusion hosts within the polymer chain, e.g., removing inclusion hosts from the polymer would require severing the polymer chain. Examples of such polymers are the linear cyclodextrin-based polymers referred to above. Polymers that 'bear' cyclodextrin moieties have a polymer chain to which inclusion hosts are attached, e.g., inclusion hosts are appended to a distinct polymer chain. Polyethylenimine-CD polymers as described herein are examples of this type of polymer. Polymers that 'include' inclusion hosts are those polymers that 'bear' or 'incorporate', or both bear and incorporate, inclusion hosts, or otherwise have covalently bound inclusion hosts as part of the polymer chain. Any polymer that includes inclusion hosts can be employed in the present application. In certain embodiments, a polymer that incorporates inclusion hosts is a linear (i.e., non-branched) polymer. In certain embodiments, inclusion hosts, e.g., incorporated into or borne on the polymer, are regularly spaced throughout or along the polymer.

The physical properties of the resultant material can be varied by selecting moieties that form inclusion complexes of varying strength; the stronger the complex, the more durable and rigid the resulting material. Similarly, using linking molecules bearing more than two such moieties may increase the strength and rigidity of the material by increasing the degree of crosslinking, as will increasing the proportion of linking molecules to polymer mass. Physical properties of the material can also be varied by altering the flexibility of the linking molecules themselves, or by altering the flexibility of linkers within the cyclodextrin polymer itself.

Furthermore, the in vivo properties of the matrix may be varied by using bonds in the matrix that are labile under physiological conditions. For example, the polymer strands, the crosslinking molecules, or both, may comprise bonds that are labile under physiological conditions, such as ester and peptide bonds. After placement in a physiological environment, these bonds will gradually begin to cleave, resulting in a gradual degradation and loss of structural integrity. A wide spectrum of properties can be achieved by varying the frequency of such bonds in a polymer strand, by combining labile and resistant crosslinking molecules in varying proportions, or by selecting different labile bonds with differing strengths. For example a peptide bond is generally more resistant to cleavage than an ester bond, which is in turn less labile than a thioester bond.

Compounds and materials such as therapeutic agents, viruses, adjuvants, and the like, can be formulated with the polymer by forming inclusion complexes, or by simple admixture or encapsulation, without forming inclusion complexes, as is well known in the art for ordinary biocompatible polymers.

Compounds increasing the therapeutic utility of the material, such as signaling peptides, other moieties facilitating cell migration, or adjuvants, may be incorporated into the crosslinked material by conjugating an inclusion complex guest to the entity of interest and including the conjugate in the material as depicted in FIG. 2. The conjugate may be included before, during or after the crosslinking process. Therapeutic compounds may also be included in this fashion, preferably where the attachment between the drug and the inclusion guest/host is labile under physiological conditions, such as an ester bond. See U.S. Patent Application Publication Nos. 20030008818 and 20030017972.

II. Definitions

For convenience, certain terms employed in the specification, examples, and appended claims are collected here.

An 'adjuvant', as the term is used herein, is a compound that has little or no therapeutic value on its own, but increases the effectiveness of a therapeutic agent. Exemplary adjuvants include radiosensitizers, transfection-enhancing agents (such as chloroquine and analogs thereof), chemotactic agents and chemoattractants, peptides that modulate cell adhesion and/or cell mobility, cell permeabilizing agents, inhibitors of multidrug resistance and/or efflux pumps, etc.

The terms "biocompatible polymer" and "biocompatibility" when used in relation to polymers are art-recognized. For example, biocompatible polymers include polymers that are neither themselves toxic to the host (e.g., an animal or human), nor degrade (if the polymer degrades) at a rate that produces monomeric or oligomeric subunits or other byproducts at toxic concentrations in the host. In certain embodiments of the present invention, biodegradation generally involves degradation of the polymer in an organism, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible. Hence, a subject composition may comprise 99%, 98%, 97%, 96%, 95%, 90% 85%, 80%, 75% or even less of biocompatible polymers, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1 M NaOH at 37° C. until complete degradation is observed. The solution is then neutralized with 1 M HCl. About 200 µL of various concentrations of the degraded sample products are placed in 96-well tissue culture plates and seeded with human gastric carcinoma cells (GT3TKB) at 104/well density. The degraded sample products are incubated with the GT3TKB cells for 48 hours. The results of the assay may be plotted as % relative growth vs. concentration of degraded sample in the tissue-culture well. In addition, polymers and formulations of the present invention may also be evaluated by well-known in vivo tests, such as subcutaneous implantations in rats to confirm that they do not cause significant levels of irritation or inflammation at the subcutaneous implantation sites.

The term "biodegradable" is art-recognized, and includes polymers, compositions and formulations, such as those described herein, that are intended to degrade during use. Biodegradable polymers typically differ from non-biodegradable polymers in that the former may be degraded during use. In certain embodiments, such use involves in vivo use, such as in vivo therapy, and in other certain embodiments, such use involves in vitro use. In general, degradation attributable to biodegradability involves the degradation of a biodegradable polymer into its component subunits, or digestion, e.g., by a biochemical process, of the polymer into smaller, non-polymeric subunits. In certain embodiments, two different types of biodegradation may generally be identified. For example, one type of biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. In contrast, another type of biodegradation may involve cleavage of a bond (whether covalent or otherwise) internal to sidechain or that connects a side chain to the polymer backbone. For example, a therapeutic agent or other chemical moiety attached as a side chain to the polymer backbone may be released by biodegradation. In certain embodiments, one or the other or both general types of biodegradation may occur during use of a polymer.

As used herein, the term "biodegradation" encompasses both general types of biodegradation. The degradation rate of a biodegradable polymer often depends in part on a variety of factors, including the chemical identity of the linkage responsible for any degradation, the molecular weight, crystallinity, biostability, and degree of cross-linking of such polymer, the physical characteristics (e.g., shape and size) of an implant, and the mode and location of administration. For example, the greater the molecular weight, the higher the degree of crystallinity, and/or the greater the biostability, the biodegradation of any biodegradable polymer is usually slower. The term "biodegradable" is intended to cover materials and processes also termed "bioerodible".

In certain embodiments wherein the biodegradable polymer also has a therapeutic agent or other material associated with it, the biodegradation rate of such polymer may be characterized by a release rate of such materials. In such circumstances, the biodegradation rate may depend on not only the chemical identity and physical characteristics of the polymer, but also on the identity of material(s) incorporated therein. Degradation of the subject compositions includes not only the cleavage of intramolecular bonds, e.g., by oxidation and/or hydrolysis, but also the disruption of intermolecular bonds, such as dissociation of host/guest complexes by competitive complex formation with foreign inclusion hosts.

In certain embodiments, polymeric formulations of the present invention biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 and 8 having a temperature of between 25 and 37° C. In other embodiments, the polymer degrades in a period of between about one hour and several weeks, depending on the desired application.

A biohydrolyzable bond (e.g., ester, amide, carbonate, carbamates, or imide) refers to a bond that is cleaved (e.g., an ester is cleaved to form a hydroxyl and a carboxylic acid) under physiological conditions. Physiological conditions include the acidic and basic environments of the digestive tract (e.g., stomach, intestines, etc.), acidic environment of a tumor, enzymatic cleavage, metabolism, and other biological processes, and preferably refer to physiological conditions in a vertebrate, such as a mammal.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMO's.

"Instruction(s)" as used herein means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

"Kit" as used herein means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, the term 'RNAi construct' is a generic term including small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

An 'effective amount' of a subject compound, with respect to the subject method of treatment, refers to an amount of the therapeutic in a preparation which, when applied as part of a desired dosage regimen provides a benefit according to clinically acceptable standards for the treatment or prophylaxis of a particular disorder.

'Patients' or 'subjects' to be treated by the subject method are animals, preferably mammals, including humans.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e., it is intended to diminish, ameliorate, or stabilize the existing unwanted condition or side effects thereof).

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the frequency of, or alternatively delaying, pain sensations experienced by subjects in a treated population versus an untreated control population.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. More particularly, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "therapeutic index" refers to the therapeutic index of a drug defined as $LD_{50}/ED_{50}$ 'Acyl' refers to a group suitable for acylating a nitrogen atom to form an amide or carbamate, a carbon atom to form a ketone, a sulfur atom to form a thioester, or an oxygen atom to form an ester group, e.g., a hydrocarbon attached to a —C(=O)— moiety. Preferred acyl groups include benzoyl, acetyl, tert-butyl acetyl, pivaloyl, and trifluoroacetyl. More preferred acyl groups include acetyl and benzoyl. The most preferred acyl group is acetyl.

The term 'acylamino' is art-recognized and preferably refers to a moiety that can be represented by the general formula:

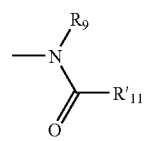

wherein $R_9$ and $R_{10}$, $R'_{10}$ each independently represent hydrogen or a hydrocarbon substituent, such as alkyl, heteroalkyl, aryl, heteroaryl, carbocyclic aliphatic, and heterocyclic aliphatic.

The terms 'amine' and 'amino' are art-recognized and refer to both unsubstituted and substituted amines as well as ammonium salts, e.g., as can be represented by the general formula:

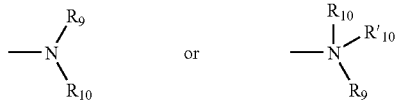

wherein $R_9$, $R_{10}$, and $R'_{10}$ each independently represent hydrogen or a hydrocarbon substituent, or $R_9$ and $R_{10}$ taken together with the N atom to which they are attached complete a heterocycle having from 4 to 8 atoms in the ring structure. In preferred embodiments, none of $R_9$, $R_{10}$, and $R'_{10}$ is acyl, e.g., $R_9$, $R_{10}$, and $R'_{10}$ are selected from hydrogen, alkyl, heteroalkyl, aryl, heteroaryl, carbocyclic aliphatic, and heterocyclic aliphatic. The term 'alkylamine' as used herein means an amine group, as defined above, having at least one substituted or unsubstituted alkyl attached thereto. Amino groups that are positively charged (e.g., $R'_{10}$ is present) are referred to as 'ammonium' groups. In amino groups other than ammonium groups, the amine is preferably basic, e.g., its conjugate acid has a $pK_a$ above 7.

The terms 'amido' and 'amide' are art-recognized as an amino-substituted carbonyl, such as a moiety that can be represented by the general formula:

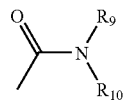

wherein $R_9$ and $R_{10}$ are as defined above. In certain embodiments, the amide will include imides.

'Alkyl' refers to a saturated or unsaturated hydrocarbon chain having 1 to 18 carbon atoms, preferably 1 to 12, more preferably 1 to 6, more preferably still 1 to 4 carbon atoms. Alkyl chains may be straight (e.g., n-butyl) or branched (e.g., sec-butyl, isobutyl, or t-butyl). Preferred branched alkyls have one or two branches, preferably one branch. Preferred alkyls are saturated. Unsaturated alkyls have one or more double bonds and/or one or more triple bonds. Preferred unsaturated alkyls have one or two double bonds or one triple bond, more preferably one double bond. Alkyl chains may be unsubstituted or substituted with from 1 to 4 substituents. Preferred alkyls are unsubstituted. Preferred substituted alkyls are mono-, di-, or trisubstituted. Preferred alkyl substituents include halo, haloalkyl, hydroxy, aryl (e.g., phenyl, tolyl, alkoxyphenyl, alkyloxycarbonylphenyl, halophenyl), heterocyclyl, and heteroaryl.

The terms 'alkenyl' and 'alkynyl' refer to unsaturated aliphatic groups analogous in length and possible substitution to the alkyls described above, but that contain at least one double or triple bond, respectively. When not otherwise indicated, the terms alkenyl and alkynyl preferably refer to lower alkenyl and lower alkynyl groups, respectively. When the term alkyl is present in a list with the terms alkenyl and alkynyl, the term alkyl refers to saturated alkyls exclusive of alkenyls and alkynyls.

The terms 'alkoxyl' and 'alkoxy' as used herein refer to an —O-alkyl group. Representative alkoxyl groups include methoxy, ethoxy, propyloxy, tert-butoxy, and the like. An 'ether' is two hydrocarbons covalently linked by an oxygen. Accordingly, the substituent of a hydrocarbon that renders that hydrocarbon an ether can be an alkoxyl, or another moiety such as —O-aryl, —O-heteroaryl, —O-heteroalkyl, —O-aralkyl, —O-heteroaralkyl, —O-carbocylic aliphatic, or —O-heterocyclic aliphatic.

The term 'alkylthio' refers to an —S-alkyl group. Representative alkylthio groups include methylthio, ethylthio, and the like. 'Thioether' refers to a sulfur atom bound to two hydrocarbon substituents, e.g., an ether wherein the oxygen is replaced by sulfur. Thus, a thioether substituent on a carbon atom refers to a hydrocarbon-substituted sulfur atom substituent, such as alkylthio or arylthio, etc.

The term 'aralkyl', as used herein, refers to an alkyl group substituted with an aryl group.

'Aryl ring' refers to an aromatic hydrocarbon ring system. Aromatic rings are monocyclic or fused bicyclic ring systems, such as phenyl, naphthyl, etc. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring. The term 'aryl' also includes bicyclic ring systems wherein only one of the rings is aromatic, e.g., the other ring is cycloalkyl, cycloalkenyl, or heterocyclyl. Aromatic rings may be unsubstituted or substituted with from 1 to about 5 substituents on the ring. Preferred aromatic ring substituents include: halo, cyano, lower alkyl, heteroalkyl, haloalkyl, phenyl, phenoxy, or any combination thereof. More preferred substituents include lower alkyl, cyano, halo, and haloalkyl.

'Carbocyclic aliphatic ring' refers to a saturated or unsaturated hydrocarbon ring. Carbocyclic aliphatic rings are not aromatic. Carbocyclic aliphatic rings are monocyclic, or are fused, spiro, or bridged bicyclic ring systems. Monocyclic carbocyclic aliphatic rings contain from about 4 to about 10 carbon atoms, preferably from 4 to 7 carbon atoms, and most preferably from 5 to 6 carbon atoms in the ring. Bicyclic carbocyclic aliphatic rings contain from 8 to 12 carbon atoms, preferably from 9 to 10 carbon atoms in the ring. Carbocyclic aliphatic rings may be unsubstituted or substituted with from 1 to 4 substituents on the ring. Preferred carbocyclic aliphatic ring substituents include halo, cyano, alkyl, heteroalkyl, haloalkyl, phenyl, phenoxy or any combination thereof. More preferred substituents include halo and haloalkyl. Preferred carbocyclic aliphatic rings include cyclopentyl, cyclohexyl, cyclohexenyl, cycloheptyl, and cyclooctyl. More preferred carbocyclic aliphatic rings include cyclohexyl, cycloheptyl, and cyclooctyl.

The term 'carbonyl' is art-recognized and includes such moieties as can be represented by the general formula:

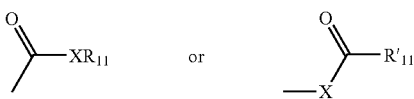

wherein X is a bond or represents an oxygen or a sulfur, and $R_{11}$ represents a hydrogen, hydrocarbon substituent, or a pharmaceutically acceptable salt, $R_{11'}$ represents a hydrogen or hydrocarbon substituent. Where X is an oxygen and $R_{11}$ or $R_{11'}$ is not hydrogen, the formula represents an 'ester'. Where X is an oxygen, and $R_{11}$ is as defined above, the moiety is referred to herein as a carboxyl group, and particularly when $R_{11}$ is a hydrogen, the formula represents a 'carboxylic acid'. Where X is an oxygen, and $R_{11'}$ is hydrogen, the formula represents a 'formate'. In general, where the oxygen atom of the above formula is replaced by sulfur, the formula represents a 'thiocarbonyl' group. Where X is a sulfur and $R_{11}$ or $R_{11'}$ is not hydrogen, the formula represents a 'thioester.' Where X is a sulfur and $R_{11}$ is hydrogen, the formula represents a 'thiocarboxylic acid.' Where X is a sulfur and $R_{11'}$ is hydrogen, the formula represents a 'thioformate.' On the other hand, where X is a bond, $R_{11}$ is not hydrogen, and the carbonyl is bound to a hydrocarbon, the above formula represents a 'ketone' group. Where X is a bond, $R_{11}$ is hydrogen, and the carbonyl is bound to a hydrocarbon, the above formula represents an 'aldehyde' or 'formyl' group.

'Ci alkyl' is an alkyl chain having i member atoms. For example, C4 alkyls contain four carbon member atoms. C4 alkyls containing may be saturated or unsaturated with one or two double bonds (cis or trans) or one triple bond. Preferred C4 alkyls are saturated. Preferred unsaturated C4 alkyl have one double bond. C4 alkyl may be unsubstituted or substituted with one or two substituents. Preferred substituents include lower alkyl, lower heteroalkyl, cyano, halo, and haloalkyl.

'Halogen' refers to fluoro, chloro, bromo, or iodo substituents. Preferred halo are fluoro, chloro and bromo; more preferred are chloro and fluoro. 'Haloalkyl' refers to a straight, branched, or cyclic hydrocarbon substituted with one or more halo substituents. Preferred haloalkyl are C1-C12; more preferred are C1-C6; more preferred still are C1-C3. Preferred halo substituents are fluoro and chloro. The most preferred haloalkyl is trifluoromethyl.

'Heteroalkyl' is a saturated or unsaturated chain of carbon atoms and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to about 4 substituents unless otherwise specified. Preferred heteroalkyl are unsubstituted. Preferred heteroalkyl substituents include halo, aryl (e.g., phenyl, tolyl, alkoxyphenyl, alkoxycarbonylphenyl, halophenyl), heterocyclyl, heteroaryl. For example, alkyl chains substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkoxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkoxycarbonylphenylthio), amino (e.g., amino, mono- and di-C1-C3 alkylamino, methylphenylamino, methylbenzylamino, C1-C3 alkylamido, carbamamido, ureido, guanidino).

'Heteroatom' refers to a multivalent non-carbon atom, such as a boron, phosphorous, silicon, nitrogen, sulfur, or oxygen atom, preferably a nitrogen, sulfur, or oxygen atom. Groups containing more than one heteroatom may contain different heteroatoms.

'Heteroaryl ring' refers to an aromatic ring system containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 in the ring. Bicyclic heteroaromatic rings contain from 8 to 12 member atoms, preferably 9 or 10 member atoms in the ring. The term 'heteroaryl' also includes bicyclic ring systems wherein only one of the rings is aromatic, e.g., the other ring is cycloalkyl, cycloalkenyl, or heterocyclyl. Heteroaromatic rings may be unsubstituted or substituted with from 1 to about 4 substituents on the ring. Preferred heteroaromatic ring substituents include halo, cyano, lower alkyl, heteroalkyl, haloalkyl, phenyl, phenoxy or any combination thereof. Preferred heteroaromatic rings include thienyl, thiazolyl, oxazolyl, pyrrolyl, purinyl, pyrimidyl, pyridyl, and furanyl. More preferred heteroaromatic rings include thienyl, furanyl, and pyridyl.

'Heterocyclic aliphatic ring' is a non-aromatic saturated or unsaturated ring containing carbon and from 1 to about 4 heteroatoms in the ring, wherein no two heteroatoms are adjacent in the ring and preferably no carbon in the ring attached to a heteroatom also has a hydroxyl, amino, or thiol group attached to it. Heterocyclic aliphatic rings are monocyclic, or are fused or bridged bicyclic ring systems. Monocyclic heterocyclic aliphatic rings contain from about 4 to about 10 member atoms (carbon and heteroatoms), preferably from 4 to 7, and most preferably from 5 to 6 member atoms in the ring. Bicyclic heterocyclic aliphatic rings contain from 8 to 12 member atoms, preferably 9 or 10 member atoms in the ring. Heterocyclic aliphatic rings may be unsubstituted or substituted with from 1 to about 4 substituents on the ring. Preferred heterocyclic aliphatic ring substituents include halo, cyano, lower alkyl, heteroalkyl, haloalkyl, phenyl, phenoxy or any combination thereof. More preferred substituents include halo and haloalkyl. Heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, hydantoin, oxazoline, imidazolinetrione, triazolinone, quinoline, phthalazine, naphthyridine, quinoxaline, quinazoline, quinoline, pteridine, carbazole, carboline, phenanthridine, acridine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. Preferred heterocyclic aliphatic rings include piperazyl, morpholinyl, tetrahydrofuranyl, tetrahydropyranyl and piperidyl. Heterocycles can also be polycycles.

The term 'hydroxyl' means —OH.

'Lower alkyl' refers to an alkyl chain comprised of 1 to 5, preferably 1 to 4 carbon member atoms, more preferably 1 or 2 carbon member atoms. Lower alkyls may be saturated or unsaturated. Preferred lower alkyls are saturated. Lower alkyls may be unsubstituted or substituted with one or about two substituents. Preferred substituents on lower alkyl include cyano, halo, trifluoromethyl, amino, and hydroxyl. Throughout the application, preferred alkyl groups are lower alkyls. In preferred embodiments, a substituent designated herein as alkyl is a lower alkyl. Likewise, 'lower alkenyl' and 'lower alkynyl' have similar chain lengths.

'Lower heteroalkyl' refers to a heteroalkyl chain comprised of 1 to 4, preferably 1 to 3 member atoms, more preferably 1 to 2 member atoms. Lower heteroalkyl contain one or two non-adjacent heteroatom member atoms. Preferred lower heteroalkyl contain one heteroatom member atom. Lower heteroalkyl may be saturated or unsaturated. Preferred lower heteroalkyl are saturated. Lower heteroalkyl may be unsubstituted or substituted with one or about two substituents. Preferred substituents on lower heteroalkyl include cyano, halo, trifluoromethyl, and hydroxyl.

'Mi heteroalkyl' is a heteroalkyl chain having i member atoms. For example, M4 heteroalkyls contain one or two non-adjacent heteroatom member atoms. M4 heteroalkyls containing 1 heteroatom member atom may be saturated or unsaturated with one double bond (cis or trans) or one triple bond. Preferred M4 heteroalkyl containing 2 heteroatom member atoms are saturated. Preferred unsaturated M4 heteroalkyl have one double bond. M4 heteroalkyl may be unsubstituted or substituted with one or two substituents. Preferred substituents include lower alkyl, lower heteroalkyl, cyano, halo, and haloalkyl.

'Isocyanate' refers to the group —NCO.

'Member atom' refers to a polyvalent atom (e.g., C, O, N, or S atom) in a chain or ring system that constitutes a part of the chain or ring. For example, in cresol, six carbon atoms are member atoms of the ring and the oxygen atom and the carbon atom of the methyl substituent are not member atoms of the ring.

As used herein, the term 'nitro' means —$NO_2$.

'Pharmaceutically acceptable salt' refers to a cationic salt formed at any acidic (e.g., hydroxamic or carboxylic acid) group, or an anionic salt formed at any basic (e.g., amino or guanidino) group. Such salts are well known in the art. See e.g., World Patent Publication 87/05297, Johnston et al., published Sep. 11, 1987, incorporated herein by reference. Such salts are made by methods known to one of ordinary skill in the art. It is recognized that the skilled artisan may prefer one salt over another for improved solubility, stability, formulation ease, price and the like. Determination and optimization of such salts is within the purview of the skilled artisan's practice. Preferred cations include the alkali metals (such as sodium and potassium), and alkaline earth metals (such as magnesium and calcium) and organic cations, such as trimethylammonium, tetrabutylammonium, etc. Preferred anions include halides (such as chloride), sulfonates, carboxylates, phosphates, and the like. Clearly contemplated in such salts are addition salts that may provide an optical center where once there was none. For example, a chiral tartrate salt may be prepared from the compounds of the invention. This definition includes such chiral salts.

'Phenyl' is a six-membered monocyclic aromatic ring that may or may not be substituted with from 1 to 5 substituents. The substituents may be located at the ortho, meta or para position on the phenyl ring, or any combination thereof. Preferred phenyl substituents include: halo, cyano, lower alkyl, heteroalkyl, haloalkyl, phenyl, phenoxy or any combination thereof. More preferred substituents on the phenyl ring include halo and haloalkyl. The most preferred substituent is halo.

The terms 'polycyclyl' and 'polycyclic group' refer to two or more rings (e.g., cycloalkyls, cycloalkenyls, heteroaryls, aryls and/or heterocyclyls) in which two or more member atoms of one ring are member atoms of a second ring. Rings that are joined through non-adjacent atoms are termed 'bridged' rings, and rings that are joined through adjacent atoms are 'fused rings'.

The term 'small organic molecule' refers to an organic compound of less than about 2500 amu, preferably less than 1500 amu. The term encompasses most pharmaceuticals that are not proteins or nucleic acids.

The term 'sulfhydryl' means —SH, and the term 'sulfonyl' means —$SO_2$—.

A 'substitution' or 'substituent' on a small organic molecule generally refers to a position on a multi-valent atom bound to a moiety other than hydrogen, e.g., a position on a chain or ring exclusive of the member atoms of the chain or ring. Such moieties include those defined herein and others as are known in the art, for example, halogen, alkyl, alkenyl, alkynyl, azide, haloalkyl, hydroxyl, carbonyl (such as carboxyl, alkoxycarbonyl, formyl, ketone, or acyl), thiocarbonyl (such as thioester, thioacetate, or thioformate), alkoxyl, phosphoryl, phosphonate, phosphinate, amine, amide, amidine, imine, cyano, nitro, azido, sulfhydryl, alkylthio, sulfate, sulfonate, sulfamoyl, sulfonamido, sulfonyl, silyl, ether, cycloalkyl, heterocyclyl, heteroalkyl, heteroalkenyl, and heteroalkynyl, heteroaralkyl, aralkyl, aryl or heteroaryl. It will be understood by those skilled in the art that certain substituents, such as aryl, heteroaryl, polycyclyl, alkoxy, alkylamino, alkyl, cycloalkyl, heterocyclyl, alkenyl, alkynyl, heteroalkyl, heteroalkenyl, and heteroalkynyl, can themselves be substituted, if appropriate. This invention is not intended to be limited in any manner by the permissible substituents of organic compounds. It will be understood that 'substitution' or 'substituted with' includes the implicit proviso that such substitution is in accordance with permitted valence of the substituted atom and the substituent, and that the substitution results in a stable compound, e.g., which does not spontaneously undergo transformation such as by rearrangement, cyclization, elimination, hydrolysis, etc.

As used herein, the definition of each expression, e.g., alkyl, m, n, etc., when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl, and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The phrase 'protecting group' as used herein means temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991; and Kocienski, P. J. *Protecting Groups*, Georg Thieme Verlag: New York, 1994).

The term 'prodrug' is intended to encompass compounds that, under physiological conditions, are converted into the therapeutically active agents of the present invention. A common method for making a prodrug is to include selected moieties, such as esters or ketals, that are hydrolyzed under physiological conditions to reveal the desired molecule. In other embodiments, the prodrug is converted by an enzymatic activity of the host animal.

For purposes of this invention, the chemical elements are identified in accordance with the Periodic Table of the Elements, CAS version, Handbook of Chemistry and Physics, 67th Ed., 1986-87, inside cover. Also for purposes of this invention, the term 'hydrocarbon' is contemplated to include all permissible compounds or moieties having at least one carbon-hydrogen bond. In a broad aspect, the permissible hydrocarbons include acyclic and cyclic, branched and unbranched, carbocyclic and heterocyclic, aromatic and non-aromatic organic compounds which can be substituted or unsubstituted.

Contemplated equivalents of the compounds described above include compounds which otherwise correspond thereto, and which have the same useful properties thereof, wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

III. Exemplary Applications of Methods and Compositions

Therapeutic compositions according to the invention contain a therapeutic agent and a material of the invention, such as a cyclodextrin-based material. The therapeutic agent may be any synthetic or naturally occurring biologically active therapeutic agent including those known in the art. Examples of suitable therapeutic agents include, but are not limited to, antibiotics, steroids, polynucleotides (e.g., genomic DNA, cDNA, mRNA and antisense oligonucleotides), plasmids, proteins, polypeptides, peptide fragments, small molecules (e.g., doxorubicin) and other biologically active macromolecules such as, for example, proteins and enzymes. In certain embodiments, the agent may be associated with a delivery system, e.g., a nucleic acid may be contained in a virus, or an agent may be carried within liposomes or microspheres, and the delivery system is dispersed through the material.

A therapeutic composition of the invention may be prepared by means known in the art. In a preferred embodiment, a material of the invention, such as a cyclodextrin-based material, is mixed with or prepared in the presence of a therapeutic agent, as described above. According to the invention, the material acts as a delivery vehicle for the therapeutic agent. The therapeutic agent (and/or an adjuvant) and material may associate by means recognized by those of skill in the art such as, for example, electrostatic interaction, hydrogen bonding, hydrophobic interaction, formation of inclusion complexes with the inclusion hosts, or covalent attachment to the polymer, preferably by a reversible attachment such as an ester or carbonate. In certain embodiments, the therapeutic agent and/or adjuvant may be covalently attached, optionally through a reversible linkage, to a moiety that forms an inclusion complex with the inclusion hosts, e.g., cyclodextrin. The degree of association may be determined by techniques known in the art including, for example, fluorescence studies, DNA mobility studies, light scattering, electron microscopy, and will vary depending upon the therapeutic agent. As a mode of delivery, for example, a therapeutic composition of the invention containing a material of the invention and DNA may be used to aid in transfection, i.e., the uptake of DNA into an animal (e.g., human) cell. (Boussif, O. Proceedings of the National Academy of Sciences, 92:7297-7301(1995); Zanta et al. Bioconjugate Chemistry, 8:839-844 (1997)).

In certain embodiments, a therapeutic composition of the invention is in a form suitable for injection, and in other embodiments, the composition is suitable for topical application. Other modes of administration of a therapeutic composition of the invention include, depending on the state of the therapeutic composition, methods known in the art such as, but not limited to, oral administration, parenteral, intravenous, intranasal, intraocular, intracranial or intraperitoneal injection.

Depending upon the type of therapeutic agent used, a therapeutic composition of the invention may be used in a variety of therapeutic methods (e.g. DNA vaccines, antibiotics, antiviral agents) for the treatment of inherited or acquired disorders such as, for example, cystic fibrosis, Gaucher's disease, muscular dystrophy, AIDS, cancers (e.g., multiple myeloma, leukemia, melanoma, and ovarian carcinoma), cardiovascular conditions (e.g., progressive heart failure, restenosis, and hemophilia), and neurological conditions (e.g., brain trauma). In other embodiments, subject compositions can be used in the treatment of wounds, such as incisions, diabetic ulcers, bedsores, lacerations, burns, etc.

The therapeutic agent may range from a nucleic acid (such as a vector, an RNAi construct, or an antisense oligonucleotide) or protein to a small organic molecule. In certain embodiments, the agent is an anti-cancer (such as camptothecin or related derivatives), anti-fungal, anti-bacterial, anti-mycotic, or anti-viral therapeutic. In certain embodiments, the agent is a receptor agonist. In certain embodiments, the agent is a receptor antagonist. In certain embodiments, the therapeutic agent is a protease inhibitor. Furthermore, a polymer of the present invention may contain one kind of therapeutic agent, or may contain more than one kind of therapeutic agent. For instance, two or more different cancer drugs, or a cancer drug and an immunosuppressant, or an antibiotic and an anti-inflammatory agent may be included in the composition.

Depending upon the type of therapeutic agent used, a therapeutic composition of the invention may be used in a variety of therapeutic methods (e.g. DNA vaccines, antibiotics, antiviral agents) for the treatment of inherited or acquired disorders such as, for example, cystic fibrosis, Gaucher's disease, muscular dystrophy, AIDS, cancers (e.g., multiple myeloma, leukemia, melanoma, and ovarian carcinoma), cardiovascular conditions (e.g., progressive heart failure, restenosis, and hemophilia), and neurological conditions (e.g., brain trauma).

In certain particular embodiments, compositions of the invention may be used to treat wounds (i.e., to promote wound healing. Although the matrix alone may be useful as a wound sealant, such compositions may include, for example, PDGF-B or an expression vector for producing PDGF-B in a target cell, stimulators of cell proliferation or differentiation, stem cells or progenitor cells, and/or other compounds known to be effective in promoting healing, inhibiting infection, etc.

In other embodiments, compositions of the invention may be used in the treatment of cancer. Such compositions may include a chemotherapeutic agent, an angiogenesis-inhibiting agent, a cell proliferation inhibitor, a radiosensitizer, and/or any other agent useful in the treatment of cancer.

For example, compounds that may be formulated in a subject composition for the treatment of cancer include: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic agents may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epipidophyllotoxins (teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylamelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; chromatin disruptors.

According to the invention, a method of treatment administers a therapeutically effective amount of a therapeutic composition of the invention. A therapeutically effective amount, as recognized by those of skill in the art, will be determined on a case by case basis. Factors to be considered include, but are not limited to, the disorder to be treated and the physical characteristics of the one suffering from the disorder.

Another embodiment of the invention is a composition containing at least one biologically active compound having agricultural utility and a linear cyclodextrin-modified polymer or a linear oxidized cyclodextrin-modified polymer of the invention. The agriculturally biologically active compounds include those known in the art. For example, suitable agriculturally biologically active compounds include, but are not limited to, fungicides, herbicides, insecticides, and mildewcides.

IV. Exemplary Compositions

In certain embodiments, the underlying polymers are linear cyclodextrin-containing polymers, e.g., the polymer backbone includes cyclodextrin moieties. For example, the polymer may be a water-soluble, linear cyclodextrin polymer produced by providing at least one cyclodextrin derivative modified to bear one reactive site at each of exactly two positions, and reacting the cyclodextrin derivative with a linker having exactly two reactive moieties capable of forming a covalent bond with the reactive sites under polymerization conditions that promote reaction of the reactive sites with the reactive moieties to form covalent bonds between the linker and the cyclodextrin derivative, whereby a linear polymer comprising alternating units of cyclodextrin derivatives and linkers is produced. A variety of suitable polymers are described in U.S. Patent Applications 20020151523 and 10/656,838. Alternatively the polymer may be a water-soluble, linear cyclodextrin polymer having a linear polymer backbone, which polymer comprises a plurality of substituted or unsubstituted cyclodextrin moieties and linker moieties in the linear polymer backbone, wherein each of the cyclodextrin moieties, other than a cyclodextrin moiety at the terminus of a polymer chain, is attached to two of said linker moieties, each linker moiety covalently linking two cyclodextrin moieties. In yet another embodiment, the polymer is a water-soluble, linear cyclodextrin polymer comprising a plurality of cyclodextrin moieties covalently linked together by a plurality of linker moieties, wherein each cyclodextrin moiety, other than a cyclodextrin moiety at the terminus of a polymer chain, is attached to two linker moieties to form a linear cyclodextrin polymer.

The linker group(s) may be an alkylene chain, a polyethylene glycol (PEG) chain, polysuccinic anhydride, poly-L-glutamic acid, poly(ethyleneimine), an oligosaccharide, an amino acid chain, or any other suitable linkage. In certain embodiments, the linker group itself can be stable under physiological conditions, such as an alkylene chain, or it can be cleavable under physiological conditions, such as by an enzyme (e.g., the linkage contains a peptide sequence that is a substrate for a peptidase), or by hydrolysis (e.g., the linkage contains a hydrolyzable group, such as an ester or thioester). The linker groups can be biologically inactive, such as a PEG, polyglycolic acid, or polylactic acid chain, or can be biologically active, such as an oligo- or polypeptide that, when cleaved from the moieties, binds a receptor, deactivates an enzyme, etc. Various oligomeric linker groups that are biologically compatible and/or bioerodible are known in the art, and the selection of the linkage may influence the ultimate properties of the material, such as whether it is durable when implanted, whether it gradually deforms or shrinks after implantation, or whether it gradually degrades and is absorbed by the body. The linker group may be attached to the moieties by any suitable bond or functional group, including carbon-carbon bonds, esters, ethers, amides, amines, carbonates, carbamates, sulfonamides, etc.

In exemplary embodiments, the cyclodextrin polymers used for forming the material are copolymers of cyclodextrin and polyethylene glycol (PEG). Such polymers can be prepared by techniques well known in the art, such as the reaction exemplified by the following equation:

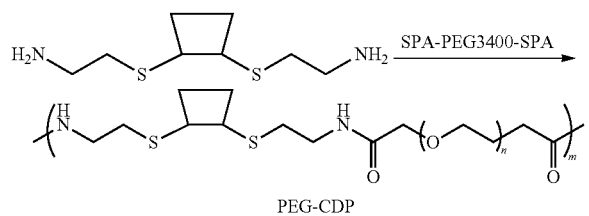

PEG-CDP wherein the trapezoid represents a cyclodextrin moiety, as described in greater detail below, and n represents an integer from 1 to 20, preferably from 2 to 12. The polymers may be modified, e.g., by covalent attachment of therapeutic moieties, e.g., through a linker that is cleavable under physiological conditions.

In such polymers, cyclodextrin moieties may represent at least 2% of the weight of the copolymer, preferably at least 5% or 10%, or even as much as 20%, 40%, 50%, 60%, 80%, or even 90% of the weight of the copolymer.

In certain embodiments, the cyclodextrin polymers used for forming the material have a structure of the formula:

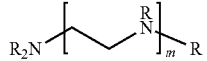

wherein R represents, independently for each occurrence, H, lower alkyl, a cyclodextrin moiety, or

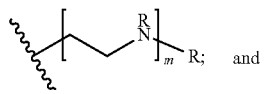

m, independently for each occurrence, represents an integer from 2-10,000, preferably from 10 to 5,000, or from 100 to 1,000. Suitable polymers of this type are discussed at greater length in U.S. patent application Ser. No. 10/372,723 and PCT Application WO 03/072637.

In certain embodiments, R represents a cyclodextrin moiety for at least about 1%, more preferably at least about 3%, and up to about 5%, 10%, 20%, 35%, or even 50%, of the nitrogen atoms that would be primary amines (i.e., bearing two occurrences of R that represent H) but for the cyclodextrin moieties.

In certain embodiments, the cyclodextrin moieties make up at least about 2%, 3%, or 4% by weight, up to 5%, 7%, or even 10% of the cyclodextrin-modified polymer by weight.

In certain embodiments, at least about 2%, 3%, or 4% by weight, up to 5%, 7%, or even 10% of the ethylenimine subunits in the polymer are modified with a cyclodextrin moiety.

Copolymers of poly(ethylenimine) that bear nucleophilic amino substituents susceptible to derivatization with cyclodextrin moieties can also be used to prepare cyclodextrin-modified polymers within the scope of the present invention.

Exemplary cyclodextrin moieties include cyclic structures consisting essentially of from 6 to 9 saccharide moieties, such as cyclodextrin and oxidized cyclodextrin. A cyclodextrin moiety optionally comprises a linker moiety that forms a covalent linkage between the cyclic structure and the polymer backbone, preferably having from 1 to 20 atoms in the chain, such as alkyl chains, including dicarboxylic acid derivatives (such as glutaric acid derivatives, succinic acid derivatives, and the like), and heteroalkyl chains, such as oligoethylene glycol chains. Cyclodextrin moieties may further include one or more carbohydrate moieties, preferably simple carbohydrate moieties such as galactose, attached to the cyclic core, either directly (i.e., via a carbohydrate linkage) or through a linker group.

Cyclodextrins are cyclic polysaccharides containing naturally occurring D-(+)-glucopyranose units in an α-(1,4) linkage. The most common cyclodextrins are alpha ((α)-cyclodextrins, beta (β)-cyclodextrins and gamma (γ)-cyclodextrins which contain, respectively, six, seven, or eight glucopyranose units. Structurally, the cyclic nature of a cyclodextrin forms a torus or donut-like shape having an inner apolar or hydrophobic cavity, the secondary hydroxyl groups situated on one side of the cyclodextrin torus and the primary hydroxyl groups situated on the other. Thus, using (β)-cyclodextrin as an example, a cyclodextrin is often represented schematically as follows.

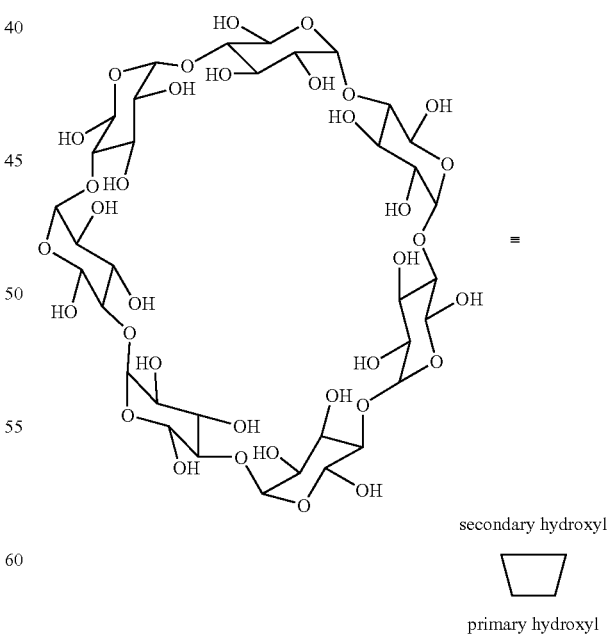

The side on which the secondary hydroxyl groups are located has a wider diameter than the side on which the primary hydroxyl groups are located. The hydrophobic nature of the cyclodextrin inner cavity allows for the inclusion of a variety of compounds. (Comprehensive Supramolecular Chemistry, Volume 3, J. L. Atwood et al., eds., Pergamon Press (1996); T. Cserhati, Analytical Biochemistry, 225:328-332(1995); Husain et al., Applied Spectroscopy, 46:652-658 (1992); FR 2 665 169). Additional methods for modifying polymers are disclosed in Suh, J. and Noh, Y., *Bioorg. Med. Chem. Lett.* 1998, 8, 1327-1330.

Cyclodextrins have been used as a delivery vehicle of various therapeutic compounds by forming inclusion complexes with various drugs that can fit into the hydrophobic cavity of the cyclodextrin or by forming non-covalent association complexes with other biologically active molecules such as oligonucleotides and derivatives thereof. For example, see U.S. Pat. Nos. 4,727,064, 5,608,015, 5,276,088, and 5,691,316. Various cyclodextrin-containing polymers and methods of their preparation are also known in the art. *Comprehensive Supramolecular Chemistry*, Volume 3, J. L. Atwood et al., eds., Pergamon Press (1996). Cyclodextrin polymers have been produced by linking or cross-linking cyclodextrins or mixtures of cyclodextrins and other carbohydrates with polymerizing agents, e.g. epichlorhydrin, diisocynanates, diepoxides (Insoluble cyclodextrin polymer beads, Chem. Abstr. No. 222444m, 102: 94; Zsadon and Fenyvesi, 1st. Int. Symp. on Cyclodextrins, J. Szejtli, ed., D. Reidel Publishing Co., Boston, pp. 327-336; Fenyvesi et al., 1979, Ann. Univ. Budapest, Section Chim. 15: 13 22; and Wiedenhof et al., 1969, Die Stirke 21: 119-123). These polymerizing agents are capable of reacting with the primary and secondary hydroxy groups on carbons 6, 2, and 3. Cyclodextrin-modified polymer carriers can be coupled to biorecognition molecules for targeting the delivery of drugs to their site of action. See also U.S. Pat. Nos. 6,180,739, 5,981,740, 5,929,131, 5,910, 551, and 5,792,821 (disclosing polymerizable cyclodextrin derivatives), U.S. Pat. No. 6,048,736 (discussing drug delivery using cyclodextrin polymers), (disclosing polymerizable cyclodextrin derivatives), U.S. Pat. Nos. 5,856,416 and 5,593,768 (disclosing monomers and polymers that bear cyclodextrin moieties), U.S. Pat. No. 5,608,015 (disclosing methods for preparing polymerizable cyclodextrin derivatives), and U.S. Pat. No. 5,516,766 (describing uses for cyclodextrin polymers).

The crosslinking molecules generally comprise two or more moieties that form inclusion complexes with cyclodextrin or another inclusion host, the moieties being covalently linked by a chain of atoms that allows the moieties to be spaced from 0.5 to 50 nm apart, preferably 1 to 30 nm apart. The moieties can be selected from any molecules that form inclusion complexes with an inclusion host such as cyclodextrin, e.g., phenyl rings, adamantane polycycles, cholesterol, naphthol derivatives, etc. See, for example, Szejtli, *Cyclodextrins and Their Inclusion Complexes*; Akademiai Klado, Budapest, 1982; and Bender et al., *Cyclodextrin Chemistry*, Springer-Verlag, Berlin, 1978. Cyclodextrins are able to form inclusion complexes with an array of organic molecules including, for example, drugs, pesticides, and herbicides. See, Tenjarla et al., *J. Pharm. Sci.,* 87: 425429 (1998); Zughul et al., *Pharm. Dev. Technol.,* 3: 43-53 (1998); and Albers et al., *Crit. Rev. Ther. Drug Carrier Syst.,* 12: 311-337 (1995). The moieties in a crosslinking molecule may be the same or different, and different crosslinking molecules may be used simultaneously in a single material.

The covalent linkage between the moieties may be any suitable linkage, such as an alkylene chain, a polyethylene glycol (PEG) chain, poly(ethyleneimine), an oligosaccharide, an amino acid chain, or any other suitable linkage. The linkage can be stable under physiological conditions, such as an alkylene chain, or it can be cleavable under physiological conditions, such as by an enzyme (e.g., the linkage contains a peptide sequence that is a substrate for a peptidase), or by hydrolysis (e.g., the linkage contains a hydrolyzable group, such as an ester or thioester). The linkage can be biologically inactive, such as a PEG, polyglycolic acid, or polylactic acid chain, or can be biologically active, such as an oligo- or polypeptide that, when cleaved from the moieties, binds a receptor, deactivates an enzyme, etc. Various oligomeric linkages that are biologically compatible and/or bioerodible are known in the art, and the selection of the linkage may influence the ultimate properties of the material, such as whether it is durable when implanted, whether it gradually deforms or shrinks after implantation, or whether it gradually degrades and is absorbed by the body. The linkage may be attached to the moieties by any suitable bond or functional group, including carbon-carbon bonds, esters, ethers, amides, amines, carbonates, carbamates, sulfonamides, etc.

In one exemplary embodiment, the crosslinking molecule comprises moieties that are biologically active drugs joined by a linkage that is biologically active and hydrolyzes under physiological conditions. After implantation, the linkages are gradually cleaved, releasing the active drugs and partially degrading the structure of the material. If the polymer supporting the cyclodextrin is also biodegradable, the material will gradually disintegrate, slowly releasing the biologically active drugs complexed within it. In such embodiments, additional pharmaceutical agents may, but need not be, included in the material to obtain a therapeutic effect.

Materials of the invention may further comprise one or more biologically active agents. Such agents may also form inclusion complexes with cyclodextrin, or may be merely dispersed through the material. Exemplary agents include nucleic acids, viruses, polypeptides, polyplexes, pharmaceuticals, small organic molecules, antibodies, or any other therapeutic agents.

In certain embodiments, a subject composition comprises an RNAi construct, e.g., for using RNA interference (RNAi) to effect knockdown of a target gene. RNAi constructs comprise double stranded RNA that can specifically block expression of a target gene, and are suitable for delivery using the subject compositions. RNAi provides a useful method of inhibiting gene expression in vitro or in vivo. RNAi constructs can comprise either long stretches of dsRNA identical or substantially identical to the target nucleic acid sequence or short stretches of dsRNA identical to substantially identical to only a region of the target nucleic acid sequence.

Optionally, the RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

The subject RNAi constructs can be "small interfering RNAs" or "siRNAs." These nucleic acids are around 19-30 nucleotides in length, and even more preferably 21-23 nucleotides in length. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group. In certain embodiments, the siRNA constructs can be generated by processing of longer double-stranded RNAs, for example, in the presence of the enzyme dicer. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 23 nucleotides. The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of an nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis. Methods of chemically modifying RNA molecules can be adapted for modifying RNAi constructs (see, e.g., Heidenreich et al. (1997) *Nucleic Acids Res,* 25:776-780; Wilson et al. (1994) *J Mol Recog* 7:89-98; Chen et al. (1995) *Nucleic Acids Res* 23:2661-2668; Hirschbein et al. (1997) *Antisense Nucleic Acid Drug Dev* 7:55-61). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration).

In some cases, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

The RNAi construct can also be in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

Alternatively, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., *Genes Dev,* 2002, 16:948-58; McCaffrey et al., *Nature,* 2002, 418:38-9; McManus et al., *RNA,* 2002, 8:842-50; Yu et al., *Proc Natl Acad Sci USA,* 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

PCT application WO 01/77350 describes an exemplary vector for bidirectional transcription of a transgene to yield both sense and antisense RNA transcripts of the same transgene in a eukaryotic cell. Accordingly, in certain embodiments, a subject composition includes, for ultimate delivery, a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

V. Business Methods

Other aspects of the invention provides for certain methods of doing business. In particular, practicing the methods of the invention may enable novel therapeutic compositions and improved formulations thereof. This technical step, when combined with one or more additional steps, provides for novel approaches to conducting a pharmaceutical, or preferably a life-science business. For example, a therapeutic composition prepared by the method of the invention may be tested for efficacy as therapeutics in a variety of disease models, the potential therapeutic compositions then tested for toxicity and other safety-profiling before formulating, packaging and subsequently marketing the resulting formulation for the treatment of disease. Alternatively, the rights to develop and market such formulations or to conduct such steps may be licensed to a third party for consideration.

Accordingly, in certain embodiments, the present invention provides a method for conducting a pharmaceutical business, comprising:

a. manufacturing a formulation or kit including a pharmaceutical composition of any of the compositions disclosed herein; and b. marketing to healthcare providers the benefits of using the formulation or kit in the treatment of a disease or disorder.

In other embodiments, the present invention discloses a method for conducting a pharmaceutical business, comprising:

a. providing a distribution network for selling a pharmaceutical composition of any of the compositions disclosed herein; and b. providing instruction material to patients or physicians for using the preparation in the treatment of a disease or disorder.

In certain embodiments, the present invention provides a method for conducting a pharmaceutical business, comprising:

a. determining an appropriate formulation and dosage of a pharmaceutical composition of any of the compositions disclosed herein;

b. conducting therapeutic profiling of formulations identified in step (a), for efficacy and toxicity in animals; and c. providing a distribution network for selling a preparation or preparations identified in step (b) as having an acceptable therapeutic profile.

An additional step of the embodiment comprises providing a sales group for marketing the preparation to healthcare providers.

In still other embodiments, the present invention provides a method for conducting a pharmaceutical business, comprising:

a. determining an appropriate formulation and dosage of a pharmaceutical composition of any of the compositions disclosed herein; and b. licensing, to a third party, the rights for further development and sale of the formulation.

EXEMPLIFICATION

The invention now being generally described, it will be more readily understood by reference to the following examples, which are included merely for purposes of illustration of certain aspects and embodiments of the present invention, and are not intended to limit the invention.

Example 1

Synthesis of Polyethylenimine (PEI)-Cyclodextrin Conjugates
(Suh et al. 1992, *J. Am. Chem. Soc.* 114 7916-7917)

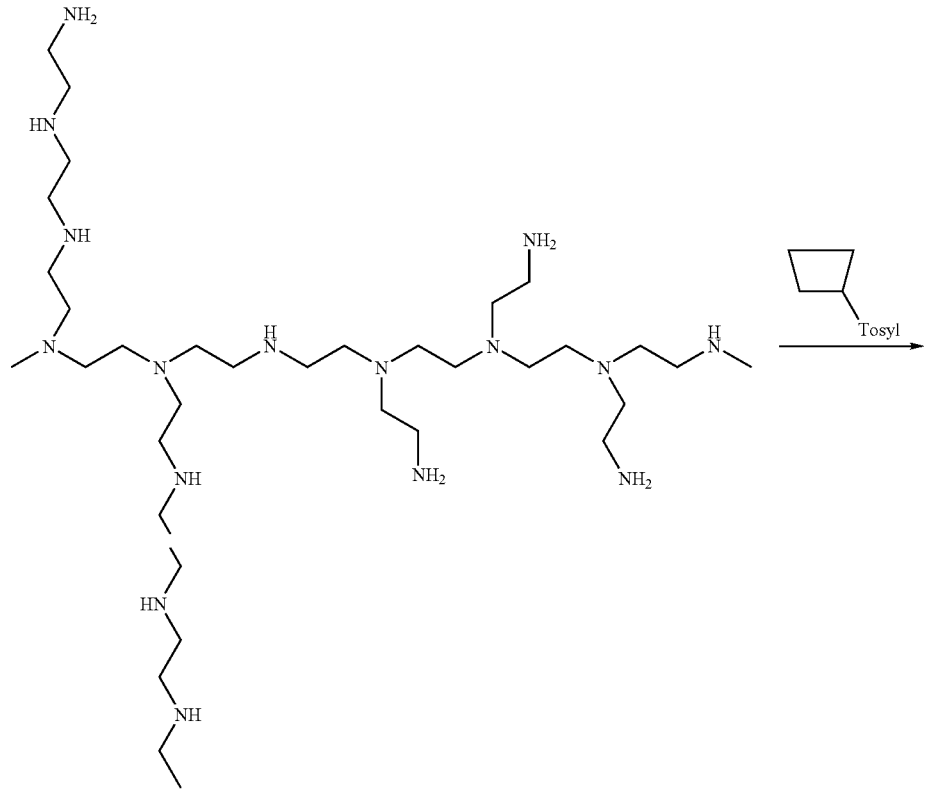

-continued

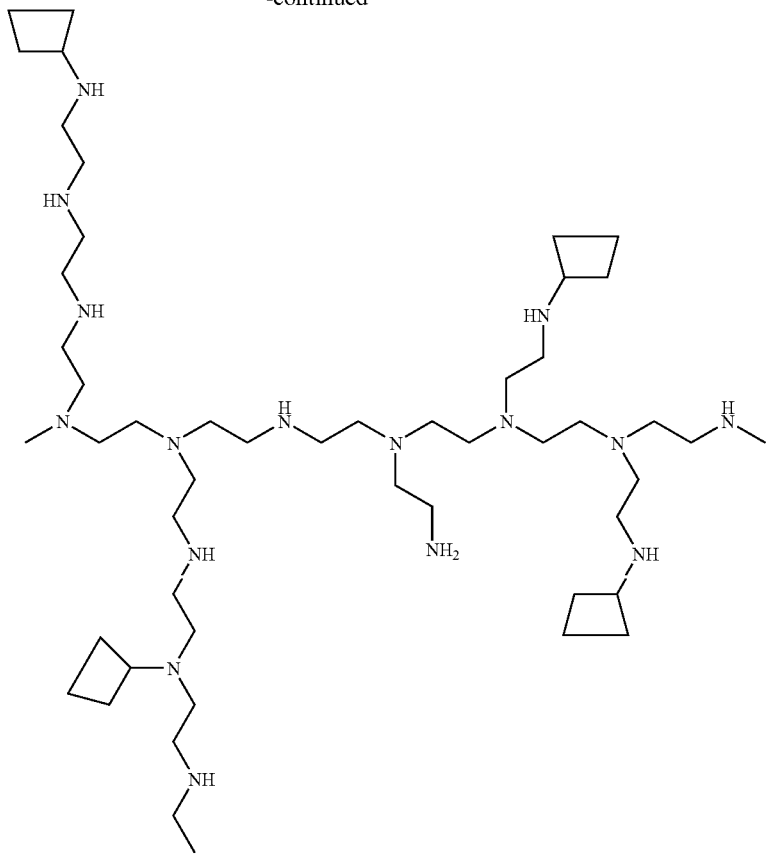

Branched PEI (60 mg, Aldrich Mw 25,000) was dissolved in DMSO (4 mL) and degassed water (6 mL) solvent mixture. Cyclodextrin monotosylate (928 mg, Cyclodextrin Technologies Development, Inc.) was added to the solution under argon. The cloudy solution turned clear after the mixture was stirred at 70° C. for about 1 hour. The solution turned slightly yellow after 48 hours at this temperature under argon. The solution was transferred to a Spectra/Por MWCO 25,000 membrane and dialyzed against water for 6 days. Water was then removed by lyophilization. A white powder was obtained (134 mg) after the solution was lyophilized. Cyclodextrin/PEI ratio was calculated based on the proton integration of $^1$H NMR.

Example 2

Synthesis of hydrolysable Polyethylenimine (PEI)-Cyclodextrin Conjugates

Ahn et al. 2002 *Journal of Controlled Release* 80, 273-282

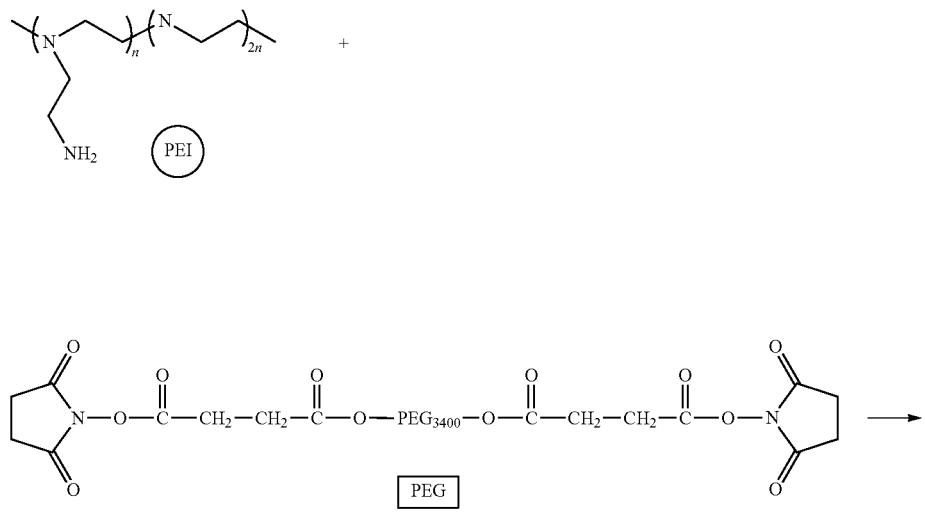

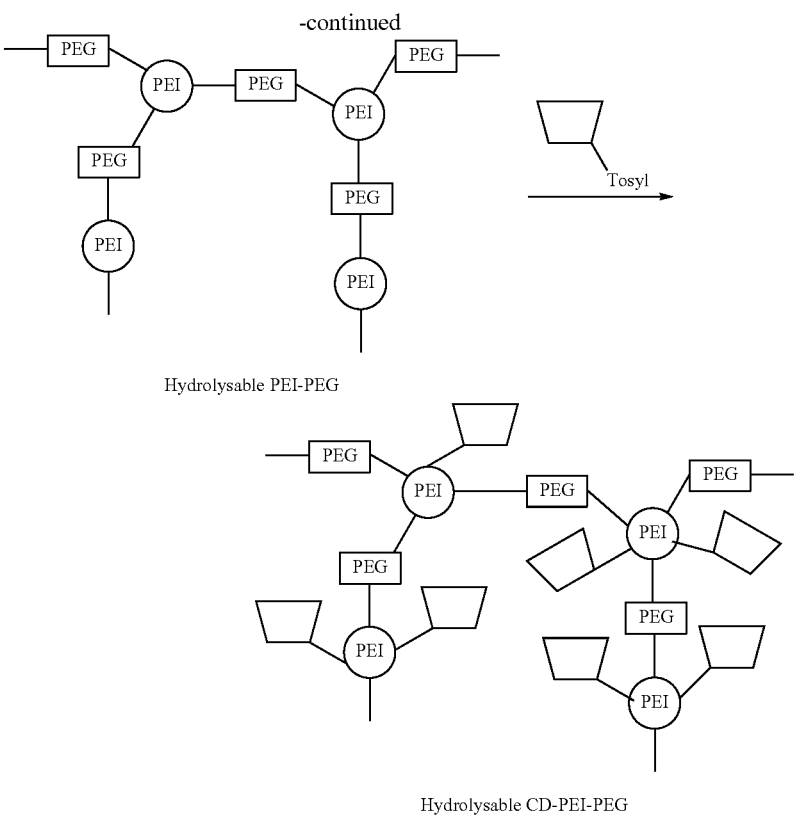

Hydrolysable PEI-PEG

Hydrolysable CD-PEI-PEG

The hydrolysable PEI-PEG is synthesized as described in Ahn et al. 2002 *Journal of Controlled Release* 80, 273-282 reference. The resulting hydrolysable PEI polymer is dissolved in DMSO (4 mL) and degassed water (6 mL) solvent mixture. Cyclodextrin monotosylate (Cyclodextrin Technologies Development, Inc.) is added to the solution under argon. The reaction mixture is then precipitated into cold diethyl ether and the product is dried under vacuum overnight. Cyclodextrin/PEI ratio is calculated based on the proton integration of $^1$H NMR.

Example 3

Synthesis of Linear Cyclodextrin-Based Polyethylene Glycol Polymers (CD-PEG)

CD-PEG polymers were prepared by the polymerization of a difunctionalized β-cyclodextrin monomer (A) with a difunctionalized polyethylene glycol comonomer (B) to give an ABAB product. The synthesis procedure involves first the preparation of the difunctionalized β-cyclodextrin (6A,6D-dideoxy-6A,6D-di(2-aminoethanethio)-β-cyclodextrin (denoted dicysteamine-β-cyclodextrin) according to literature procedures (Gonzalez et al. 1999 *Bioconiugate Chem.* 10:1068-1074; and Hwang et al. 2001 *Bioconiugate Chem.* 12(2):280-290). The polymerization step was carried using commercially available difunctionalized polyethylene glycol. Three methods were investigated.

Method I: Using Diacid-Polyethylene Glycol

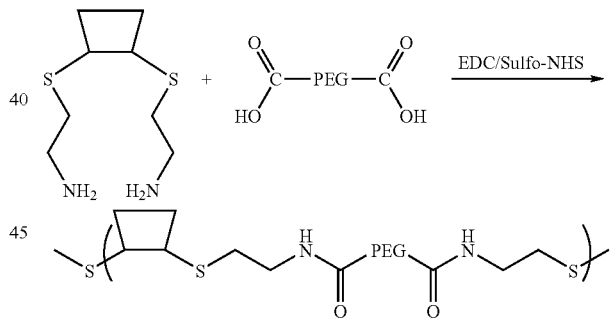

Synthesis:

Diacid-PEGs with various molecular weights (Mw=250, 600, 3000, 6000) were purchased from Fluka, Milwaukee, Wis. In a typical experiment, $PEG_{600}$-$(COOH)_2$ (0.096 g, 0.16 mmol) was dissolved in 1 mL of a 25 mM MES buffer (2-(N-morpholino)ethanesulfonic acid) at pH 6.5. Dicysteamine-β-cyclodextrin (0.2 g, 0.16 mmol) dissolved in 2 mL of a 25 mM MES buffer (pH 6.5) was added. Then, 1-(3-dimethylaminopropyl)-3-ethylcarbodiimide hydrochloride (EDC) (0.612 g, 3.2 mmol, Aldrich, Milwaukee, Wis.) and N-Hydroxysulfosuccinimide (Sulfo-NHS) (0.026 g, 0.12 mmol, Pierce, Rockford, Ill.) were added. The resulting solution was allowed to stir overnight at room temperature. The polymer solution was then transferred to a Spectra/Por 7 MWCO 10,000 membrane (Spectrum, Houston, Tex.) and dialyzed against water for 24 h. The solution was then freeze-dried to dryness. This afforded 272 mg of white solid (Yield: 93%).

Characterization: Light Scattering and Molecular Weight Determination

The specific refractive index increment, dn/dc, was measured in Phosphate Buffered Saline 1× (PBS) (Cellgro, Mediatech, Inc, Herndon, Va.) using a Bausch & Lomb ABBE-3L refractive index. Polymer samples were then analyzed on a Hitachi D6000 HPLC system equipped with a ERC-7512 RI detector, a Precision Detectors PD2020/DLS static light scattering detector and an PL aquagel-OH 30 (Polymer Laboratories, Amherst, Mass.) column using Phosphate Buffered Saline 1× as eluant at a 0.7 mL/min flow rate. The dn/dc, the weight average molecular weight Mw, and the polydispersity index Mw/Mn determined for each polymer are reported in the following table.

TABLE 1

Static Light Scattering and Molecular Weight Determination of CD-PEG polymers.

| Polymer | dn/dc | Mw (Da) | Polydispersity |
|---|---|---|---|
| CD-PEG$_{6000}$ | 0.1267 | 21,560 | 1.69 |
| CD-PEG$_{3000}$ | 0.1296 | 10,490 | 1.35 |
| CD-PEG$_{600}$ | 0.1361 | 28,450 | 1.77 |
| CD-PEG$_{250}$ | 0.1359 | 21,150 | 1.06 |

Method II: Using Disuccinimidyl Propionate Polyethylene Glycol

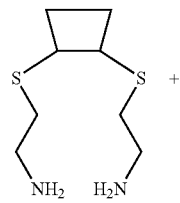

Synthesis:

Disuccinimidyl propionate polyethylene glycol (PEG$_{3400}$-(SPA)$_2$) (1.0854 g, 0.32 mmol, Shearwater Polymers, Inc, Huntsville, Ala.) in solution in 5 mL of DMSO was added to a solution of dicysteamine-β-cyclodextrin (0.4 g, 0.32 mmol) dissolved in 2 mL of DMSO. A viscous solution was immediately formed. The reaction mixture was then allowed to stir overnight at room temperature under argon. Diethylether was added to precipitate the polymer and then poured out with a pipet. The residual ether was evaporated and the polymer was redissolved in water. The resulting solution was then transferred to a 10,000 MWCO Spectra/Por membrane and dialyzed against water for 24 h. The solution was then freeze-dried to dryness. This afforded 1.329 g of white solid (Yield: 95%).

Characterization: Light Scattering and Molecular Weight Determination

This polymer was characterized using the same technique presented above. The dn/dc was calculated to be 0.1316 and the weight average molecular weight Mw was determined to be 184,000 Da with a polydispersity index Mw/Mn of 2.18.

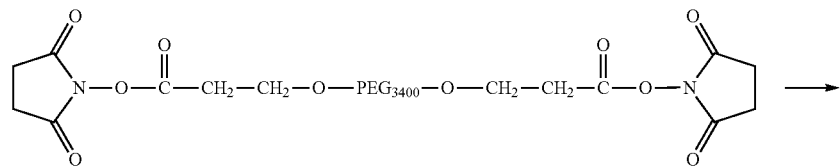

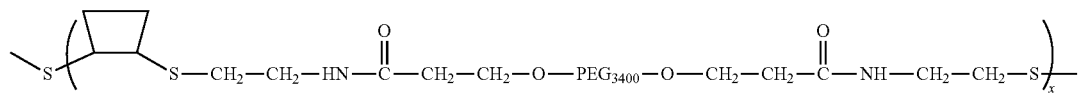

Method III: Using Di-Benzotriazole Carbonate Polyethylene Glycol

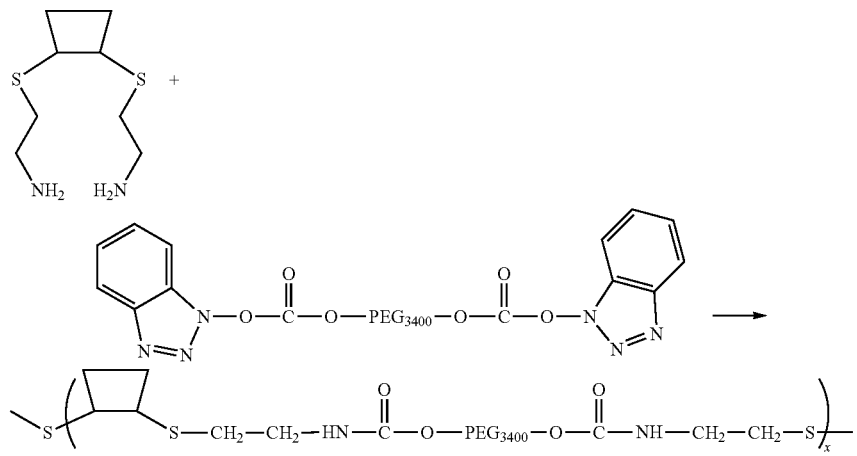

Synthesis:

Di-benzotriazole carbonate polyethylene glycol (PEG$_{3400}$-BTC)$_2$) (1 g, 0.32 mmol, Shearwater Polymers, Inc, Huntsville, Ala.) in solution in 5 mL of DMSO was added to a solution of dicysteamine-β-cyclodextrin (0.4 g, 0.32 mmol) dissolved in 2 mL of DMSO. A viscous solution was immediately formed. The reaction mixture was then allowed to stir overnight at room temperature under argon. Diethyl ether was added to precipitate the polymer and then poured out with a pipette. The residual ether was evaporated and the polymer was redissolved in water. The resulting solution was then transferred to a 10,000 MWCO Spectra/Por membrane and dialyzed against water for 24 h. The solution was then freeze-dried to dryness. This afforded 1.3 g of white solid (Yield: 95%).

Example 4

Molecular weight control of CD-PEG polymers:

propionate polyethylene glycol (PEG$_{3400}$-(SPA)$_2$) (1.565 g, 0.46 mmol, Shearwater Polymers, Inc, Huntsville, Ala.) was then added. To the mixture was added dry DMSO (8 mL). After 10 min stirring, DIEA (176 µL, 1.01 mmol) was added under argon. A portion of polymerization solution (1 mL) was removed at selected times (15 min, 30 min, 60 min, 1 h, 2 h and 5 h). These samples were then transferred to a 10,000 MWCO Spectra/Por membrane and dialyzed against water for 24 h. The solutions were then freeze-dried to dryness. MWs of the resulting solids were determined as described above.

Figure 3:
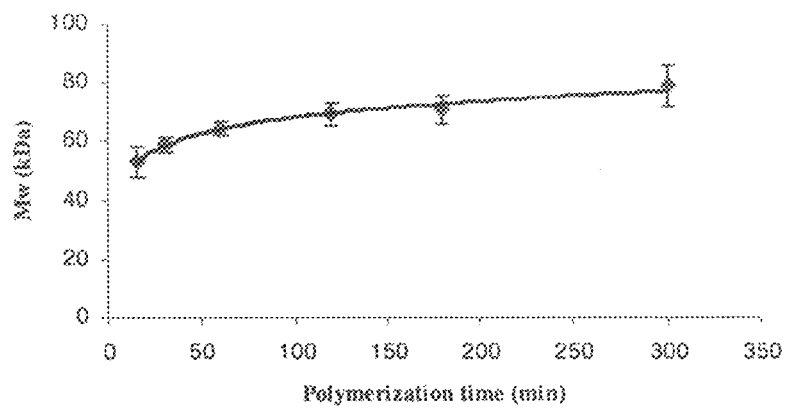
FIG. 3 depicts molecular weights of $CD\text{-}PEG_{3400}$ as a function of polymerization times.
Figure 4:
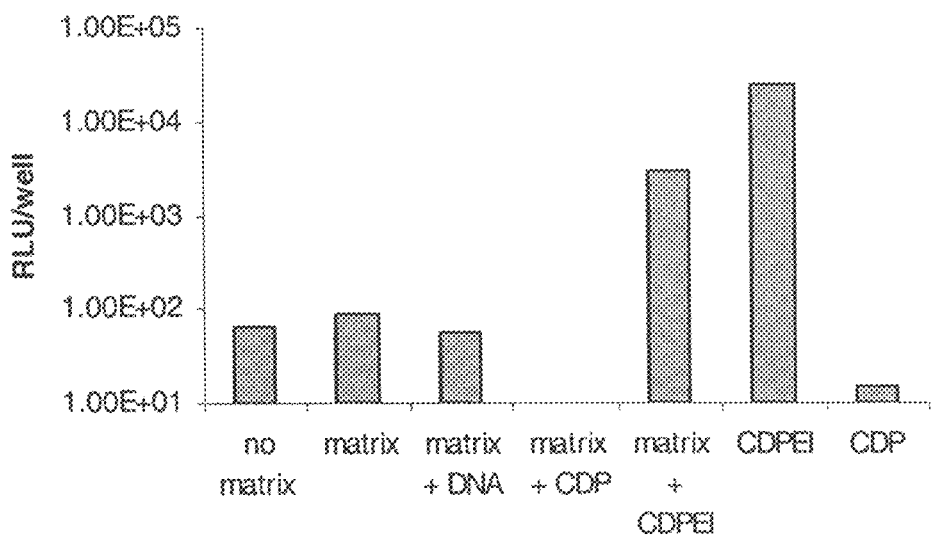
FIG. 4 presents results of transfection experiments.
Figure 6:
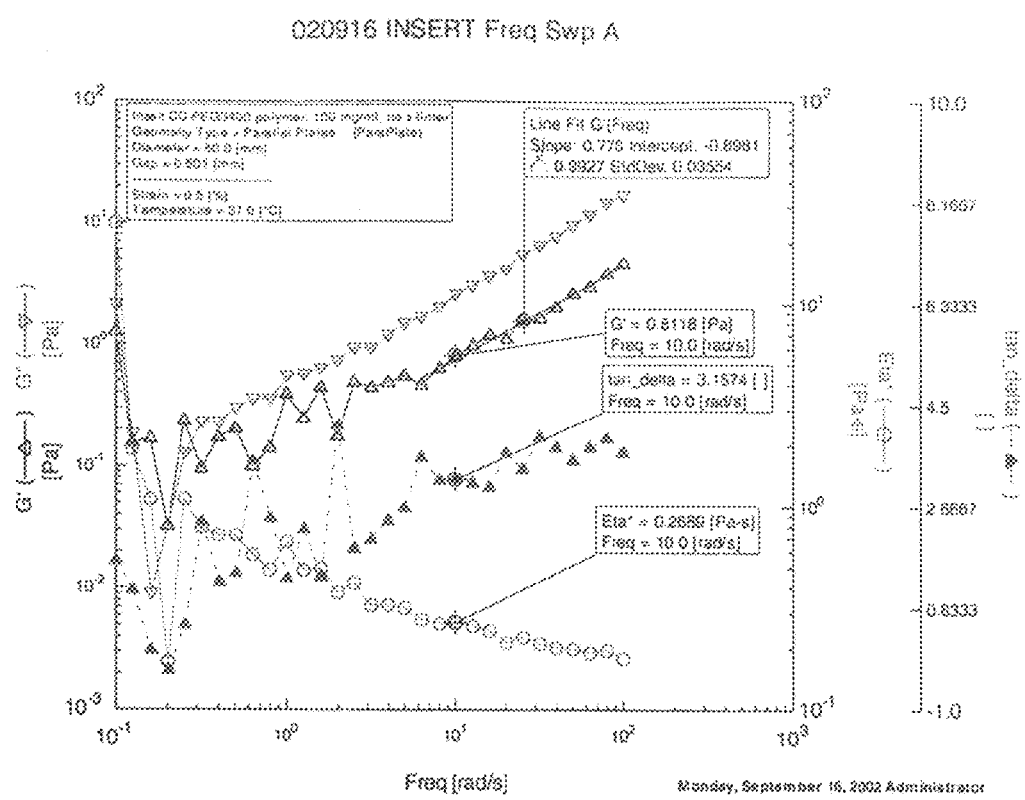
FIG. 6 shows a dynamic frequency sweep of $CD\text{-}PEG_{3400}$ polymer without cross-linking. Concentration was 100 mg/ml in PBS, temperature was 37° C. and strain was 0.5%.

As shown in FIG. 3, the polymer Mw increased to around 80 kDa over a 5 h time course. The polymer Mw can be controlled between 50 to 80 kDa.

Example 5

Synthesis of Hydrolysable Linear Cyclodextrin-Based Polyethylene Glycol Polymers (CD-PEG)

Method I: Using NHS-HBA-CM-PEG$_{400}$-CM-HBA-NHS

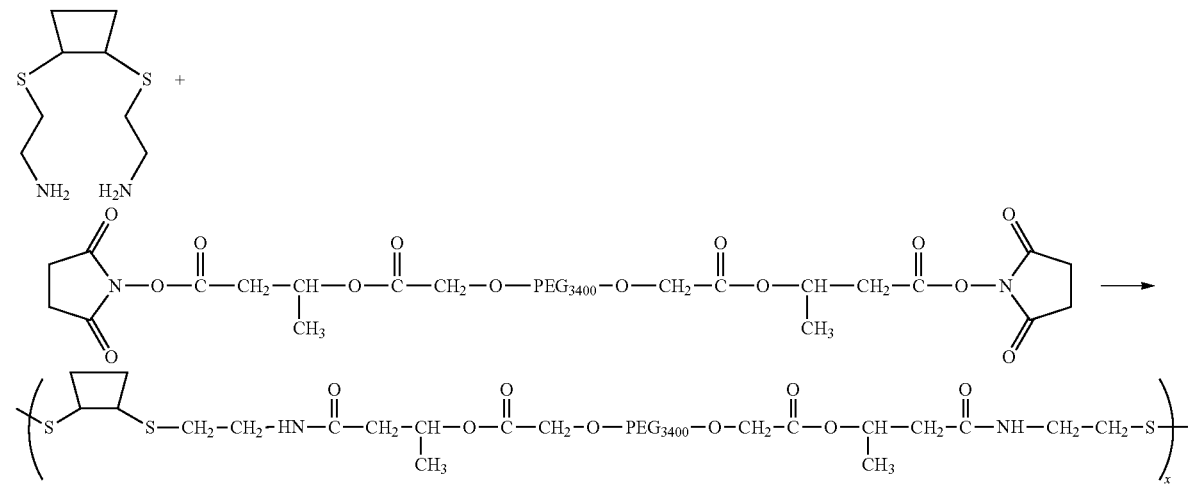

Dicysteamine-β-cyclodextrin.2 HCl (0.577 g, 0.46 mmol) was dried under vacuum at 100° C. for 16 h. Disuccinimidyl NHS-HBA-CM-PEG$_{3400}$-CM-HBA-NHS (0.2 g, 0.06 mmol, Shearwater Polymers, Inc, Huntsville, Ala.) in solution in 1.5 mL of DMSO is added to a solution of dicysteamine-β-cyclodextrin (0.074 g, 0.06 mmol) dissolved in 2 mL of DMSO. The reaction mixture is then allowed to stir overnight at room temperature under argon. The resulting polymer is precipitated with diethylether, filtrated and dried under vacuum.

Method II: Using PEG Succinimidyl Succinate (PEG-(SS)₂

Synthesis:

Ethylene glycol bis[succinimidylsuccinate] (EGS) (0.2 mmol, Pierce, Rockford, Ill.) in solution in 2 mL of DMSO is added to a solution of dicysteamine-β-cyclodextrin (0.2 mmol) dried overnight at 100° C. under vacuum and dissolved in 1.5 mL of DMSO. The reaction mixture is then

Synthesis:

Disuccinimidyl succinate polyethylene glycol (PEG₃₄₀₀-(SS)₂) (SunBio, Inc., 980-5 Kwan-yang Dong, Anyang City, S. Korea) (0.3 mmol) in solution in 5 mL of DMSO is added to a solution of dicysteamine-β-cyclodextrin (0.3 mmol) dissolved in 2 mL of DMSO. The reaction mixture is then allowed to stir overnight at room temperature under argon. The resulting polymer is precipitated with diethylether, filtrated and dried under vacuum.

Example 6

Synthesis of Hydrolysable Linear Cyclodextrin-Based Polymer allowed to stir overnight at room temperature under argon. The resulting mixture is precipitated with Acetone, filtrated and dried under vacuum.

Example 7

Synthesis of Diadamantane Crosslinker: Bis-(2(1-adamantyl)ethyl)phosphate (Zhang et al. 1997, *J. Am. Chem. Soc.* 119(7):1676-1681)

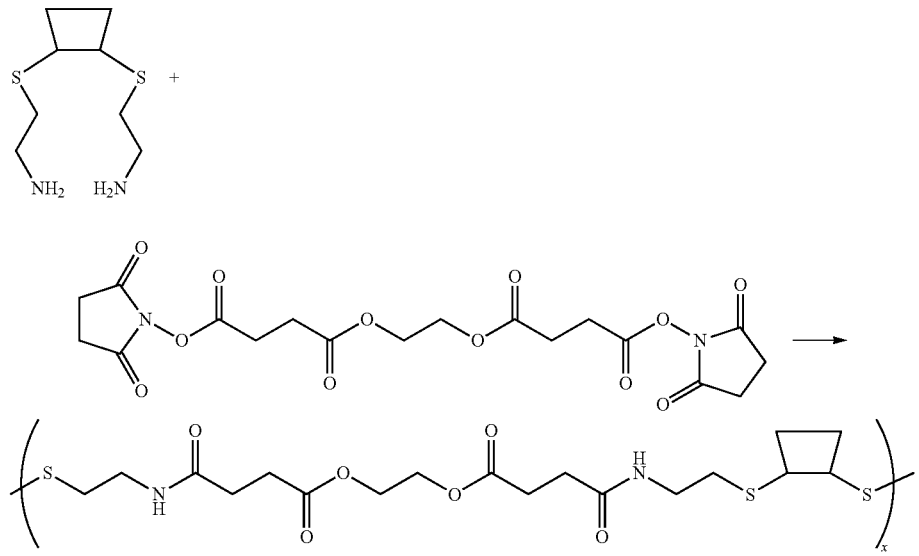

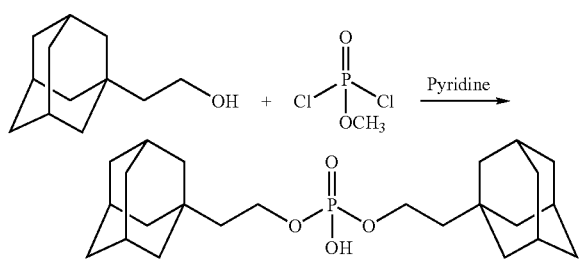

Synthesis:

Anydrous pyridine (10 mL, Aldrich, Milwaukee, Wis.) was cooled in an ice bath and methyl dichlorophosphate (1.488 g, 10 mmol, Aldrich, Milwaukee, Wis.) was added dropwise. The mixture was kept cold for a further 15 min. During this period a precipitate of N-methylpyridinium dichlorophosphate formed. 1-Adamantane ethanol (4.758 g, 26.4 mmol, Aldrich, Milwaukee, Wis.) was added, and the sealed mixture was stirred overnight at room temperature. It was then poured into 10% NaHCO$_3$ (50 mL) and the pyridine was evaporated under vacuum. The slightly yellow solid was dissolved in 1 L of water and extracted with ether (three 150 mL portions). The aqueous phase was acidified with 2 N HCl to pH 1, and then extracted with three 150 mL portions of CHCl$_3$:n-BuOH (7:3). The combined organic layer (ether and CHCl$_3$:n-BuOH) was washed with water and a slightly yellow precipitate was formed in the mixed solvents, at which point the solvents were evaporated under vacuum. A slightly yellow solid was formed and was recrystallized from acetone/hexane. The solid was dried under vacuum, yield 60%.

Characterization:

The product was characterized by $^1$H NMR and $^{13}$C NMR. $^1$H NMR (CDCl$_3$): δ 1.45-1.75 (m, 28H, —CH$_2$—, adamantyl), 1.95 (m, 6H, C—H, adamantyl), 4.07 (q, 4H, —CH$_2$—) and 8.60 (br, 1H, POOH). $^{13}$C NMR (CDCl$_3$, 500 MHz): δ 28.59, 31.77, 37.02, 42.52, 43.96, 44.02, 64.21, 64.26. The product was also characterized by Mass Spectroscopy: Electrospray Ionization: 421 [M−H]$^-$.

Example 8

Synthesis of Hydrolysable Adamantane Crosslinker:

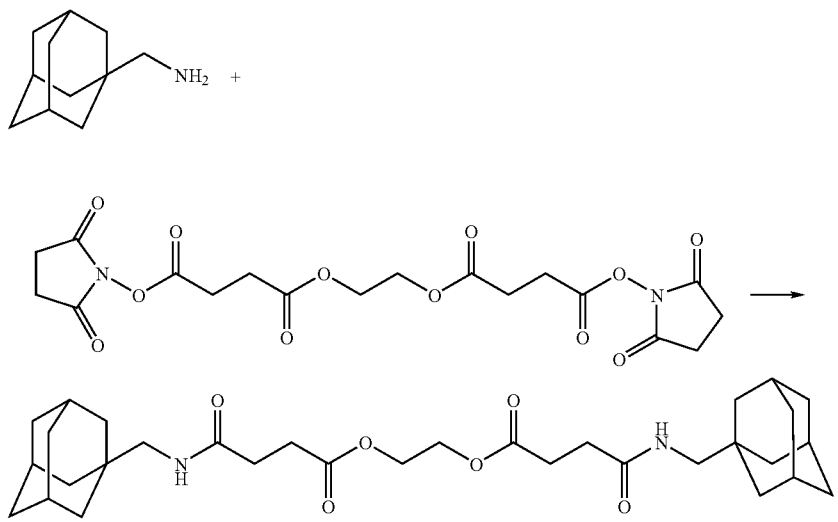

Synthesis:

1-Adamantanemethylamine (0.152 g, 0.92 mmol, Aldrich, Milwaukee, Wis.) was added to Ethylene glycol bis[succinimidylsuccinate] (EGS) (0.2 g, 0.43 mmol, Pierce, Rockford, Ill.) in solution in 10 mL of anhydrous dichloromethane. The resulting solution was stirred for 5 h at room temperature. It was then acidified with 0.1 N HCl and extracted with dichloromethane. The organic phase was dried with MgSO$_4$ and then concentrated to dryness under vacuum. This afforded 0.22 g of solid (yield 90%).

Characterization:

The product was characterized by Mass Spectroscopy: Electrospray Ionization: 557 [M+H]$^+$, 579 [M+Na]$^+$, 1135 [2M+Na]$^+$.

Example 9

Synthesis of Diadamantane Polyethylene Glycol Crosslinker:

Various methods were investigated:

Method I: Using Diacid-Polyethylene Glycol

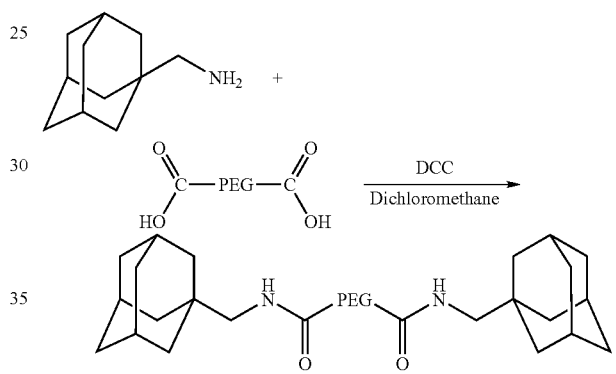

1-Adamantanemethylamine (0.64 mmol, Aldrich, Milwaukee, Wis.) is added to PEG-diacid (0.32 mmol, Fluka, Milwaukee, Wis.) dissolved in dichloromethane. 1,3-Dicyclohexylcarbodiimide (DCC) (3.2 mmol, Aldrich, Milwaukee, Wis.) is added and the resulting solution is stirred overnight at room temperature. The precipitate (dicyclohexylisourea, DCU) is filtered off and the filtrate is washed with 18% HCl. The organic phase is dried with MgSO$_4$ and then concentrated to dryness under vacuum. The resulting solid is redissolved in water in order to precipitate the remaining DCC. DCC is filtered off and the filtrate is freeze-dried.

Method II: Using Disuccinimidyl Propionate Polyethylene Glycol

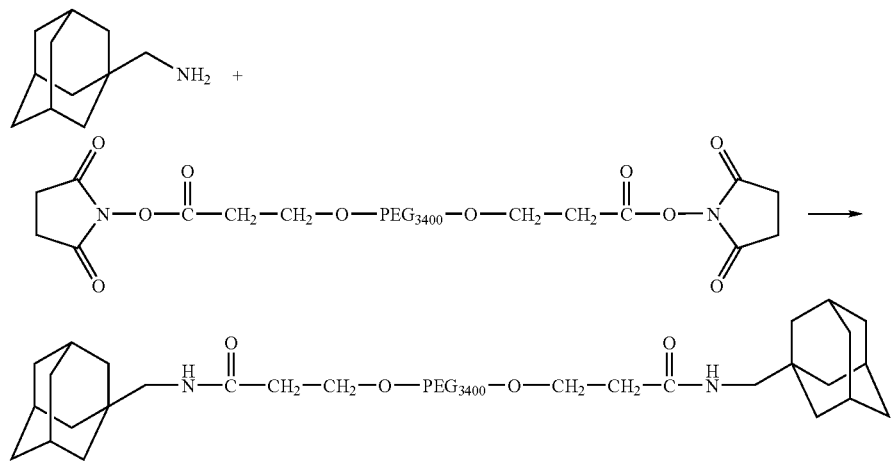

1-Adamantanemethylamine (0.1 g, 0.60 mmol, Aldrich, Milwaukee, Wis.) was added to Disuccinimidyl propionate polyethylene glycol (PEG$_{3400}$-(SPA)$_2$) (1.02 g, 0.30 mmol, Shearwater Polymers, Inc, Huntsville, Ala.) dissolved in 10 mL of dichloromethane. The resulting solution was stirred at room temperature overnight. The solvent was evaporated under vacuum and the residue was dissolved in water and centrifuged to remove excess 1-adamantanemethylamine. The supernatant was then transferred to a 1,000 MWCO Spectra/Por membrane and dialyzed against water for 24 h. The solution was then freeze-dried to dryness. This afforded 0.88 g of solid (yield 84%).

Method III: Using Polyethylene Glycol (Sandier et al. 2000, *Langmuir* 16:1634-1642)

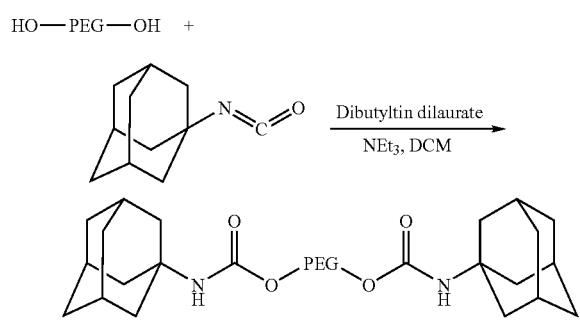

Polyethylene glycol (Mw=1000) (1 g, 1 mmol, Aldrich, Milwaukee, Wis.) was dried by heating under vacuum at 70° C. overnight. 1-Adamantyl isocyanate (0.39 g, 2.2 mmol, Aldrich, Milwaukee, Wis.) was added to the dried polyethylene glycol after its dissolution in anhydrous dichloromethane (25 mL). Two catalysts, dibutyltin dilaurate (63.2 mg, 0.1 mmol, Aldrich, Milwaukee, Wis.) and triethylamine (10.1 mg, 0.1 mmol, Aldrich, Milwaukee, Wis.) were then added. The reaction mixture was heated under reflux for 7 h. After removal of the solvent, the reaction product was dissolved in distilled water. The aqueous solution was purified by addition of activated carbon and successive filtrations, and then freeze-dried. The resulting polymer was recovered with a 70% yield and was characterized by $^1$H NMR.

Method IV: Using Di-Benzotriazole Carbonate Polyethylene Glycol

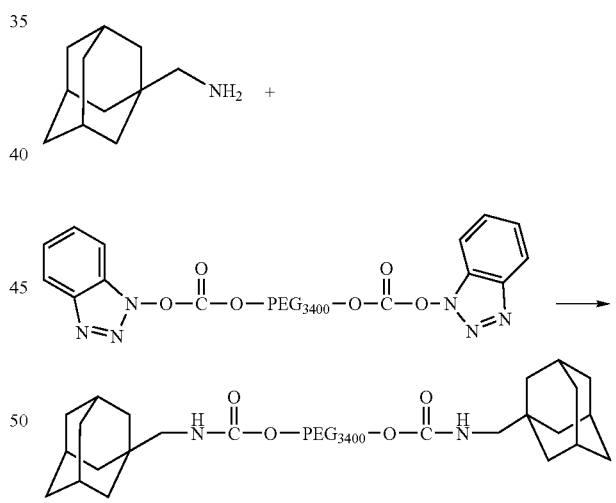

1-Adamantanemethylamine (0.1 g, 0.60 mmol, Aldrich, Milwaukee, Wis.) is added to Dibenzotriazole carbonate polyethylene glycol (PEG$_{3400}$-(BTC)$_2$) (1.02 g, 0.30 mmol, Shearwater Polymers, Inc, Huntsville, Ala.) dissolved in 10 mL of dichloromethane. The resulting solution was stirred at room temperature overnight. The solvent was evaporated under vacuum and the residue was dissolved in water and centrifuged to remove excess 1-adamantanemethylamine. The supernatant was then transferred to a 1,000 MWCO Spectra/Por membrane and dialyzed against water for 24 h. The solution was then freeze-dried to dryness. This afforded 0.88 g of solid (yield 84%).

Example 10

Synthesis of Hydrolysable Diadamantane Polyethylene Glycol Crosslinker:
Various methods were investigated:
  Method I: Using Polyethylene Glycol

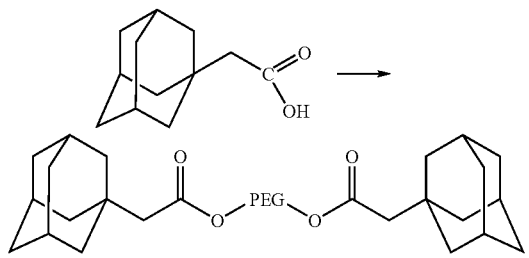

Polyethylene glycol (Mw=1000) (1 mmol, Aldrich, Milwaukee, Wis.) is dried by heating under vacuum at 70° C. overnight. 1-Adamantaneacetic acid (2.2 mmol, Aldrich, Milwaukee, Wis.) is added to the dried polyethylene glycol after its dissolution in anhydrous toluene (15 mL). p-Toluenesulfonic acid (Aldrich, Milwaukee, Wis.) is then added in a catalytic amount. The resulting mixture is azeotropically refluxed for 16 h using Dean-Stark apparatus. After completion of the reaction, the solvent is removed under vacuum and the resulting polymer is precipitated with ether.
  Method II: Using Disuccinimidyl Succinate Polyethylene Glycol

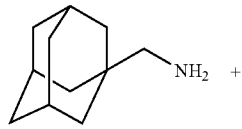

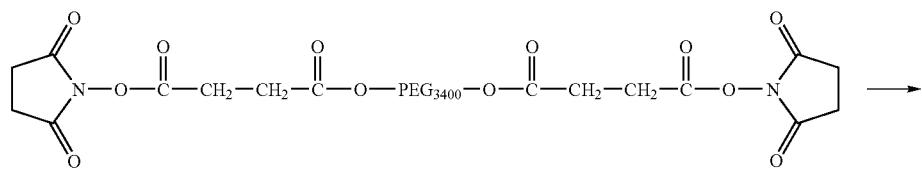

1-Adamantanemethylamine (0.1 g, 0.60 mmol, Aldrich, Milwaukee, Wis.) was added to disuccinimidyl succinate polyethylene glycol (PEG$_{3400}$-(SS)$_2$) (SunBio, Inc., 980-5 Kwan-yang Dong, Anyang City, S. Korea) (0.30 mmol) dissolved in 10 mL of dichloromethane. The resulting solution was stirred at room temperature overnight. The solvent was evaporated under vacuum and the resulting polymer was precipitated with ether.

Example 11

Synthesis of Triadamantane Crosslinker:

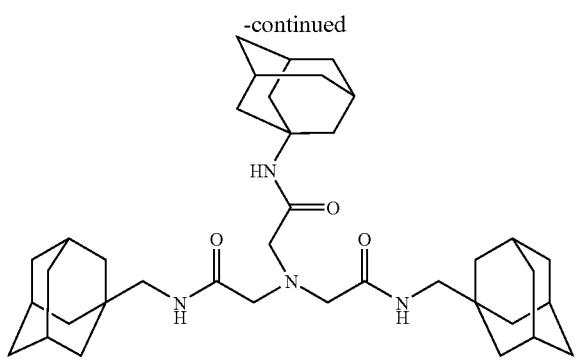

1-Adamantanemethylamine (0.212 g, 1.29 mmol, Aldrich, Milwaukee, Wis.) was added to Tris-succinimidyl aminotriacetate (TSAT) (0.2 g, 0.41 mmol, Pierce, Rockford, Ill.) dissolved in 10 mL of anhydrous dimethylformamide (Aldrich, Milwaukee, Wis.). The resulting mixture was stirred at room temperature under argon for 14 h. The precipitated was filtered and characterized by mass spectroscopy: Electrospray Ionization: 633.4 [M+H]$^+$, 655.6 [M+Na]$^+$, 1265.3 [2M+H]$^+$, 1287.1 [2M+Na]$^+$.

Example 12

Synthesis of Tetraadamantane Crosslinker:

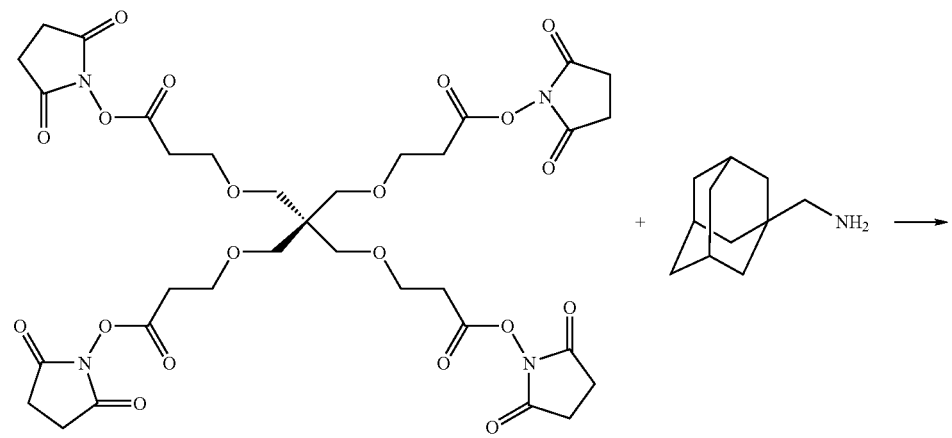

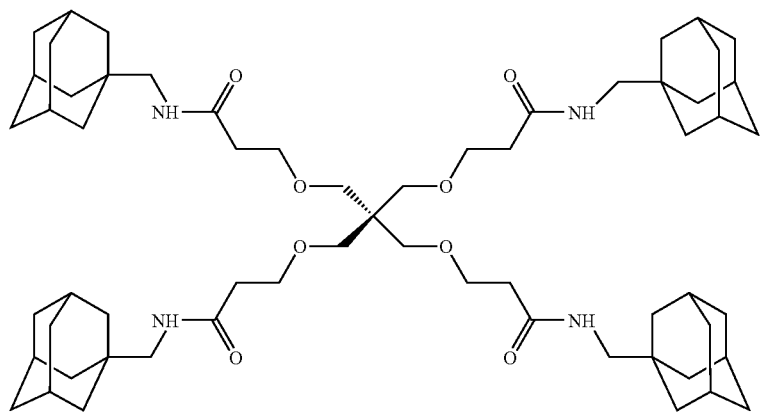

1-Adamantanemethylamine (0.212 g, 1.29 mmol, Aldrich, Milwaukee, Wis.) was added to Tetrakis-(N-succinimidylcarboxypropyl)pentaerythritol (NHS-4) (0.1 g, 0.12 mmol, Molecular Biosciences, Boulder, Colo.) dissolved in 5 mL of anhydrous dimethylformamide (Aldrich, Milwaukee, Wis.). The resulting mixture was stirred at room temperature under argon for 14 h. The precipitated was filtered and characterized by Mass Spectroscopy: Electrospray Ionization: 1013.7 [M+H]$^+$, 1035.8 [M+Na]$^+$.

Example 13

Synthesis of tetra-adamantane polyethylene glycol crosslinker:

Method I: Using Pentaerythritol Ethoxylate (15/4 EO/OH)

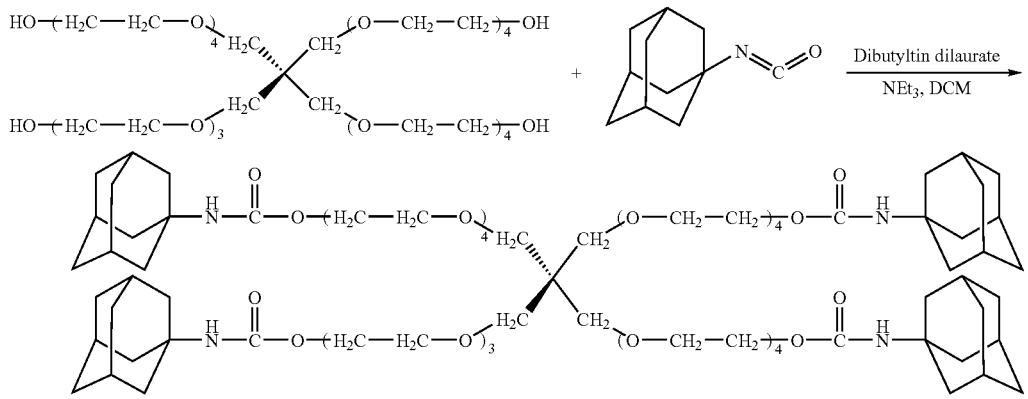

Pentaerythritol ethoxylate (15/4 EO/OH) (Mn=797) (1 mmol, Aldrich, Milwaukee, Wis.) is dried by heating under vacuum at 70° C. overnight. 1-Adamantyl isocyanate (4.4 mmol, Aldrich, Milwaukee, Wis.) is added to the dried polymer after its dissolution in anhydrous dichloromethane (25 mL). Two catalysts, dibutyltin dilaurate (0.1 mmol, Aldrich, Milwaukee, Wis.) and triethylamine (0.1 mmol, Aldrich, Milwaukee, Wis.) are then added. The reaction mixture is heated under reflux for 7 hours. After removal of the solvent, the reaction product is dissolved in distilled water. The aqueous solution is purified by addition of activated carbon and successive filtrations, and then freeze-dried.

Method II: Using 4 arm PEG

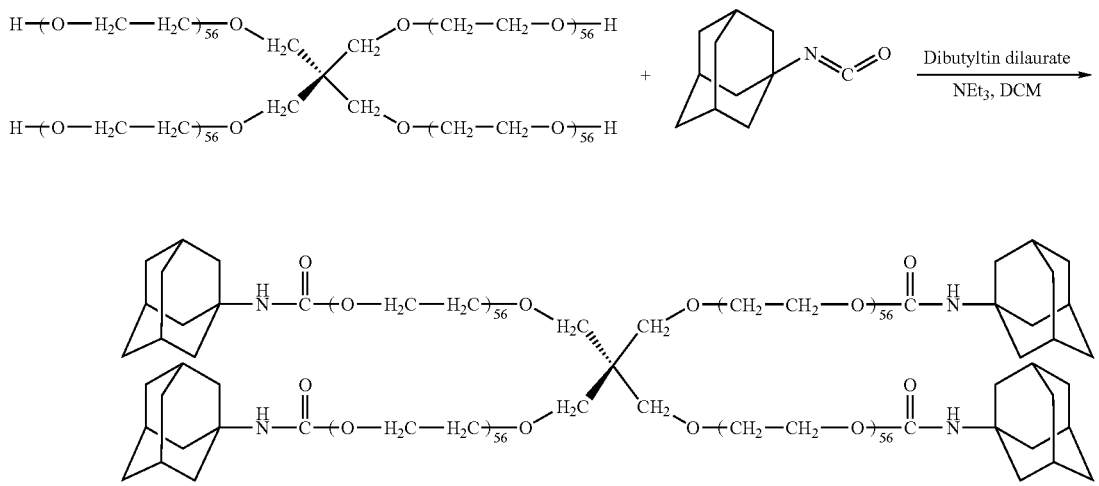

4 arm PEG (Mn=10000) (1 mmol, Shearwater Polymers, Inc, Huntsville, Ala.) is dried by heating under vacuum at 70° C. overnight. 1-Adamantyl isocyanate (4.4 mmol, Aldrich, Milwaukee, Wis.) is added to the dried polymer after its dissolution in anhydrous dichloromethane (25 mL). Two catalysts, dibutyltin dilaurate (0.1 mmol, Aldrich, Milwaukee, Wis.) and triethylamine (0.1 mmol, Aldrich, Milwaukee, Wis.) are then added. The reaction mixture is heated under reflux for 7 hours. After removal of the solvent, the reaction product is dissolved in distilled water. The aqueous solution is purified by addition of activated carbon and successive filtrations, and then freeze-dried.

Example 14

Synthesis of Hydrolysable Tetra-Adamantane Polyethylene Glycol Crosslinker:
Method I: Using Pentaerythritol Ethoxylate (15/4 EO/OH)

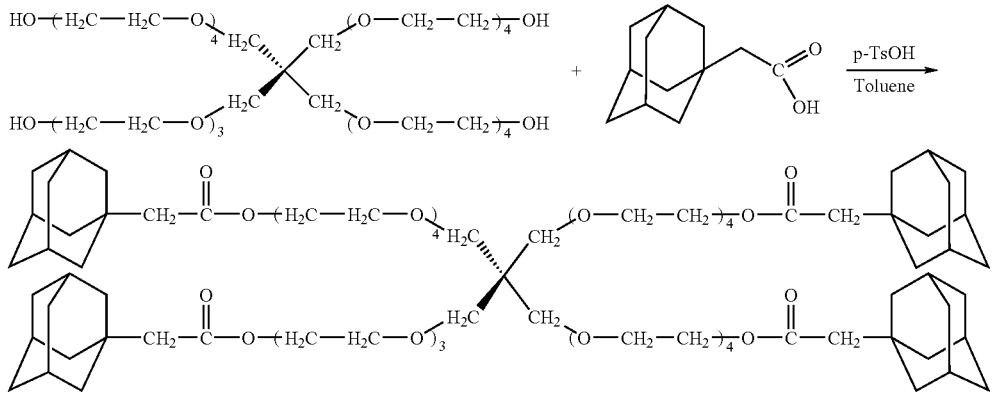

Pentaerythritol ethoxylate (15/4 EO/OH) (Mn=797) (1 mmol, Aldrich, Milwaukee, Wis.) is dried by heating under vacuum at 70° C. overnight. 1-Adamantaneacetic acid (4.4 mmol, Aldrich, Milwaukee, Wis.) is added to the dried polymer after its dissolution in anhydrous toluene. p-Toluenesulfonic acid (Aldrich, Milwaukee, Wis.) is then added in a catalytic amount. The resulting mixture is azeotropically refluxed for 16 h using Dean-Stark apparatus. After completion of the reaction, the solvent is removed under vacuum and the resulting polymer is precipitated with ether.

Method II: Using 4 arm PEG

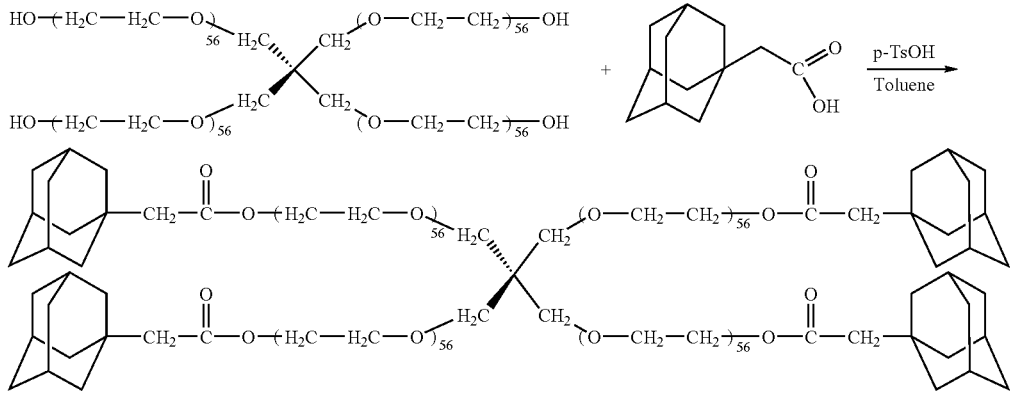

4 arm PEG ($M_n$=10000) (1 mmol, Shearwater Polymers, Inc, Huntsville, Ala.) is dried by heating under vacuum at 70° C. overnight. 1-Adamantaneacetic acid (4.4 mmol, Aldrich, Milwaukee, Wis.) is added to the dried polymer after its dissolution in anhydrous toluene. p-Toluenesulfonic acid (Aldrich, Milwaukee, Wis.) is then added in a catalytic amount. The resulting mixture is azeotropically refluxed for 16 h using Dean-Stark apparatus. After completion of the reaction, the solvent is removed under vacuum and the resulting polymer is precipitated with ether.

Method III: Using 4-arm PEG-succinimidyl Succinate (PEG-SS)$_4$

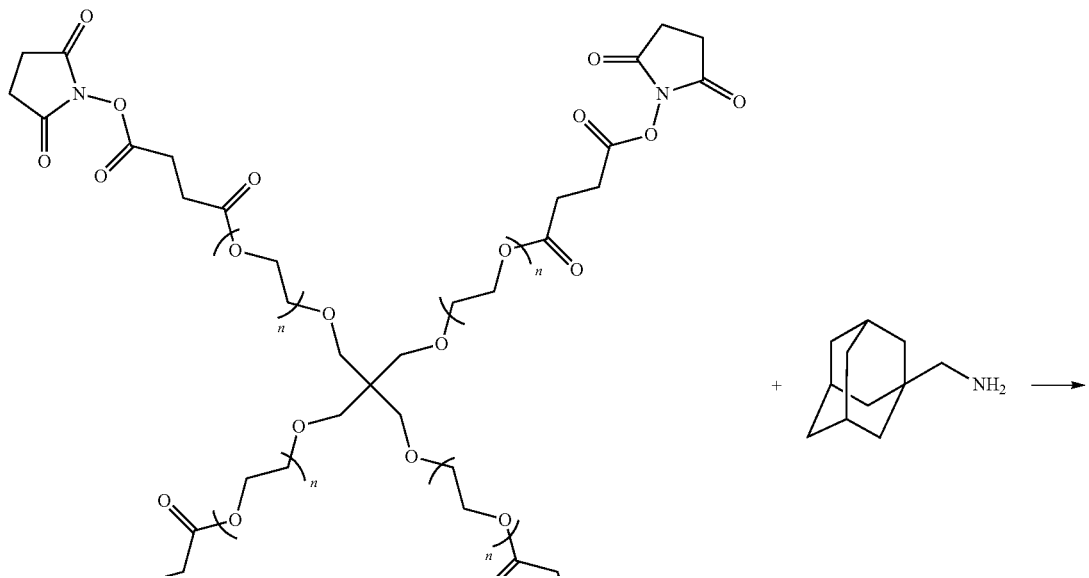

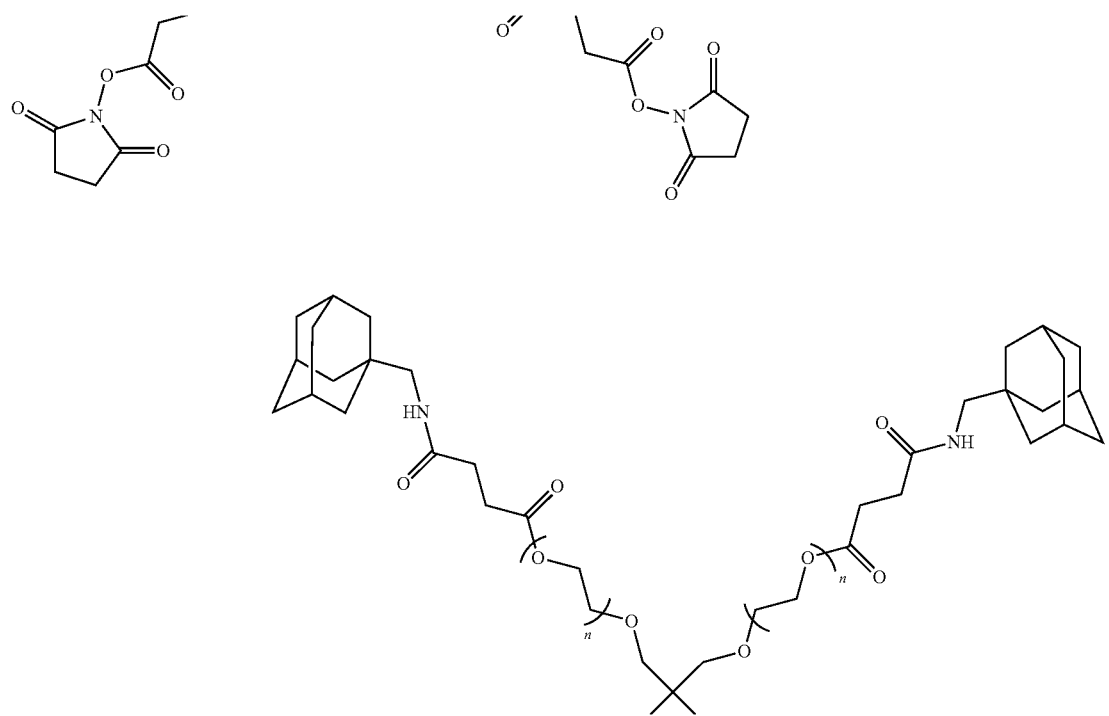

-continued

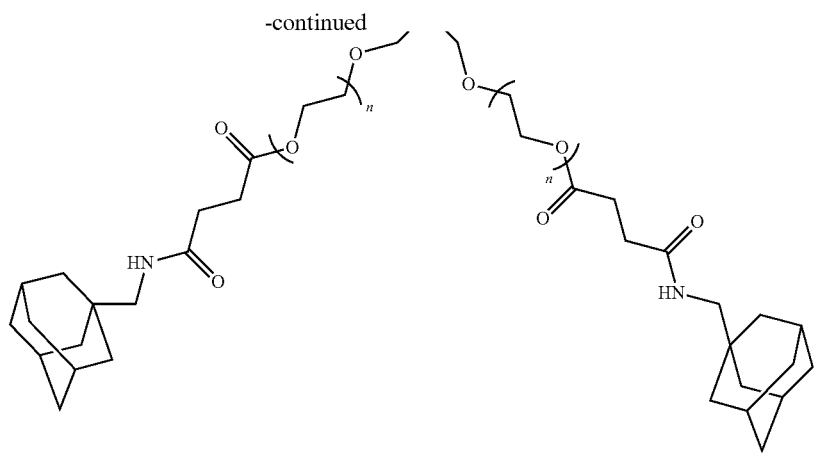

1-Adamantanemethylamine (0.069 g, 0.44 mmol, Aldrich, Milwaukee, Wis.) was added to 1 g of disuccinimidyl succinate polyethylene glycol (($PEG_{10k}$-SS)$_4$) (SunBio, Inc., 980-5 Kwan-yang Dong, Anyang City, S. Korea) (0.1 mmol) previously dissolved in 10 mL of dichloromethane. The resulting solution was stirred at room temperature overnight. The solvent was evaporated under vacuum and the resulting polymer was precipitated with ether.

Example 15

Synthesis of Octa-Adamantane Polyethylene Glycol Crosslinker:

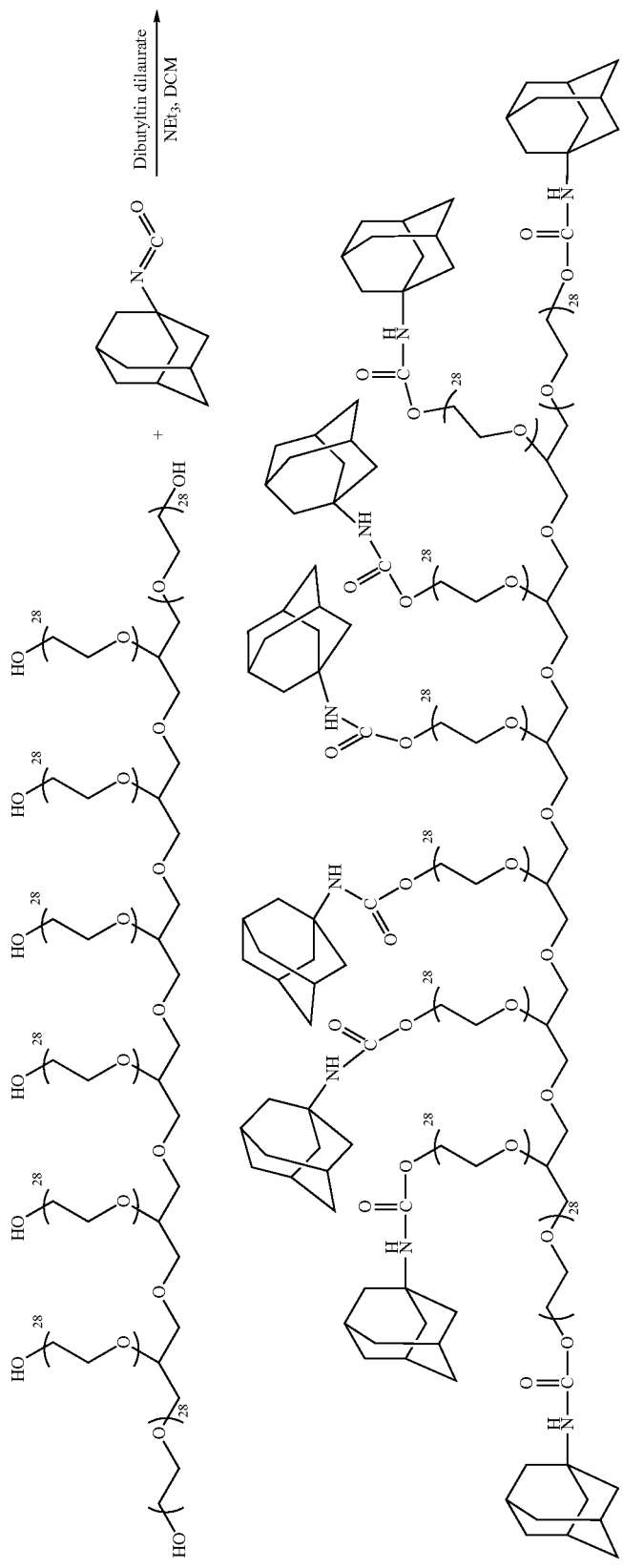

8 arm PEG (Mn=10000) (1 mmol, Shearwater Polymers, Inc, Huntsville, Ala.) is dried by heating under vacuum at 70° C. overnight. 1-Adamantyl isocyanate (4.4 mmol, Aldrich, Milwaukee, Wis.) is added to the dried polymer after its dissolution in anhydrous dichloromethane (25 mL). Two catalysts, dibutyltin dilaurate (0.1 mmol, Aldrich, Milwaukee, Wis.) and triethylamine (0.1 mmol, Aldrich, Milwaukee, Wis.) are then added. The reaction mixture is heated under reflux for 7 hours. After removal of the solvent, the reaction product is dissolved in distilled water. The aqueous solution is purified by addition of activated carbon and successive filtrations, and then freeze-dried.

Example 16

Synthesis of Hydrolysable Octa-Adamantane Polyethylene Glycol Crosslinker:

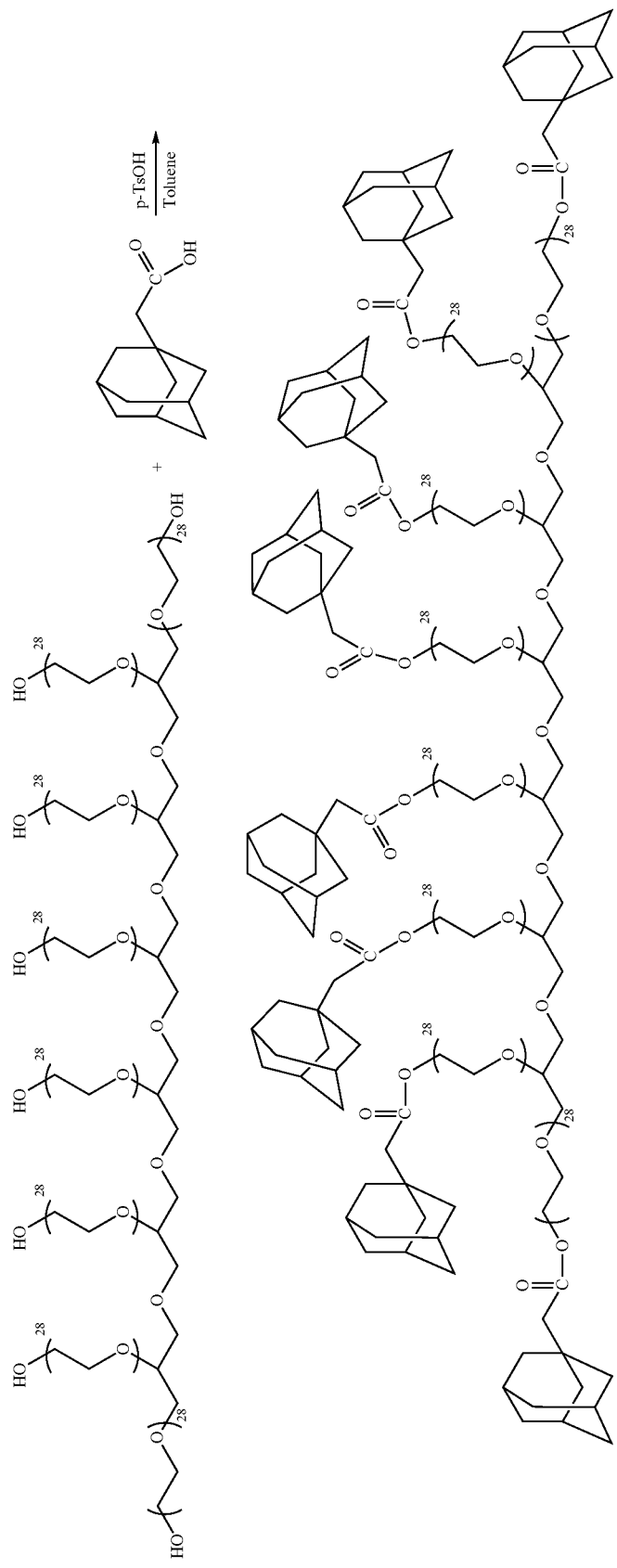

8 arm PEG (Mn=10000) (1 mmol, Shearwater Polymers, Inc, Huntsville, Ala.) is dried by heating under vacuum at 70° C. overnight. 1-Adamantaneacetic acid (4.4 mmol, Aldrich, Milwaukee, Wis.) is added to the dried polymer after its dissolution in anhydrous toluene. p-Toluenesulfonic acid (Aldrich, Milwaukee, Wis.) is then added in a catalytic amount. The resulting mixture is azeotropically refluxed for 16 h using Dean-Stark apparatus. After completion of the reaction, the solvent is removed under vacuum and the resulting polymer is precipitated with ether.

Example 17

Synthesis of Multi Adamantane Crosslinker:

Method I: Using Branched PEI

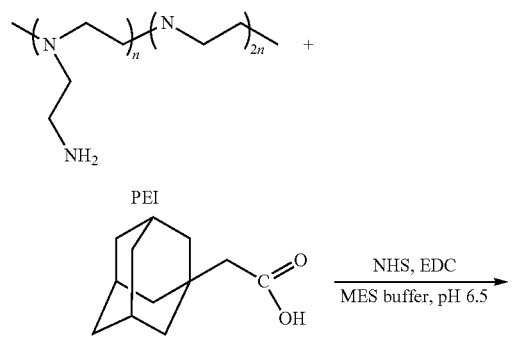

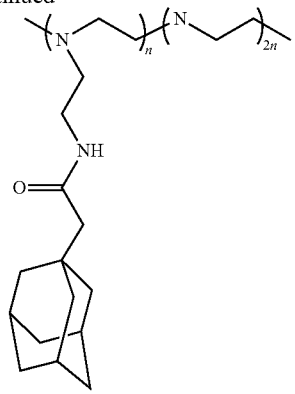

Adamantane-PEI

1-Adamantaneacetic acid (Aldrich, Milwaukee, Wis.) is added to PEI (Aldrich, Milwaukee, Wis.) dissolved in MES buffer 25 mM, pH 6.5. 1-(3-dimethylaminopropyl)-3-ethyl-carbodiimide hydrochloride (EDC) (Aldrich, Milwaukee, Wis.) and N-Hydroxysuccinimide (NHS) (Aldrich, Milwaukee, Wis.) are then added to the reaction mixture. The reaction mixture is stirred at room temperature for 24 h and then transferred to a 10000 MWCO Spectra/Por membrane and dialyzed against water for 24 h. The solution was then freeze-dried to dryness.

Method II: Using Pullulan (Akiyoshi et al. 1993, Macromolecules 26:3062-3068)

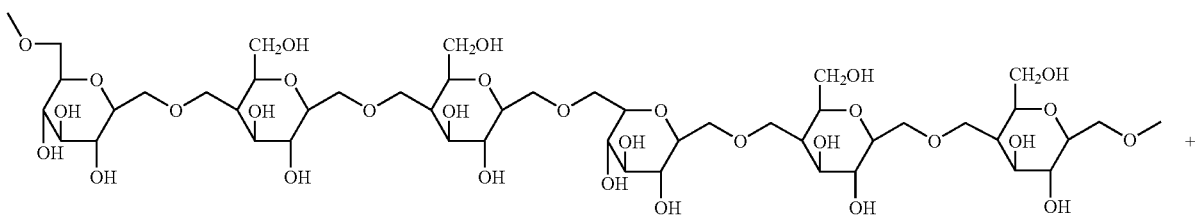

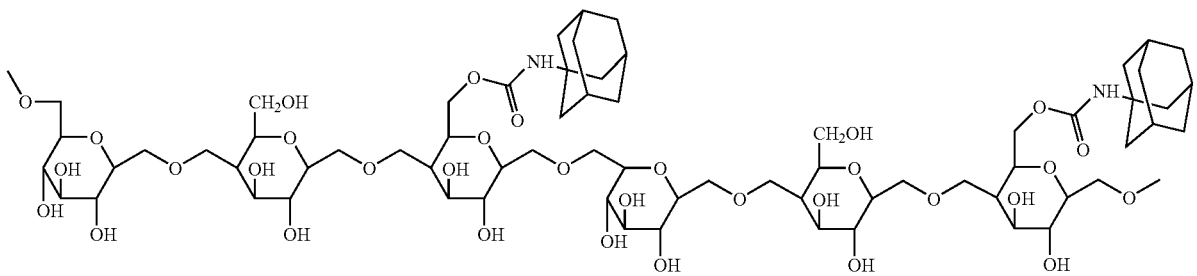

1-Adamantyl isocyanate (Aldrich, Milwaukee, Wis.) is reacted with Pullulan (Sigma-Aldrich, Milwaukee, Wis.) in anhydrous DMSO containing pyridine at 80° C. for 8 h. Ethanol is added to the reaction mixture, and the resulting mixture is stored overnight at 4° C. The precipitates are separated, purified by dialysis against water and lyophilized to dryness. The degree of substitution of the adamantane group is determined by $^1$H NMR.

Example 18

Synthesis of Hydrolysable Multi Adamantane Crosslinker: (Sunamoto et al. 1992, *Macromolecules* 25:5665-5670)

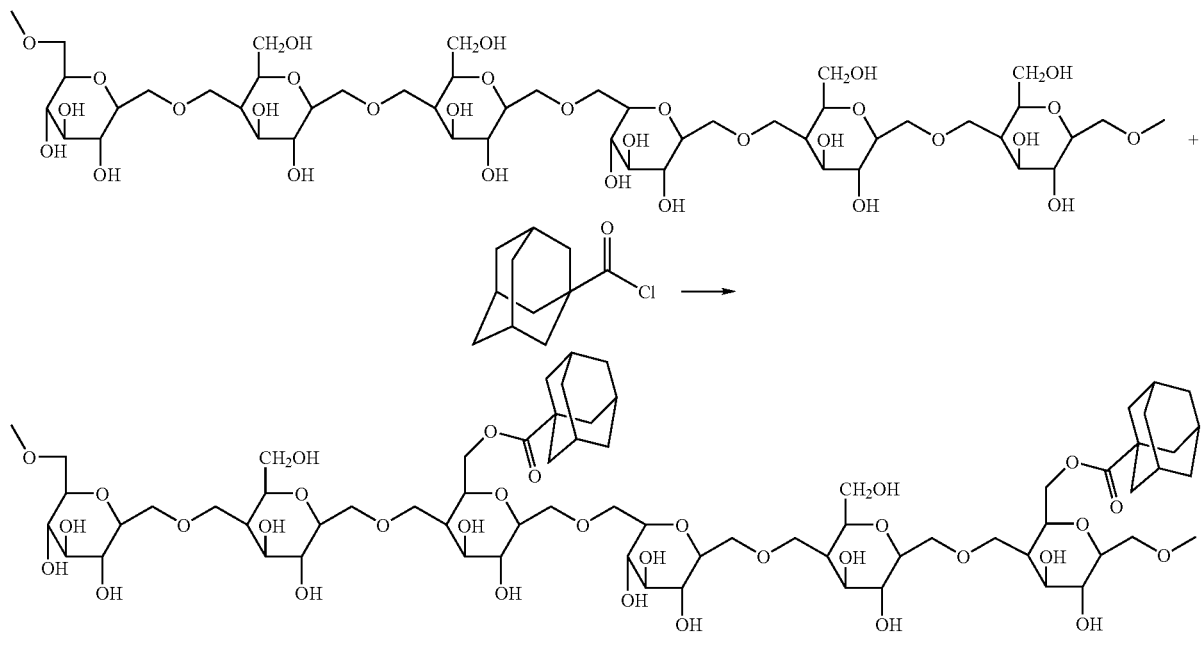

Pullulan (Sigma-Aldrich, Milwaukee, Wis.) is dissolved in anhydrous DMF at 60° C. 1-Adamantanecarbonyl chloride (Aldrich, Milwaukee, Wis.) dissolved in anhydrous DMF and anhydrous Pyridine are added. The resulting mixture is stirred at 60° C. for 2 h and another 1 h at room temperature. The mixture is poured into ethanol. The precipitates are collected and washed with ethanol and then, with diethyl ether. The solid is dried under vacuum at 50° C. for 2 h. The degree of substitution of the adamantane group is determined by $^1$H NMR.

Example 19

Synthesis of Self-Crosslinked Polymer:

The synthesis of a polymer that contains cylodextrin and adamantane functions is carried out in three steps.

1. Step 1: Synthesis of monomer $6^A,6^D$-Bis-(2-amino-2-carboxylethylthio)-$6^A,6^D$-dideoxy-β-cyclodextrin, (CD-Bis Cys)

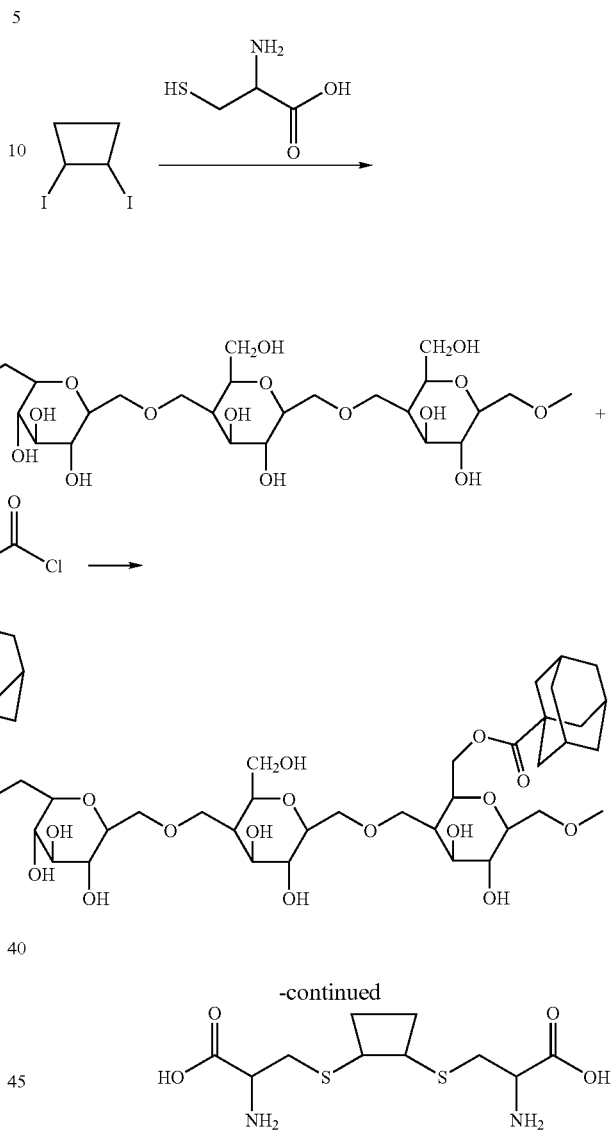

A 167 mL of 0.1 M sodium carbonate buffer was degassed for 45 minutes in a 500 mL 2-neck round bottom flask equipped with a magnetic stir bar, a condenser and septa. To this solution was added 1.96 g (16.2 mmol) of L-cysteine and 10.0 g (73.8 mmol) of di-iodo-β-cyclodextrin (Gonzalez et al. 1999 *Bioconjugate Chem.* 10: 1068-1074; and Hwang et al. 2001 *Bioconiugate Chem.* 12(2): 280-290; Gonzalez, H., Hwang, S. J., and Davis, M. E. (2000) Linear Cyclodextrin Copolymers WO001734A1). The resulting suspension was heated at a reflux temperature for 4.5 h. until the solution turned clear colorless. Then, it was cooled to room temperature and acidified to pH 3 using 1 N HCl. The product was crashed out by slow addition of acetone (3 times weight ratio of the solution). This afforded 9.0 g (90.0%) yield of CD-Bis Cys. The resulting solid was subjected to anionic exchange column chromatography using a gradient elution of 0-0.4 M ammonium bicarbonate solution. ESI/MS (m/z): 1342 [M]+, 1364 [M+Na]+. Purity of CD-Bis Cys was confirmed by HPLC.

2. Step 2: Synthesis of CD-Bis Cys-PEG$_{34000}$ Copolymers

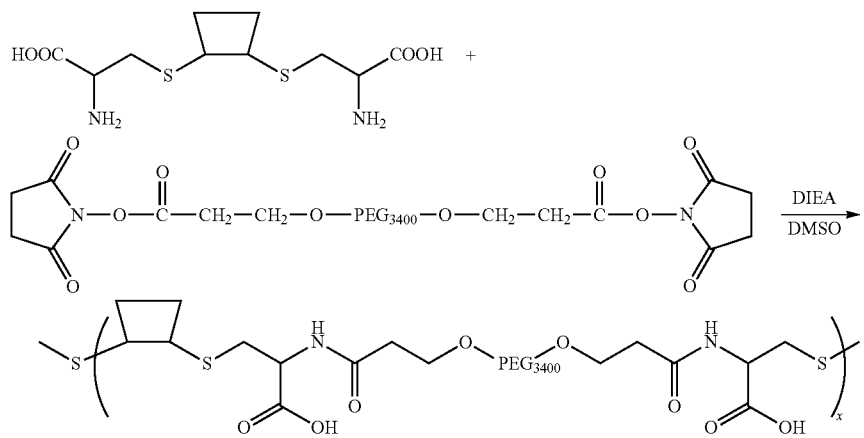

CD-Bis Cys (2 g, 1.49 mmol) and SPA-PEG$_{3400}$-SPA (5.07 g, 1.49 mmol, Shearwater Inc.) were dissolved in dry DMSO (40 mL). After 10 minutes diisopropylethylamine (DIEA, 0.571 mL, 2.2 eq, Aldrich) was added under argon. The reaction mixture was stirred under argon for 2-6 days. An increase of viscosity was observed as a function of polymerization time. Water (200 mL) was added to the polymerization solution with vigorous stirring. The solution was then dialyzed in 25,000 MWCO Spectra/Por 7 membrane for 2.5 days at a concentration of ca. 10 mg polymer/mL water. After lyophilization, a white fluffy powder (6.2 g, 92% yield) was obtained.

Characterization: Light Scattering and Molecular Weight Determination

The specific refractive index increment, dn/dc, was measured in Phosphate Buffered Saline 1×(PBS) (Cellgro, Mediatech, Inc, Hemdon, Va.) using a Bausch & Lomb ABBE-3L refractive index. Polymer samples were then analyzed on a Hitachi D6000 HPLC system equipped with a ERC-7512 RI detector, a Precision Detectors PD2020/DLS static light scattering detector and an PL aquagel-OH 30 (Polymer Laboratories, Amherst, Mass.) column using Phosphate Buffered Saline 1×as eluant at a 0.7 ml/min flow rate. The dn/dc was calculated to be 0.1348 and the weight average molecular weight Mw was determined to be 103,500 Da with a polydispersity index Mw/Mn of 1.71.

3. Adamantane conjugation to CD-Bis Cys-PEG$_{3400}$ Copolymers

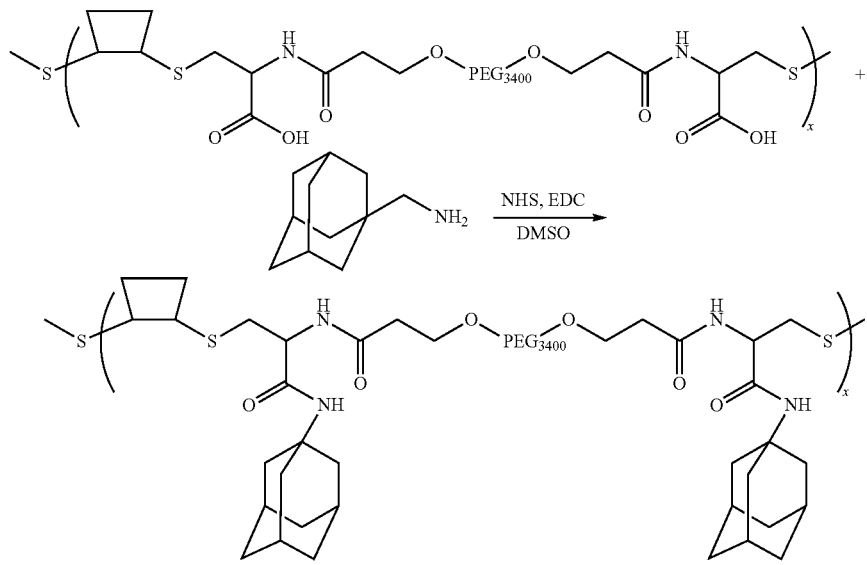

CD-Bis Cys-PEG$_3$400 copolymer (0.32 mmol of repeat unit) is dissolved in dry DMSO and stirred for 10 minutes. 1-Adamantanemethylamine (0.76 mmol, Aldrich, Milwaukee, Wis.), DIEA (0.76 mmol), EDC (0.96 mmol) and NHS (0.71 mmol) are added to the polymer solution. The mixture is stirred for about 16 hours. Water is added to the resulting mixture to remove excess 1-Adamantanemethylamine. After filtration of the precipitates, the solution is dialyzed against water with 10,000 MWCO Spectra/Por membrane for 48 h and lyophilized to dryness. The degree of substitution of the adamantane group is determined by $^1$H NMR.

Example 20

Synthesis of RGD-modified Adamantane-PEG Derivative

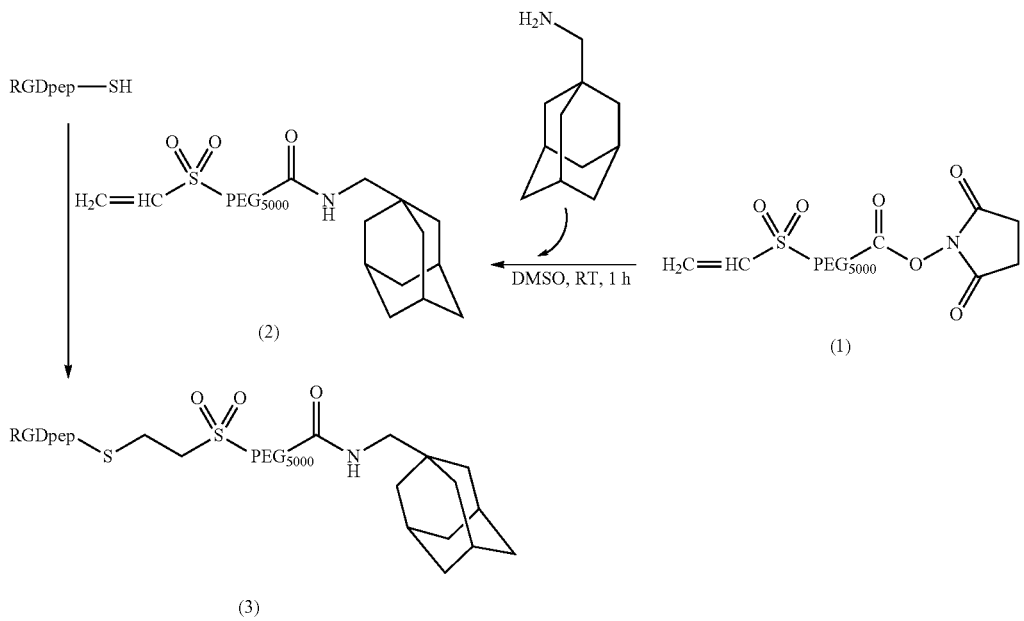

Step 1: Synthesis of VS-PEG$_{5000}$-AD (2)

Vinylsulfone-PEG$_{5000}$-NHS (1) (Shearwater Polymers, 0.147 mmol) was added to a round bottom flask equipped with a stir bar and dissolved in 5 mL of DMSO. To this was added Adamantanemethylamine (Aldrich, 0.147 mmol). The resulting solution was stirred 1 h at room temperature. The resulting mixture was dialyzed overnight against 3500 MWCO Membrane (Spectra Por). The solution was then lyophilized to afford Vinylsulfone-PEG$_5$000-AD (2).

Step 2: RGDpep-PEG-AD Conjugate Synthesis

RGDpep-SH synthesized as described in Kok et al. (Bioconjugate Chemistry (2002), 13(1), 128-135) is dissolved in PBS (phosphate buffer saline) 1×, pH 7.2. Vinylsulfone-PEG$_{5000}$-AD (2) is then added to the RGDpep-SH solution. The resulting solution is stirred at room temperature for 2 hours. The polymer solution is then transferred to a Spectra/Por 7 MWCO 3500 membrane (Spectrum, Houston, Tex.) and dialyzed against water for 24 h. The solution is then freeze-dried to dryness to afford RGDpep-PEG$_{5000}$-AD (3).

Example 21

Preparation of Material:

The polymer bearing the inclusion host (Example 1-6) was dissolved at 100 mg/mL in PBS (phosphate-buffered saline) 1×, pH 7.2. The crosslinker (Example 7-18) (ratio: Adamantane/cylodextrin: 1/1 or 1/2) was then added. The resulting mixture was mixed vigorously in order to get the crosslinker in solution. An increase in the viscosity was observed in about 10 min.

Example 22

Preparation of Ionic Type Material:

Using Multivalent Ion

The polymer bearing the inclusion host and carboxyl groups (See Example 19, Step 2) was dissolved at 100 mg/mL in 0.1 M CaCl$_2$ aqueous solution and then added to a vial containing a mixture of the crosslinker (Example 7-18) (ratio: Adamantane/cyclodextrin: 1/1 or 1/2). The resulting mixture was mixed vigorously in order to get the crosslinker and the diamino compound in solution. An increase in the viscosity was observed.

Using Diamino Compound

The polymer bearing the inclusion host and carboxyl groups (See Example 19, Step 2) was dissolved at 100 mg/mL in water and then added to a vial containing a mixture of the crosslinker (Example 7-18) (ratio: Adamantane/cyclodextrin: 1/1 or 1/2) and a diamino compound like PEG$_{3400}$-(NH$_2$)$_2$ (Shearwater Polymers) or CnH$_{2n}$—(NH$_2$)$_2$ (ratio: NH$_2$/COO$^-$: 1/1 or 1/2). The resulting mixture was mixed vigorously in order to get the crosslinker and the diamino compound in solution. An increase in the viscosity was observed.

Using Polycation

The polymer bearing the inclusion host and carboxyl groups (See Example 19, Step 2) was dissolved at 100 mg/mL in water and then added to a vial containing a mixture of the crosslinker (Example 7-18) (ratio: Adamantane/cyclodextrin: 1/1 or 1/2) and a polycation like polylysine or polyethyleneimine. The resulting mixture was mixed vigorously in order to get the crosslinker and the polycation in solution. An increase in the viscosity was observed.

Example 23

Preparation of Material Containing Virus or Protein:

The polymer bearing the inclusion host (Example 1-6) was dissolved in PBS (phosphate-buffered saline) 1×, pH 7.2 containing the protein or virus at the desired concentration to obtain a polymer solution at a final concentration of 100 mg/mL of solution. The crosslinker (Example 7-18) (ratio: Adamantane/cylodextrin: 1/1 or 1/2) was then added. The resulting mixture was mixed vigorously in order to get the crosslinker in solution. An increase in the viscosity was observed in about 10 min.

Example 24

Preparation of Material Containing a Signaling Peptide

The polymer bearing the inclusion host (Example 1-6) is dissolved in PBS (phosphate-buffered saline) 1×, pH 7.2 (containing when desired proteins, virus, or other drugs or drug delivery systems) at the desired concentration to obtain a polymer solution at a final concentration of 100 mg/mL of solution. The crosslinker (Example 7-18) (ratio: Adamantane/cylodextrin: 1/2) and the signaling peptide (Example 20) (ratio: Adamantane/cyclodextrin: 1/2) are then added. The resulting mixture is mixed vigorously in order to get the crosslinker in solution. An increase in the viscosity is observed in about 10 min.

Example 25

Studies Concerning Cell Mobility Through Matrix.
a. Matrix (0.2 mL, composed of CD-PEG$_{3400}$ and bis-(2 (1-adamantyl)ethyl)phosphate) was prepared as described in Example 21 and added to the bottom of FluoroBlok inserts (for 24 well format, Falcon Catalog #351152).
b. CCD cells were rinsed with PBS and then exposed to 5 µM of Calcein-AM, a fluorescent marker, for 15-30 minutes.
c. CCD cells were then trypsinized and plated on top of the matrix in the insert at 10,000 cells/insert in 0.5 mL media.
d. 1 mL of media containing 10 ng/mL human PDGF protein was then added to the lower chamber.
e. Cell mobility through the matrix and into the lower chamber was monitored for 3 days by fluorescence microscopy. Successful migration through the matrix and past the insert was demonstrated by the presence of cells in the lower chamber observed by fluorescence microscopy 72 hours after plating as shown in FIG. 5.

Example 26

Transfection Studies to CCD Fibroblast Cells with CD-PEI Polyplexes Formulated with Matrix.

The well bottoms in 24-well plates were coated with ~0.2 mL of the following:
a. No coating (control)
b. Matrix
c. Matrix containing 1 µg of luciferase gene-containing plasmid.
d. Matrix containing CDP polyplex.
e. Matrix containing CDPEI polyplex.
f. No coating. Free CDPEI polyplex (positive control I: traditional transfection procedure)
g. No coating. Free CDP polyplex (positive control II: traditional transfection procedure).

CCD (fibroblast cells, ATCC) were plated in the 24 well plates at 40,000 cells/well. 24 hours after plating the cells, media was removed, cells rinsed with PBS, and lysed. The cell lysates were analyzed for luciferase protein activity using luciferase assay. Results are reported in RLU/well. This experiment demonstrates that the cells are able to successfully migrate into the matrix and be transfected by the polyplexes contained in the matrix. Transfection efficiency is only slightly lower than transfection by polyplexes free in media.

Note: the matrix is comprised of CD-PEG (see Example 3, method II for synthesis procedure) crosslinked with a diadamantane crosslinker (bis-(2(1-adamantyl)ethyl)phosphate, see Example 7 for synthesis procedure). Matrix formulation procedure is described in Example 21. When polyplexes are included in the matrix, the polyplexes are prepared by adding a 10 µL solution of polymer to 10 µL solution of luciferase gene-containing plasmid (0.1 mg/mL) at the optimum charge ratio. The polyplexes are included in the buffer solution that is used to dissolve the CD-PEG component of the matrix and matrix formulated as described in Example 21.

For positive control experiments, polyplexes are prepared as described and added directly to the cell media.

Example 27

Materials can be prepared, as schematically depicted in FIG. 1, by the self-assembly of cyclodextrin (CD)-containing polymers (A) and di- or multi-functional linkers (B) terminated with molecules capable of forming inclusion complexes with the cyclodextrin-containing polymers. The materials (P) may be formulated to contain proteins, cells, viruses, polyplexes, or other therapeutic agents or delivery systems containing therapeutic agents.

An exemplary linker,

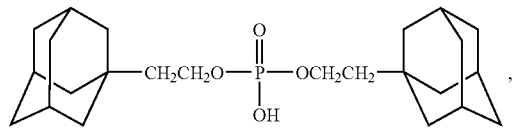

can be prepared by following the protocols described in the Breslow and Zhang, JACS (1996), 118, 8495-8496, and Zhang and Breslow, JACS (1993), 115, 9353-9354. One of skill in the art can readily modify this protocol, in light of techniques generally known in the art, to arrive at a wide spectrum of different linkers that can be employed as linking molecules as the term is used herein. The difunctional linkers or cyclodextrin-containing polymers may contain biodegradable linkages to facilitate the release of the therapeutic agents and/or degradation of the material.

Compounds increasing the therapeutic utility of the material, such as signaling peptides or other moieties facilitating cell migration, may be incorporated into the material by conjugating a inclusion complex guest to the entity of interest and including the conjugate in the material as described in FIG. 2. The conjugate may be included before, during or after the cross-linking process.

For example, a polymer made of repeated subunits having the formula:

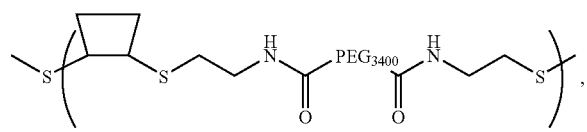

e.g., wherein the Mw of monomer is approximately 4800, can be prepared as a solution of the polymer at 100 mg/mL in PBS (phosphate-buffered saline) 1×, pH 7.2. It may be desirable to centrifuge the mixture and then agitate the solution to solubilize the polymer. A 33.3 µL aliquot of a solution of the linking molecule

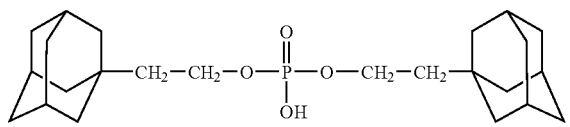 [SMILES: O=P(O)(OCCC12CC3CC(CC(C3)C1)C2)OCCC12CC3CC(CC(C3)C1)C2]

at 132 mg/mL in dichloromethane, can be placed into a vial to let the dichloromethane evaporate at room temperature or in an oven at 37° C. 1 mL of the polymer solution can then be added to the residual linker, optionally triturating to facilitate solution. The solution may then be allowed to rest, and after a time, e.g., 10 min., the solution may become viscous. To include a foreign substance, such as a therapeutic agent or viral particles, into the crosslinked polymer, the substance may be present in the solution prior to the final resting period. For example, the substance may be present in the solvent used to dissolve the cyclodextrin polymer or in the initial solution of the linking molecule, or may be added to either component or to the final solution prior to the crosslinking reaction.

Example 28

Methods and Results:
Matrix 1 (60 kD polymer prepared according to Example 3, method II and cross-linking agent prepared according to Example 9, method II) and Matrix 2 (80 kD polymer prepared according to Example 3, method II and crosslinking agent prepared according to Example 9, method II) were used.
Application of 60 kD Matrix in vivo.
300 µl of 60 kD matrix was drawn up into a 1 cc syringe and all air bubbles were removed by moving the syringe plunger up and down. A 23G needle was large enough for matrix to pass through with some pressure required. A 20G needle was large enough to allow the matrix to pass through easily.
Male Sprague-Dawley rats were sacrificed, shaved, and 8 mm wounds were made on their dorsal regions. Using a 1 cc syringe with 20G needle, excess 60 kD matrix was expelled until 100 µL of volume remained. Matrix was then applied to an 8 mm wound punch without any over-fill. The same procedure was performed except with 150 µl of Matrix 1 and this over-filled an 8 mm punch wound in rat dorsum skin.
The feasibility of applying matrix to an incisional wound was explored. A full-thickness incision approximately 2 inches in length was made on a rat dorsum. A syringe was filled with 200 µL of 60 kD matrix and was successfully injected intra-dermally at the incision site using a 20G needle.
Application of 80 kD Matrix
Two 8 mm full-thickness dermal punches were made on a rat dorsum. One punch was treated with 100 µL of 80 kD matrix using a 1 cc syringe and a 20G needle. This volume filled the punch evenly; however, more force was required to deliver 80 kD when compared to 60 kD matrix. 150 µL of 80 kD matrix overfilled an 8 mm dermal punch. 200 µl of 80 kD matrix was successfully delivered by intra-dermal injection although substantial force was required to complete the injection.

Example 29

Studies were performed to acquire initial rheological data of the CD-PEG$_{3400}$ matrix (100 mg/ml) (Example 3, method II) before and after crosslinking with di-Adamantane-PEG (36.5 mg/ml) (Example 9, method II). These data were compared to collagen matrix at 2.4 mg/ml, one of the standard formulations used in preclinical model development.

Figure 7:
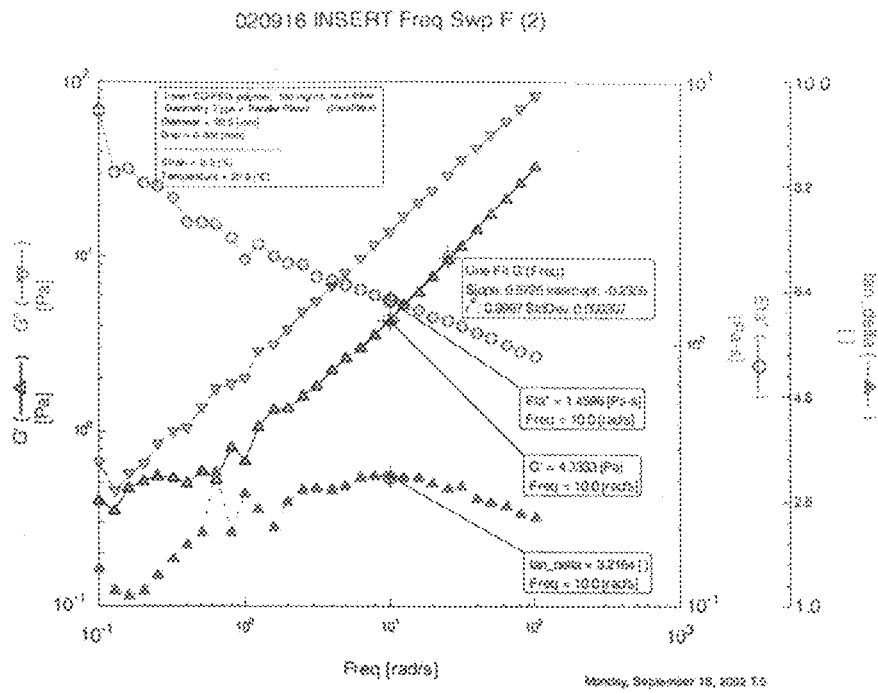
FIG. 7 presents a dynamic frequency sweep of $CD\text{-}PEG_{3400}$ polymer without cross linker. Concentration was 100 mg/ml in PBS, temperature was 20° C. and strain was 0.5%.
Figure 8:
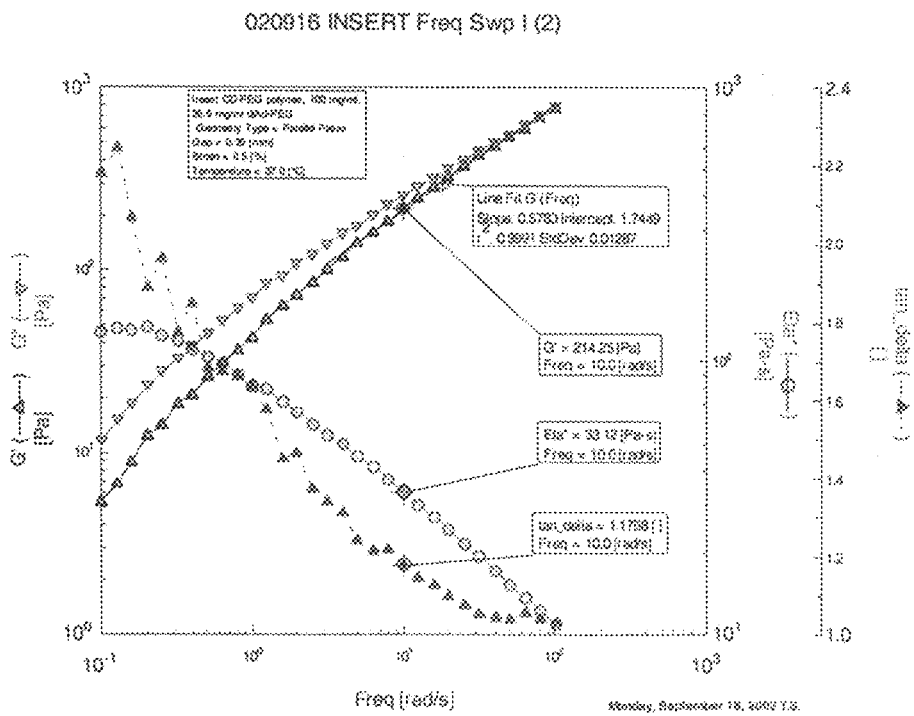
FIG. 8 provides a dynamic frequency sweep of $CD\text{-}PEG_{3400}$ polymer (100 mg/ml) with 36.5 mg/ml of di-Adamantane-PEG cross linker. Temperature was 37° C. and strain was 0.5%.
Figure 9:
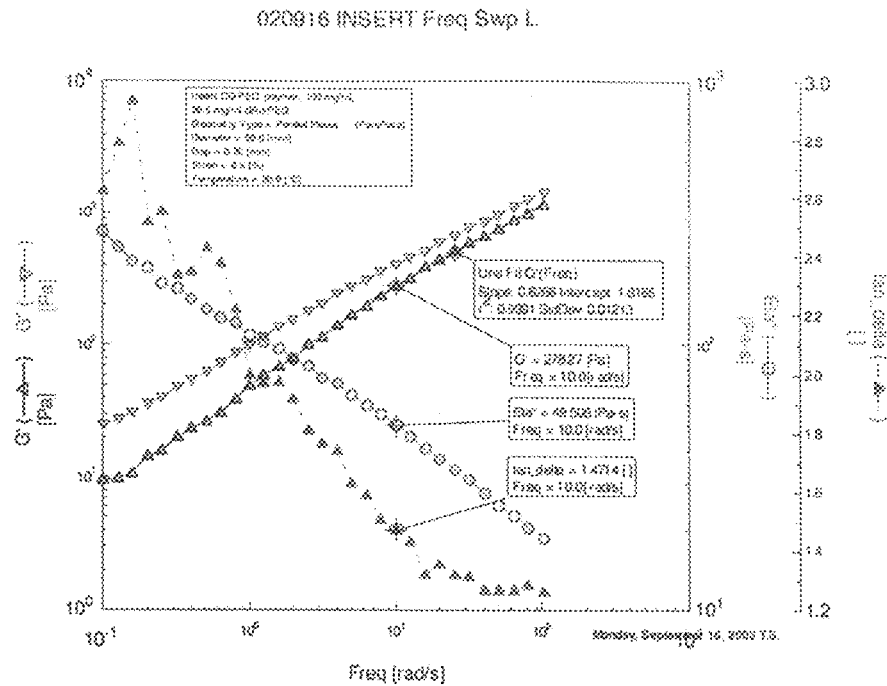
FIG. 9 is a dynamic frequency sweep of $CD\text{-}PEG_{3400}$ polymer (100 mg/ml) with 36.5 mg/ml of di-Adamantane-PEG cross linker. Temperature was 20° C. and strain was 0.5%.
Figure 10:
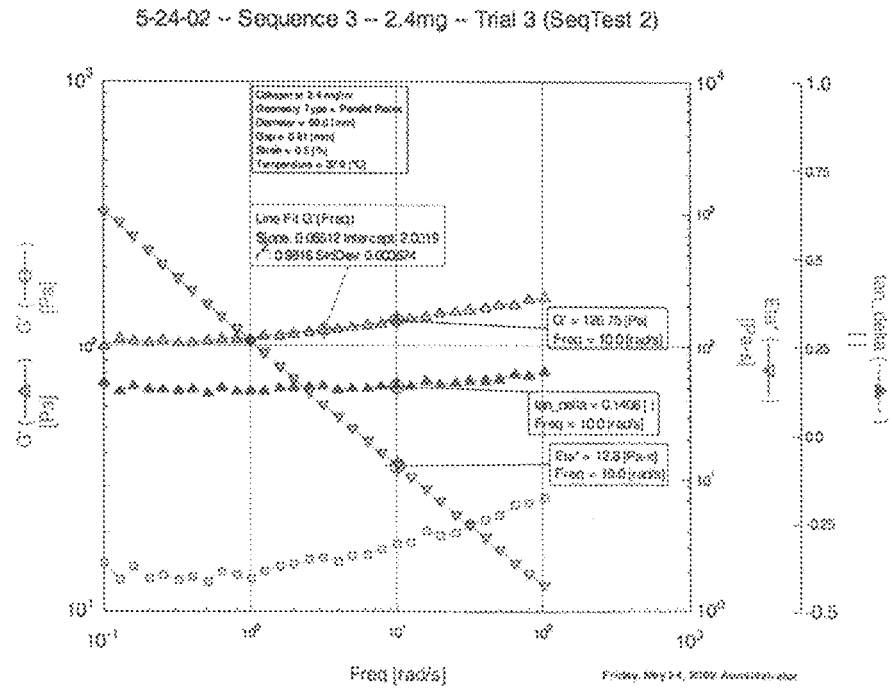
FIG. 10 shows a dynamic frequency sweep of bovine collagen matrix at 2.4 mg/ml. Temperature was 37° C. and strain was 0.5%.

Results:
The first series of experiments were performed with CD-PEG$_{3400}$ polymer at 100 mg/ml without cross linker. Frequency sweeps at various constant strains were performed.
FIG. 7 shows a frequency sweep at 37° C. G" is greater than G', resulting in a tan δ of approximately 3.2. As expected, this polymer solution exhibits mostly viscous behavior. This is confirmed by the slope of G' as a function of frequency. For purely viscous fluids, a theoretical slope of 2 is expected whereas for purely elastic fluids, a slope of 0 is expected over a certain frequency range. On a structural level, the interpretation of these results is that the polymer molecules interact with each other by some sort of weak interaction. Energy applied to the material can be stored by the molecules elastically by moving nodes of interaction (rotation, entanglement). A large part of this energy is then dissipated into heat. The measured complex viscosity of this polymer solution was 0.27 Pa s at 10.0 rad/s.
FIG. 8 shows the same material at 20° C. An increase in viscosity to 1.46 Pa s at 10 rad/s was observed. This value is approximately 7-fold higher than the viscosity at 37° C.
FIG. 9 shows a frequency sweep for the CD-PEG$_{3400}$ polymer crosslinked with 36.5 mg/ml of di-Adamantane-PEG. Addition of the cross linker increased the viscosity of the matrix over 100 fold to approximately 33.1 Pa s. At the same time, tan δ decreased approximately 3-fold to a value of 1.2 and the slope of G' decreased to 0.58. These results are consistent with an increase in elastic behavior. Structurally, the movement of the polymer within the material is constrained and energy applied can be stored in a more limited way between network points. This behavior is also confirmed by the observation that the crosslinked matrix has a tendency to draw long strings when an immersed object is pulled away from the surface. Over all, viscous forces still are dominant (tan δ>1) (see FIG. 11).
FIG. 10 shows the crosslinked polymer at 20° C. Viscosity increased further to approximately 50 Pa s while all the other characteristics remained similar.
As a comparison, FIG. 11 shows a frequency sweep for the collagen matrix at 2.4 mg/ml. The collagen matrix in its set state (i.e., at 37° C.) exhibits a typical gel behavior, with tan δ at a low value of 0.14, a slope of G' of 0.07. Structurally, this is an indication of a permanent and orderly arranged network. Applied energy can only be stored to limited extent between network nodes and is returned to a large extent. The complex viscosity of this material was 12.8 Pa s.

Example 30

In Vitro Biocompatibility Experiment
Methods:
A matrix was prepared using 58 kD cyclodextrin (CD) polymer prepared according to Example 3, method II, and crosslinking agent from Example 9, method II. Upon formulation of the matrix, either pEGFP DNA or GFCB virus was mixed together with the matrix. A low and a high dose of DNA or virus were both formulated. The various treatment groups are listed in Table 2. Final concentration of 58 kD cyclodextrin matrix was 100 mg/mL for all groups. Approximately 100 µL of each respective reagent was pipetted into a 48-well flat bottom plate. Each group was tested in duplicate. The 48-well plate containing the test formulations was allowed to set at room temperature for approximately 30 minutes. $2.5 \times 10^4$ CCD-1074sk cells (human skin fibroblast) were placed on top of the cross-linked matrix formulations in a volume of 200 µL of DMEM media containing 10% Fetal Bovine Serum (FBS). The CCD-1074sk cell line was approximately 70% confluent at the time of cell counting with cell viability greater than 95% via Trypan Blue staining. Each well, containing groups 1-8, was examined daily under an inverted microscope for cell viability and for GFP fluorescence signal. 200 μL of fresh media was added (not replaced) to each of the wells on days 4 and 8 after the start of the experiment. The plate was incubated at 37° C. with 5% $CO_2$.

Synthesis of CD-IPEI

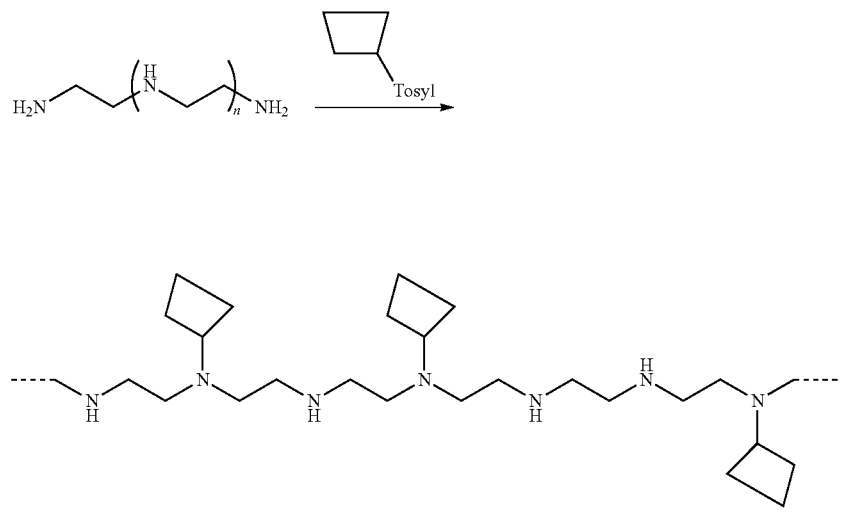

Linear $PEI_{25,000}$ (500 mg, Polysciences, Inc.) and 6-Mono-tosyl-β-Cyclodextrin (3.868 g, Cyclodextrin Technologies Development, Inc.) were dissolved in 36 mL of DMSO. The resulting mixture was stirred at 70° C. for 6 days. The solution turned slightly yellow. The solution was then transferred to a Spectra/Por MWCO 10,000 membrane and dialyzed against water for 6 days. Water was then removed by lyophilization to afford a slightly colored solid. Cyclodextrin/PEI ratio was calculated based on the proton integration of $^1H$ NMR (Varian 300 MHz, $D_2O$) δ 5.08 ppm (s br., $C_1H$ of CD), 3.3-4.1 ppm (m br. $C_2H$—C6H of CD), 2.5-3.2 ppm (m br. $CH_2$ of PEI).

β Cyclodextrin Polymers (CDP-Imidazole).

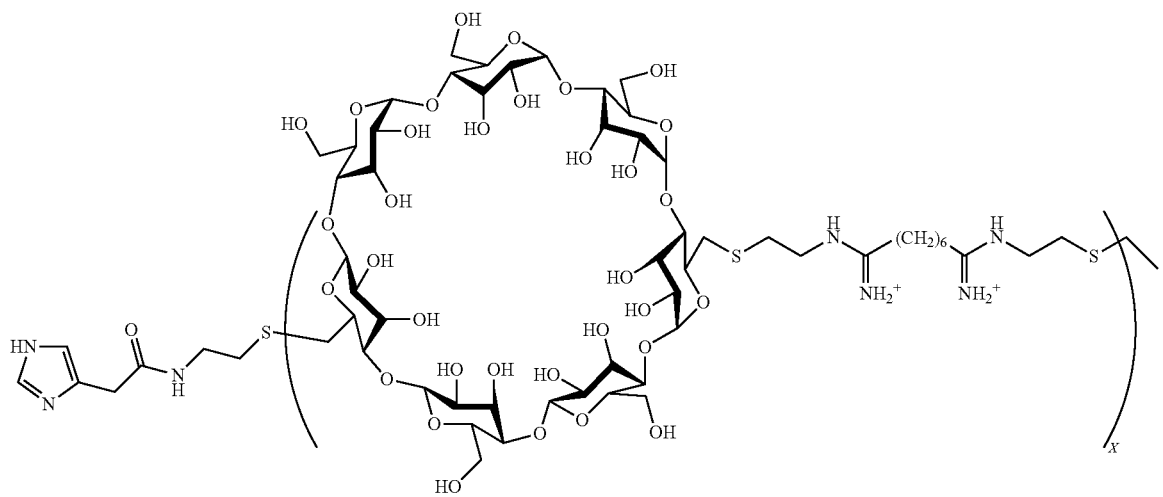

-continued

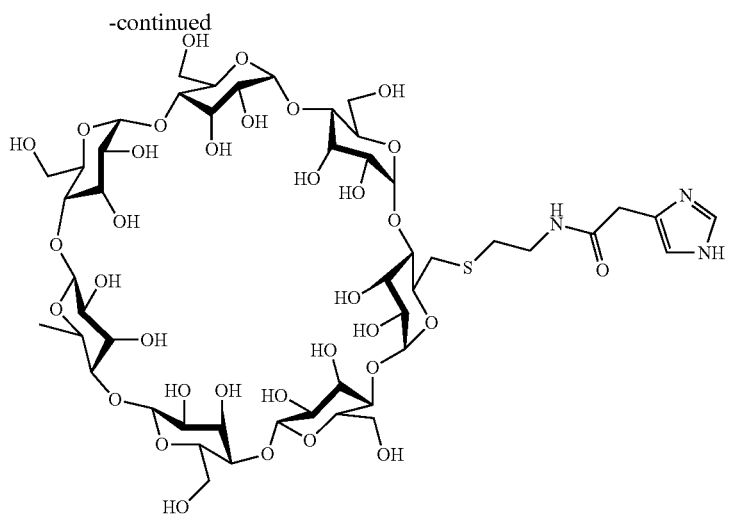

βCDP was synthesized according to previously described procedures (Gonzalez, H., Hwang, S. & Davis, M. (1999) *Bioconjugate Chem.* 10, 1068-74). Imidazole was conjugated to the βCDP polymer by amidation of the primary amines at the end of the polymer with 4-imidazoleacetic acid (Aldrich, St. Louis, Mo.) (Sehgal, D. & Vijay, I. (1994) *Anal Biochem.* 218, 87-91). In a typical experiment, 200 mg (33.3 µmol) of βCDP were dissolved in 800 µL of 25 mM MES (pH 6.5) buffer to which was added 4-imidazoleacetic acid, sodium salt hydrate (49.3 mg, 0.333 mmol). This solution was used to dissolve 1-ethyl-3-(3-dimethylaminopropyl)carbodiimide (EDC) (0.128 g, 0.666 mmol). Then, N-hydroxysuccinimide (NHS) (3.83 mg, 33.3 µmol) dissolved in 200 AL of 25 mM MES (pH 6.5) buffer was added immediately to the polymer solution. The resulting solution was stirred for 24 h at room temperature and then dialyzed against water using a Spectra Por membrane MWCO 1000. The solution was lyophilized to dryness. The imidazole content was determined by the TNBS assay (Hermanson, G. T. (1996) Bioconjugate Techniques, pp. 132, Academic Press, Rockford, Ill.), followed by UV measurements to quantify the amount of unreacted polymer end groups. The imidazole conjugation was 73%.

TABLE 2

Treatment Groups/Well (48-well Flat Bottom Plate)

| Group # | Treatment |
| --- | --- |
| 1 | 0.25 mg/mL pEGFP + CDP-Imidazole in 58 kD Cyclodextrin |
| 2 | 0.025 mg/mL pEGFP + CDP-Imidazole in 58 kD Cyclodextrin |
| 3 | 0.25 mg/mL pEGFP + CD-1PEI in 58 kD Cyclodextrin |
| 4 | 0.025 mg/mL pEGFP + CD-1PEI in 58 kD Cyclodextrin |
| 5 | $1 \times 10^{10}$ P/mL GFCB in 58 kD Cyclodextrin |
| 6 | $1 \times 10^{9}$ P/mL GFCB in 58 kD Cyclodextrin |
| 7 | Empty Control (Cells Alone) |
| 8 | 58 kD Cyclodextrin Matrix Alone Control |

Figure 12A:
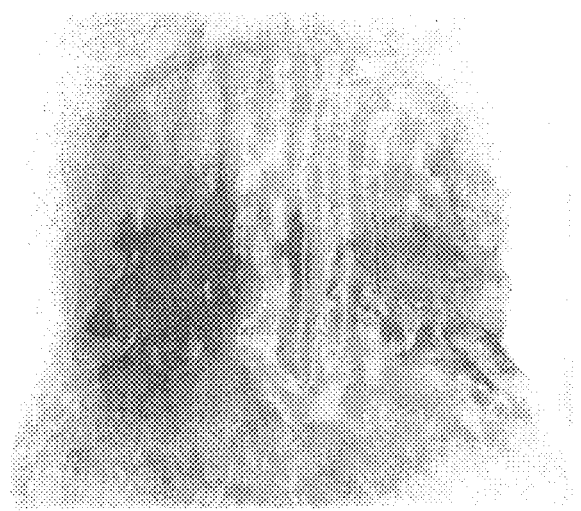
FIG. 12 portrays results of treating wounds with subject compositions. (12A): ICR mouse treated with Matrix A (Left Wound) and Matrix B (Right Wound). Animal shown at sacrifice 4 days post surgery. The purple ink is markings from a surgical pen and not the dye (dark blue/black in color) used in the matrices. Little dye remains on the actual wound site; however, the remaining dye comes from oozing and spreading of the matrices to the surrounding unwounded tissues that occurred after applying the wound dressing. (12B): ICR mouse treated with Matrix A (Left Wound) and Matrix B (Right Wound). Animal shown at sacrifice 4 days post surgery. The left and right wounds show that Matrix A and Matrix B respectively, did not spread to surrounding tissues after injection.
Figure 12B:
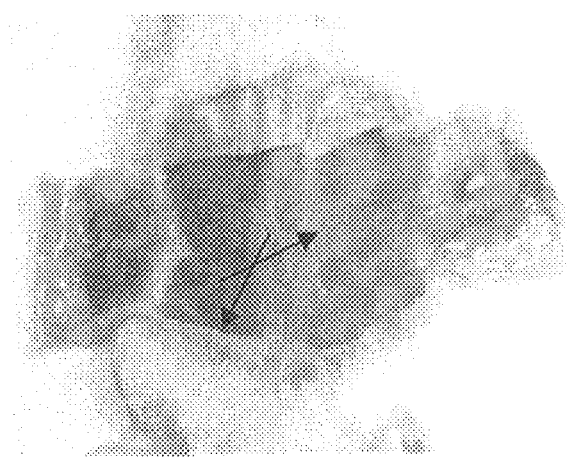

Results:
Day 1: Groups 1-4 started dying. They were starting to lift off the plate. CCD-1074sk cells were "rounded up" morphologically and floating. Groups 5-8 looked healthy. The cells were attached to the plate and "stretched out" morphologically (typical state of fibroblasts); however, none of the groups had GFP expression at this time. See FIG. 12.
Day 2: Groups 5-8 looked healthy. CCD-1074sk cells were attached to the plate and "stretched out". Groups 5-6 (GFCB groups) were positive for GFP expression. The higher dose of GFCB (Group 5) had more GFP expression than the lower dose of GFCB (Group 6). Groups 1, 3, and 4 looked to be completely dead at this time; however, a couple cells had survived in group 2 (0.025 mg/mL pEGFP+CDP-Imidazole in 58 kD Cyclodextrin). There was no detectable GFP expression in groups 1-4.
Day 4: CCD-1074sk cells in groups 1-4 appeared to be dead. Cells were floating. GFP expression was not detectable in any of these groups. Groups 5-8 were healthy. Groups 5-6 were positive to GFP expression, and expression appeared to be even brighter than the day 2.
Day 5: CCD-1074sk cells in group 1-4 were dead and no GFP expression was seen. Groups 5-8 were healthy. Groups 5-6 were positive or GFP expression and once again the expression level appeared to be brighter than the day before.
Day 6: CCD-1074sk cells in groups 1-4 were dead and no GFP expression was seen. Cells were no longer monitored. Groups 5-8 were healthy. Groups 5-6 were still expressing GFP and the expressions level appeared to still be brighter that the day before.
Day 8: CCD-1074sk cells in groups 5-8 still looked healthy. Morphologically, they did not look any different from day 6. They were still expressing GFP and appeared to be at the brightest observed intensity.
Day 12: CCD-1074sk cells in groups 5-8 were healthy. Cell count seemed to be slightly more numerous than day 8; however, GFP expression appeared to be decreasing.
Day 13: CCD-1074sk cells in groups 5-8 appeared healthy, but GFP expression was starting to decrease.

Example 29

Methods:
The components for Matrix A and Matrix B were formulated following the written protocol from Insert Therapeutics, Inc. Matrix A was 100 mg/mL of β-Cyclodextrin-PEG$_{3400}$ polymer (Example 3, method II) in PBS at pH of 7.2 with 4.4 mg/mL of di-Adamantane compound crosslinker (Example 9, method II). The two components were aliquoted and kept separate until used. Matrix B was 100 mg/mL of β-Cyclodextrin-PEG$_{3400}$ polymer in PBS at a pH of 7.2 with 36.5 mg/mL of di-Adamantane PEG$_{3400}$ compound crosslinker. The components were aliquoted and kept separate.

Three different methods of delivery were tested:

1) Delivery of Matrix A into a Wound Site Using a Surgical Dressing and Delivery of Matrix B into a Wound Site Prior to Covering with a Surgical Dressing:

An ICR mouse was anesthetized with ketamine and xylazine. The dorsal region was shaved and two 8 mm dermal punches were made. 50 µL of Matrix A (final adjusted volume) was mixed containing a small amount of dye and then placed onto a small square piece of OpSite dressing. The matrix was allowed to gel for about 2 minutes. During this time, the left wound punch on the mouse was prepared with Mastisol dressing adhesive. The OpSite dressing containing the mixed Matrix A was then flipped over ("sticky" side down) and placed over the left wound site. The right wound punch was prepared with Mastisol adhesive dressing. Matrix B containing a small amount of dye was also made up at a final adjusted volume of 50 µL and placed directly onto the right wound site. This was allowed to gel for about 2 minutes then covered with the OpSite dressing. This animal was allowed to recover from surgery and was sacrificed 4 days later.

2) Delivery of Matrix A with Pre-Mixing and Matrix B without Pre-Mixing into a Wound Site Through a Previously Applied Surgical Dressing:

An ICR mouse was anesthetized with ketamine and xylazine. The dorsal region was shaved and two 8 mm dermal punches were made. Two wound sites were prepared with Mastisol adhesive and 1 single sheet of OpSite dressing was placed over the wounds. Matrix A was prepared for a 50 µL total injection volume containing a small amount of dye. The matrix was drawn up directly into a 1 cc syringe and a 23G needle was placed on the syringe. Excess matrix was expelled from the syringe until approximately 50 µL remained. This material was then injected through the OpSite dressing onto the left wound bed. For the right side wound, Matrix B was prepared for ~100 µL total injection volume. A 1 cc syringe containing a 23G needle was used to draw up approximately 82 µL of Matrix B. A small air pocket was then drawn into the syringe. Approximately 18 µL of the accompanying crosslinker was then drawn into the same syringe needle. Another small air pocket was then drawn into the syringe. Finally, a small amount (~2-4 µL) of dye was drawn into the syringe. A 27G needle was placed at one end of the right wound site through the dressing to vent air from the covered wound site. The syringe with a 23G needle containing the separated components of Matrix B was placed through the dressing (without pre-mixing of the components) and the materials were injected into the wound site. The 27G needle provided venting of the small air pockets in the syringe. The animal was allowed to recover after surgery and was sacrificed 4 days later.

3) Injection of Matrix A and B into PVA Sponges Using Various Gauge Needles:

An HSD rat was anesthetized with ketamine and xylazine and PVA sponges were subcutaneously implanted onto the ventral side of the rat. Incisions were closed with wound clips and the animal was allowed to recover for 4 days. Matrix A was formulated at an adjusted injection volume of ~200 µL with dye (~2-4 µL). The matrix mixture was drawn into a 1 cc syringe through a 22G needle and mixed in the syringe. Attempts were made to remove excess air bubbles. The mixed matrix was injected into the center of a PVA sponge on a sacrificed animal. After a few minutes, the wound site was opened and the sponge area was examined.

Matrix B was prepared for ~200 µL injection. The matrix contained a small amount of dye and was drawn into a 1 cc syringe using a 22G needle, which was removed and replaced with a shorter 23G needle for injection. The materials were mixed in the syringe and an attempt to remove excess air bubbles was made. Matrix was injected into the center of a PVA sponge, allowed to sit for a few minutes, and then the animal was opened for examination of the injected sponge.

Results:

1) Delivery of Matrix A into a Wound Site Using a Surgical Dressing and Delivery of Matrix B into a Wound Site Prior to Covering with a Surgical Dressing:

50 µL of Matrix A (final adjusted volume) was mixed with a small amount of dye, placed onto a small square piece of OpSite dressing, allowed to gel for a short period of time (~2 minutes), and then flipped over ("sticky" side down) on the left wound site. Upon sacrifice of the animal 4 days after surgery, the wound appeared to be dry and the animal was observed to have tolerated Matrix A without difficulties. Matrix appeared to stay in its original position at the time of delivery, i.e., on top of the wound site including some of the surrounding unwounded tissue. The matrix that remained in the wound site was superficial and less abundant than the day of surgery. No gross appearance of inflammation was seen at the wound site. See FIGS. 12A-12B.

Matrix B containing a small amount of dye was also made up at a final adjusted volume of 50 µL and placed directly onto the right wound site and then covered with OpSite dressing. When the animal was sacrificed 4 days later, the wound appeared to be dry and the animal seemed to have tolerated Matrix B well. No inflammation or any other adverse effects were grossly seen around the wound site. The matrix did not disperse onto surrounding tissue after surgery, but rather stayed in the original wound site. The matrix that remained in the wound site at the time of sacrifice was superficial and less abundant than at the day of surgery. See FIGS. 12A-12B.

Figure 13A:
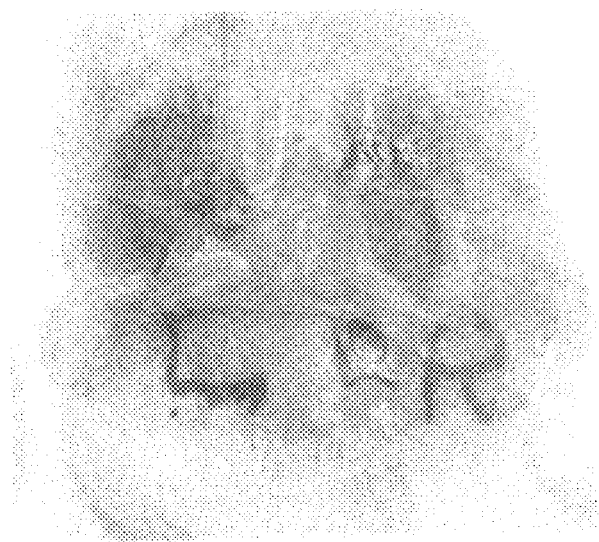
FIG. 13 shows results of treating wounds with subject compositions. (13A): ICR mouse treated with Matrix A (Left Wound) and Matrix B (Right Wound). Animal shown at sacrifice 4 days post surgery. Natural wound contraction can be seen in both left and right wounds. A small amount of dye remaining from the original injections can be seen; however, there is no dye present in the surrounding unwounded tissues. (13B): ICR mouse treated with Matrix A (Left Wound) and Matrix B (Right Wound). Animal shown at sacrifice 4 days post surgery. The left and right wounds show that Matrix A and Matrix B, respectively, did not spread to surrounding tissues after injection.
Figure 13B:

2) Delivery of Matrix A with Pre-Mixing and Matrix B Without Pre-Mixing into a Wound Site Through a Previously Applied Surgical Dressing:

50 µL of Matrix A (final adjusted volume) was mixed with a small amount of dye and then injected directly under the OpSite dressing and on the left wound site. The matrix remained localized in the wound site and did not disperse to the surrounding unwounded tissue. Due to air bubbles in the syringe, it was not possible to make precise measurements of the dosing volume. Upon sacrifice of the animal 4 days after surgery, the wound appeared to be dry and the animal tolerated Matrix A without any observable adverse effects. The matrix stayed in its original position at delivery, i.e., at the wound site including some surrounding unwounded tissue. The matrix did not disperse onto other surrounding tissue after the surgery; however, the matrix was only on the surface of the wound and less abundant than at the time of surgery. Upon gross examination, no inflammation was seen at the wound site. See FIGS. 13A-13B.

100 µL final volume of Matrix B containing a small amount of dye was drawn into a syringe. The various components of the matrix (polymer, crosslinker, and dye) were drawn individually into the syringe with air pockets to separate the individual components. A venting needle to eliminate the air pockets in the syringe was placed in one end of the wound through the dressing and the separated components of Matrix B were injected directly onto the right wound site through the OpSite dressing without any prior mixing. This method required the least amount of pressure to successfully inject the matrix into the wound site, and the venting needle worked to eliminate air pockets under the skin. Once all the components of Matrix B were delivered into the wound site, the matrix gelled quickly by visual elimination and touch, and no matrix leaked out of the dressing. The matrix remained localized to the wound bed and did not grossly spread to surrounding tissues. When the animal was sacrificed 4 days later, the wound appeared to be dry and the animal seemed to have tolerated Matrix B without gross adverse effects. No inflammation or any other adverse effects were seen around the wound site, and the matrix appeared to stay in the local wound area. The matrix was localized to the surface of the wound and at lower amounts than at the original time of injection. See FIGS. 13A-13B.

3) Injection of Matrix A and B into PVA Sponges Using Various Gauge Needles:

Matrix A was prepared with a small amount of dye and drawn into a 1 cc syringe through a 22G needle. Approximately 200 μL of the matrix was injected into a PVA sponge, allowed to sit for a few minutes, and then the animal was opened for examination. Upon examination of the sponge, the matrix appeared to remain localized and had minimal dispersion to the surrounding areas.

Matrix B was prepared, mixed with a small amount of dye, and drawn into a 1 cc syringe with a 22G needle. The 22G needle (1½ inches) was replaced with a shorter 23G needle (1 inch). Approximately 200 μL of the matrix was injected into a PVA sponge, allowed to sit for a few minutes, and then the animal was opened for examination. Upon further examination of the sponge, the matrix appeared to remain localized and had minimal dispersion to the surrounding areas.

Conclusion:

Matrix A and Matrix B both gelled extremely quickly and were very viscous and thick. Even though it is possible to inject the matrices subcutaneously and into PVA sponges, the easiest method of delivery was to draw the various components of the matrix separately (separated by a small pocket of air) into a syringe and then inject directly through a covered dermal punch using a 23G needle. In this method, a second smaller gauge needle can assist in venting excess air from under the wound dressing.

Example 30

Platelet derived growth factor B (PDGF-B) has been shown to stimulate fibroblast proliferation and the synthesis of extracellular matrix. PDGF-B expression was compared by RT-PCR for cyclodextrin and collagen matrices in the rat PVA sponge model.

| Animal # 200 μL Total Injection Volume/Sponge | Grp # | Sponge Injection Contents |
|---|---|---|
| 6 (N = 6 Sponges/Group) | 1: | Collagen alone |
| | 2: | 58 kD Cyclodextrin(CD)-Adamantane Matrix alone |
| | 3: | $2 \times 10^{10}$ PN PGCB in Collagen |
| | 4: | $2 \times 10^{10}$ PN PGCB in CD-Adamantane Matrix |
| | 5: | 50 μg pCTK-PD (plasmid DNA encoding PDGF-B) + L-PEI in CD-Adamantane Matrix |
| | 6: | 50 μg pCTK-PD + $CD_{Imidazole}$ in CD-Adamantane Matrix |

Methods

Six small incisions (0.5 cm) were performed and polyvinyl alcohol (PVA, M-PACTO®) sponges were subcutaneously implanted on the ventral side of male Harlan Sprague-Dawley rats.

Four days after implantation, test and control materials were diluted with vPBS and liquid collagen (Cohesion Technologies®) or 58 kD Cyclodextrin (CD)-Adamantane matrix as described above and injected into PVA sponges. Final collagen formulation was 1.8 mg/mL, pHed with NaOH, and brought up to volume with vPBS. Final 58 kD Cyclodextrin (CD)-Adamantane matrix formulation was 100 mg/mL. 200 μL total volume of test reagent was delivered to each sponge. Animals were sacrificed and sponges were removed 2 days after injections. Sponges were cut into three pieces and the majority of the sponge (~70-80%) was frozen in liquid nitrogen and stored at −80° C. for QPCR and QRT-PCR analysis. A small portion of the sponge was fixed in 4% PFA at 4° C. for 18 hours, paraffin embedded, and sectioned (5 μm). Sections were stained using Masson's Trichrome (cells=black, vasculature=red, and collagen=blue) and Hematoxylin-Eosin methods. Tissue sections were analyzed microscopically for gross histology by two separate investigators.

Results:

Implanted PVA sponges were treated with either collagen, cyclodextrin matrix (CD), $2 \times 10^{10}$ PN of PGCB in Collagen, $2 \times 10^{10}$ PN of PGCB in CD, 50 μg of pCTK-PD+L-PEI in CD, or 50 μg pCTK-PD+$CD_{Imidazole}$ in CD. Sponges were removed 48 hours after treatment and assayed for human PDGF-B RNA and viral DNA by QRT-PCR and QPCR methods, respectively. A portion of each sponge was also fixed, embedded, sectioned, and stained using Masson's Trichrome for gross morphological examination.

Figure 14:
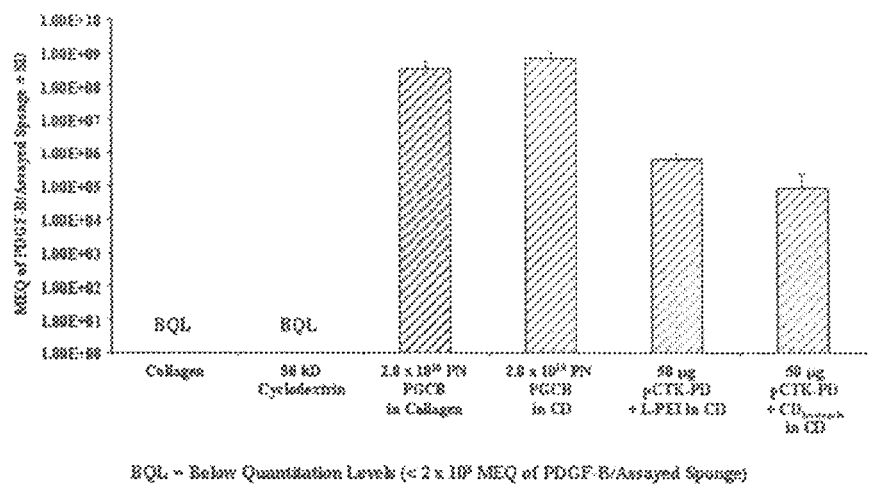
FIG. 14 depicts PDGF-B expression levels within treated sponges. QRT-PCR was performed on individual sponge samples from each treatment group. The data is expressed as the average of 6 sponges assayed±standard deviation.
Figure 15:
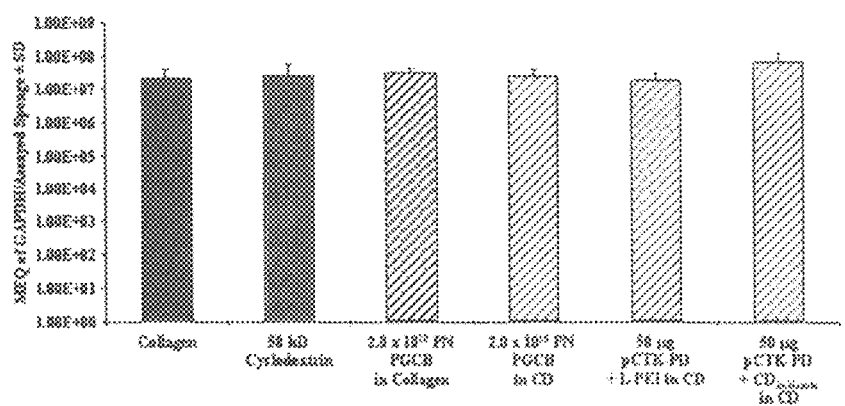
FIG. 15 illustrates GAPDH RNA levels within treatment groups.

QRT-PCR (quantitative RT-PCR) analysis for human PDGF-B RNA expression showed that sponges treated with $2 \times 10^{10}$ PN of PGCB in CD had the highest average RNA content of $7.0 \times 10^8$ MEQ of PDGF-B/assayed sponge (FIG. 14). Sponges treated with $2 \times 10^{10}$ PN of PGCB in Collagen had similar average levels of PDGF-B RNA at $3.2 \times 10^8$ MEQ of PDGF-B/assayed sponge. Sponges treated with 50 μg of pCTK-PD+L-PEI in CD and 50 μg pCTK-PD $CD_{Imidazole}$ in CD had PDGF-B RNA levels of $6.8 \times 10^5$ and $9.1 \times 10^4$ MEQ of PDGF-B/assayed sponge, respectively. Finally, sponges treated with either Collagen or Cyclodextrin showed no detectable levels of PDGF-B RNA (FIG. 14, Table 3). A Student's t-test analysis showed that all sponge treatment groups were statistically different ($p \leq 0.05$) except for the sponge comparisons between $2 \times 10^{10}$ PN of PGCB in collagen and $2 \times 10^{10}$ PN of PGCB in CD (Table 4). GAPDH QRT-PCR control assays were also performed to monitor RNA quality and total RNA per sample. The results showed a consistent amount of RNA ranging from $1.9 \times 10^7$ to $6.9 \times 10^7$ MEQ of GAPDH/assayed sponge for all treatment groups (FIG. 15).

TABLE 3

QRT-PCR Results for hPDGF-B RNA Detection.

| Group | Count (n) | Mean | Std. Dev. | Std. Err. |
|---|---|---|---|---|
| Collagen | 6 | BQL | • | • |
| 58 kD CD | 5 | BQL | • | • |
| $2 \times 10^{10}$ PN PGCB in Collagen | 6 | 3.2E+8 | 2.0E8 | 8.2E+7 |
| $2 \times 10^{10}$ PN PGCB in CD | 6 | 7.0E+8 | 4.1E+8 | 1.7E+8 |
| 50 μg pCTK-PD + L-PEI in CD | 6 | 6.9E+5 | 2.9E+5 | 1.2E+5 |
| 50 μg pCTK-PD + $CD_{Imidazole}$ in CD | 6 | 9.1E+4 | 1.7E+5 | 7.1E+4 |

BQL = Below Quantitation Levels (<2 × $10^3$ MEQ of PDGF-B/Assayed Sponge)
MEQ = Molecular Equivalent is an arbitrarily assigned number based on the dilution factor of a positive control.

TABLE 4

Statistical Analysis of
hPDGF-B RNA between Treatment Groups.

| Unpaired Comparison of Treatment Groups | p-Value |
|---|---|
| $2 \times 10^{10}$ PN PGCB in Collagen vs. $2 \times 10^{10}$ PN PGCB in CD | 0.0699 |
| $2 \times 10^{10}$ PN PGCB in Collagen vs. 50 µg pCTK-PD + L-PEI in CD | 0.0030 |
| $2 \times 10^{10}$ PN PGCB in Collagen vs. 50 µg pCTK-PD + $CD_{Imidazole}$ in CD | 0.0030 |
| $2 \times 10^{10}$ PN PGCB in CD vs. 50 µg pCTK-PD + L-PEI in CD | 0.0020 |
| $2 \times 10^{10}$ PN PGCB in CD vs. 50 µg pCTK-PD + $CD_{Imidazole}$ in CD | 0.0020 |
| 50 µg pCTK-PD + L-PEI in CD vs. 50 µg pCTK-PD + $CD_{Imidazole}$ in CD | 0.0014 |

Note:
Statistical analyses could not be performed for collagen and 58 kD CD treatment groups.

Figure 16:
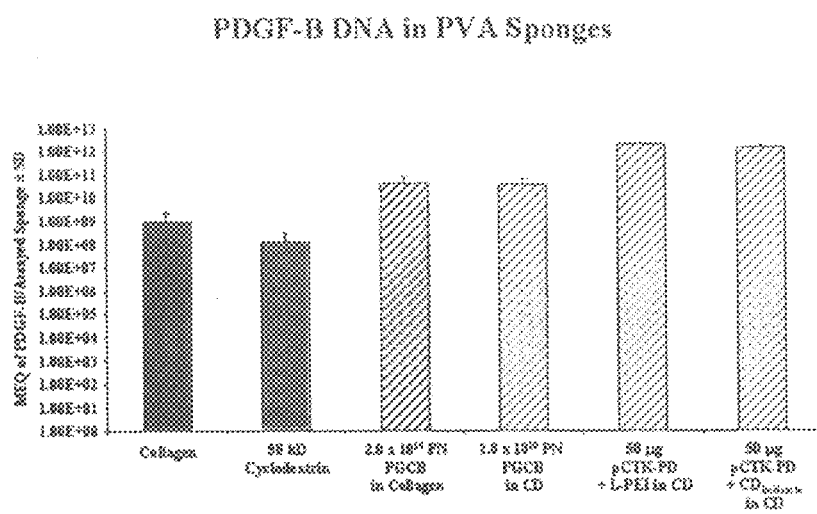
FIG. 16 shows viral PDGF-B DNA within treated sponges. QPCR assays were performed on sponge samples from each treatment group. PCR primers targeted specific expression of human PDGF-B sequence and do not cross react with rat PDGF-B DNA.
Figure 17:
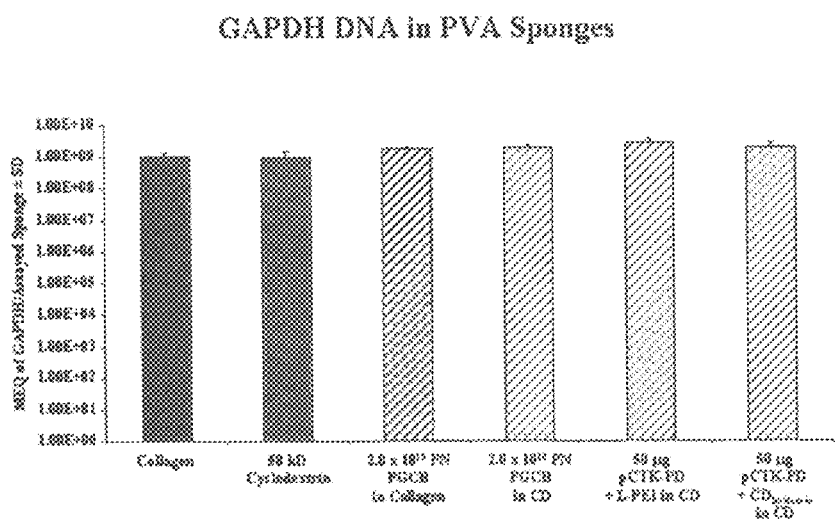
FIG. 17 portrays GAPDH DNA content within sponges.

QPCR (quantitative PCR) analysis for human PDGF-B DNA showed that sponges treated with 50 µg of pCTK-PD+ L-PEI in CD and 50 µg pCTK-PD+$CD_{Imidazole}$ in CD had the highest average levels at $2.4 \times 10^{12}$ and $1.7 \times 10^{12}$ MEQ of PDGF-B/assayed sponge, respectively (FIG. 16, Table 5). Sponges treated with $2 \times 10^{10}$ PN of PGCB in Collagen and $2 \times 10^{10}$ PN of PGCB in CD had average human PDGF-B DNA levels of $4.5 \times 10^{10}$ and $4.1 \times 10^{10}$ MEQ of PDGF-B/assayed sponge, respectively. However, sponges treated with collagen or cyclodextrin also had positive PDGF-B DNA levels at $9.8 \times 10^{8}$ and $1.3 \times 10^{8}$ MEQ of PDGF-B/assayed sponge, respectively. A Student's t-test analysis showed that all groups were statistically different ($p \leq 0.05$) except for sponge comparisons between collagen and cyclodextrin and between $2 \times 10^{10}$ PN of PGCB in collagen and $2 \times 10^{10}$ PN of PGCB in CD treatment groups (Table 6). Mouse GAPDH quantification was performed to ensure the quality of DNA and equal amount of DNA input, and the results ranged from $9.4 \times 10^{8}$ to $2.8 \times 10^{9}$ MEQ of GAPDH/assayed sponge (FIG. 17).

TABLE 5

PCR Results for Viral PDGF-B Detection within Sponges

| Group | Count (n) | Mean | Std. Dev. | Std. Err. |
|---|---|---|---|---|
| Collagen | 6 | 9.8E+8 | 1.5E+9 | 6.1E+8 |
| 58 kD CD | 5 | 1.3E+8 | 2.1E+8 | 9.2E+7 |
| $2 \times 10^{10}$ PN PGCB in Collagen | 6 | 4.5E+10 | 3.9E+10 | 1.6E+10 |
| $2 \times 10^{10}$ PN PGCB in CD | 6 | 4.1E+10 | 2.3E+10 | 9.2E+9 |
| 50 µg pCTK-PD + L-PEI in CD | 6 | 2.4E+12 | 1.1E+11 | 4.6E+10 |
| 50 µg pCTK-PD + $CD_{Imidazole}$ in CD | 6 | 1.7E+12 | 4.1E+11 | 1.7E+11 |

TABLE 6

Statistical Analysis of
human PDGF-B DNA Content within Sponges

| Unpaired Comparison of Treatment Groups | p-Value |
|---|---|
| Collagen vs. 58 kD CD | 0.2382 |
| Collagen vs. $2 \times 10^{10}$ PN PGCB in Collagen | 0.0207 |
| Collagen vs. $2 \times 10^{10}$ PN PGCB in CD | 0.0015 |
| Collagen vs. 50 µg pCTK-PD + L-PEI in CD | <0.0001 |
| Collagen vs. 50 µg pCTK-PD + $CD_{Imidazole}$ in CD | <0.0001 |
| 58 kD CD vs. $2 \times 10^{10}$ PN PGCB in Collagen | 0.0321 |
| 58 kD CD vs. $2 \times 10^{10}$ PN PGCB in CD | 0.0030 |
| 58 kD CD vs. 50 µg pCTK-PD + L-PEI in CD | <0.0001 |
| 58 kD CD vs. 50 µg pCTK-PD + $CD_{Imidazole}$ in CD | <0.0001 |
| $2 \times 10^{10}$ PN PGCB in Collagen vs. $2 \times 10^{10}$ PN PGCB in CD | 0.8197 |
| $2 \times 10^{10}$ PN PGCB in Collagen vs. 50 µg pCTK-PD + L-PEI in CD | <0.0001 |
| $2 \times 10^{10}$ PN PGCB in Collagen vs. 50 µg pCTK-PD + $CD_{Imidazole}$ in CD | <0.0001 |
| $2 \times 10^{10}$ PN PGCB in CD vs. 50 µg pCTK-PD + L-PEI in CD | <0.0001 |
| $2 \times 10^{10}$ PN PGCB in CD vs. 50 µg pCTK-PD + $CD_{Imidazole}$ in CD | <0.0001 |
| 50 µg pCTK-PD + L-PEI in CD vs. 50 µg pCTK-PD + $CD_{Imidazole}$ in CD | 0.0018 |

Figure 18:
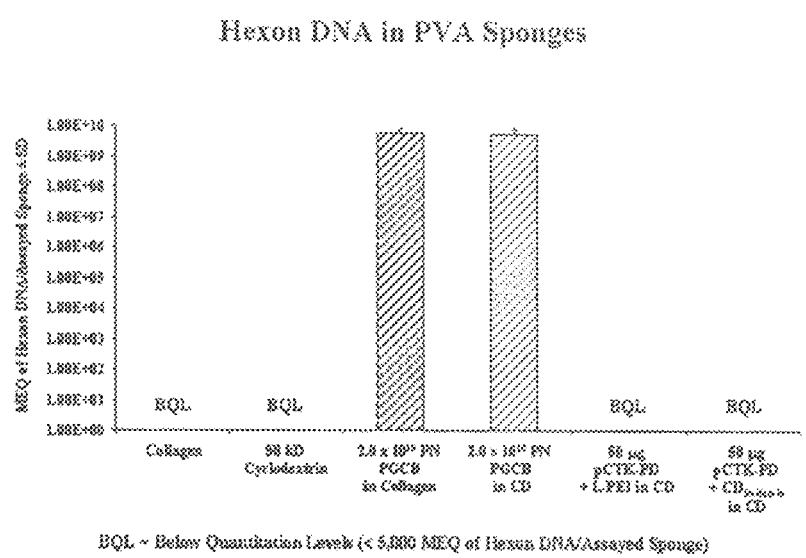
FIG. 18 depicts viral hexon DNA within sponge treatment groups.

QPCR results showed significant levels of PDGF-B DNA detected in collagen and cyclodextrin control sponges. The source of the contribution for this observation has not been completely determined; however, hexon QPCR results, which will only detect hexon sequence contained in adenovirus, indicated that DNA detected in control sponges derived from PCTK-PD plasmid (FIG. 18). Since PDGF-B RNA was not detected in control sponges, this suggests that contamination most likely occurred at or after the time of sponge harvest.

TABLE 7

Summary PVA Sponge Morphological Analysis.

| Group | Capsule Size | Immune Response | Granulation Tissue | Collagen Deposition | Vasculature |
|---|---|---|---|---|---|
| Collagen | Thin | Minimal | Minimal | Minimal | Minimal |
| 58 kD CD | Thin to Moderate | Light to Moderate | Minimal to Light | Minimal | Light to Moderate |
| $2 \times 10^{10}$ PN PGCB in Collagen | Thick | Moderate | Minimal to Light | Light | Moderate to Heavy |
| $2 \times 10^{10}$ PN PGCB in CD | Very Thick | Severe | Minimal to Light | Light | Moderate |
| 50 µg pCTK-PD + L-PEI in CD | Thin to Moderate | Light to Moderate | Minimal to Light | Minimal | Light to Moderate |
| 50 µg pCTK-PD + $CD_{Imidazole\ in\ CD}$ | Thin to Moderate | Light to Moderate | Minimal to Light | Minimal | Light to Moderate |

5 μm, Masson's Trichrome stained paraffin sections were analyzed by two separate observers. Sponge characteristics were qualitatively evaluated by the following criteria: Minimal<Light<Moderate<Heavy<Severe for all categories except Capsule Size. The following criteria were used for evaluation of Capsule Size: Thin<Moderate<Thick<Very Thick.

Figure 19:
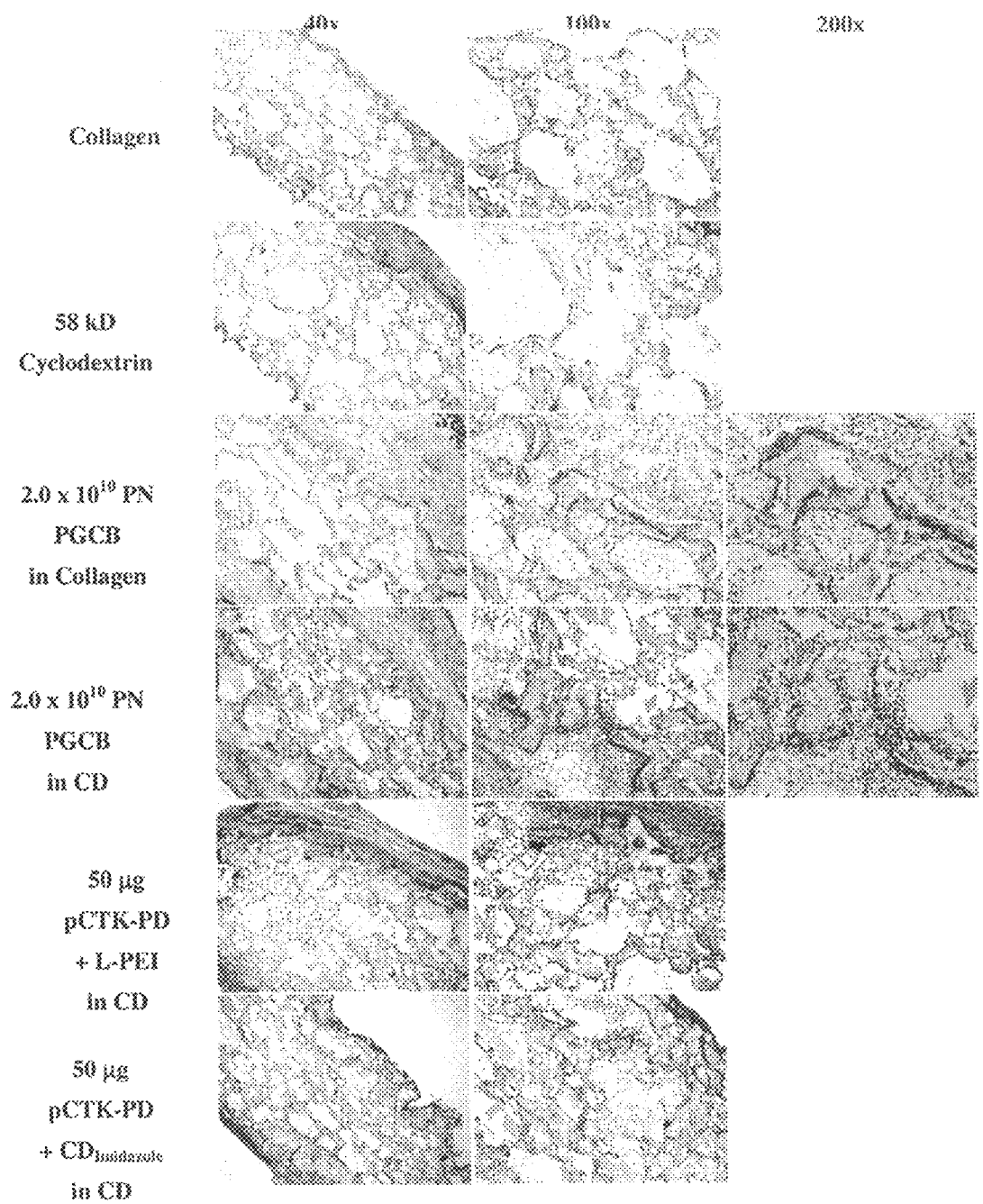
FIG. 19 provides morphological analysis of PVA sponges.

Morphological analysis of the sponges was performed to evaluate host immune responses. Although this study was designed with gene expression and inflammation as primary endpoints, granulation tissue formation, collagen deposition, and neo-vascularization were also analyzed when present. Upon harvest, sponges treated with $2\times10^{10}$ PN of PGCB in CD had an observable and elevated amount of exudate within and surrounding the sponges (Table 7, FIG. 19). These sponges were also much larger in size than other groups. Gross histological examination revealed that sponges treated with $2\times10^{10}$ PN of PGCB in CD had a severe immune response characterized by a thick capsule and the presence of cellular infiltrate. Granulation tissue, collagen, and neo-vascularization were also observed. Sponges treated with $2\times10^{10}$ PN of PGCB in collagen also showed granulation tissue formation, collagen deposition, and neo-vascularization; however, the immune response was not as severe as sponges treated with PGCB in CD. Sponges treated with cyclodextrin alone, 50 μg of pCTK-PD+L-PEI in CD, or 50 μg pCTK-PD+CD$_{Imidazole}$ in CD all had similar results with minimal amounts of granulation tissue. The overall immune response found in these treatments groups was similar to sponges treated with PGCB in collagen. Finally, sponges treated with the collagen alone were found to have minimal amounts of tissue, collagen, or vasculature as well as a minimal immune response.

All of the above-cited references and publications are hereby incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A polymer composition comprising:
   a linear biocompatible polymer including a plurality of inclusion hosts,
   linking molecules, each linking molecule comprising a PEG moiety and at least two adamantane moieties that form inclusion complexes with the inclusion hosts, and
   at least one therapeutic agent,
   wherein the linking molecules cross-link the polymer solely through inclusion complexes; and
   wherein the therapeutic agent is covalently attached to an adamantane moiety.

2. The polymer composition of claim 1, wherein the inclusion hosts are cyclodextrin moieties.

3. The polymer composition of claim 1, wherein the therapeutic agent is a nucleic acid.

4. The polymer composition of claim 3, wherein the nucleic acid is provided in a delivery system selected from a virus, a polymer, and a liposome.

5. The polymer composition of claim 1, wherein the therapeutic agent is a protein, a polypeptide, or a small organic molecule.

6. The polymer composition of claim 1, wherein the therapeutic agent is a protein or polypeptide.

7. The polymer composition of claim 1, further comprising at least one adjuvant.

8. The polymer composition of claim 1, further comprising an adjuvant that increases the effectiveness of the therapeutic agent.

9. The polymer of claim 1, wherein the linking molecules cross-link the polymer intramolecularly.

10. The polymer of claim 1, wherein the linking molecules cross-link the polymer intermolecularly.

11. The polymer composition of claim 2, wherein the cyclodextrin moieties are within the polymer chain.

12. The polymer composition of claim 2, wherein the cyclodextrin moieties are appended to the polymer chain.

13. The polymer composition of claim 1, wherein the linear biocompatible polymer is biodegradable.

14. The polymer composition of claim 1, wherein the linking molecule comprises at least three adamantane moieties.

* * * * *